(12) United States Patent
Shaw

(10) Patent No.: US 12,396,704 B1
(45) Date of Patent: Aug. 26, 2025

(54) ULTRASONIC TRANSDUCER PROBE HOLDER

(71) Applicant: William Shaw, Oak Ridge, NC (US)

(72) Inventor: William Shaw, Oak Ridge, NC (US)

(*) Notice: Subject to any disclaimer, the term of this patent is extended or adjusted under 35 U.S.C. 154(b) by 141 days.

(21) Appl. No.: 18/124,926

(22) Filed: Mar. 22, 2023

Related U.S. Application Data

(60) Provisional application No. 63/322,259, filed on Mar. 22, 2022.

(51) Int. Cl.
*A61B 8/00* (2006.01)

(52) U.S. Cl.
CPC .......... *A61B 8/4455* (2013.01); *A61B 8/4218* (2013.01); *A61B 8/4281* (2013.01); *A61B 8/4433* (2013.01); *A61B 8/461* (2013.01)

(58) Field of Classification Search
CPC ....... A61B 8/42; A61B 8/4218; A61B 5/6834; A61B 8/4209
See application file for complete search history.

(56) References Cited

U.S. PATENT DOCUMENTS

| | | | |
|---|---|---|---|
| 6,261,231 B1 | 7/2001 | Damphousse et al. | |
| 7,850,613 B2 | 12/2010 | Stribling | |
| 7,857,272 B1 * | 12/2010 | Hickey | A61B 90/50 248/288.31 |
| 7,914,456 B2 | 3/2011 | Osaka et al. | |
| 8,409,100 B2 | 4/2013 | Caberg et al. | |

(Continued)

FOREIGN PATENT DOCUMENTS

WO 2019229099 A1 12/2019

*Primary Examiner* — Jeffrey G Hoekstra
*Assistant Examiner* — Ashish S Jasani
(74) *Attorney, Agent, or Firm* — Jacob M. Ward; Ward Law Office LLC

(57) ABSTRACT

An ultrasonic transducer probe holder suitable for holding an ultrasonic transducer probe of a medical ultrasound system to hold or secure the probe in place against a patent as an ultrasound technician releases the probe may include a grip portion and a skirt portion. The grip portion may be configured for deployment on the ultrasonic transducer probe. The grip portion may provide a comfortable and secure grip for the ultrasound technician as the technician applies the ultrasonic transducer probe against the skin of the patient. The ultrasonic transducer probe with the grip portion thereon may be insertable in the skirt portion of the ultrasonic transducer probe holder. The skirt portion may be configured to hold or support the ultrasonic transducer probe in an upward-standing position while forming a vacuum seal against the skin of the patient. A stand assembly may be configured for mounting on a bed, table, or other support on which the patient reclines. The stand assembly may be configured to hold or support the ultrasonic transducer probe holder as the holder remains deployed on the ultrasonic transducer probe. Accordingly, the stand assembly may maintain the ultrasonic transducer probe in place against the patient's skin to reduce or eliminate the manual pressure required for the technician to maintain the ultrasonic transducer probe in place during an echocardiography or other ultrasound procedure. The ultrasonic transducer probe holder may prevent carpel tunnel syndrome and other repetitive stress injuries in the hand of the technician.

6 Claims, 52 Drawing Sheets

(56) References Cited

U.S. PATENT DOCUMENTS

| | | |
|---|---|---|
| 8,535,230 B2 | 9/2013 | Maschke |
| 8,721,552 B2 | 5/2014 | Anderson et al. |
| 8,721,565 B2 | 5/2014 | Hashimshony et al. |
| 8,784,320 B2 | 7/2014 | Zwirn |
| 8,855,739 B2 | 10/2014 | Nagata et al. |
| 10,335,116 B2 | 7/2019 | Boctor et al. |
| 10,603,010 B2 | 3/2020 | Kelly |
| 10,792,011 B2 | 10/2020 | Toume et al. |
| 10,987,083 B2 | 4/2021 | Beri |
| 2007/0129634 A1* | 6/2007 | Hickey ............... F16M 13/027 600/439 |
| 2008/0021317 A1 | 1/2008 | Sumanaweera |
| 2008/0287750 A1 | 11/2008 | Hashimony et al. |
| 2012/0022376 A1 | 1/2012 | Amara et al. |
| 2014/0121520 A1 | 5/2014 | Wang et al. |
| 2015/0094587 A1 | 4/2015 | Chen et al. |
| 2017/0252002 A1 | 9/2017 | Mine et al. |
| 2018/0125449 A1 | 5/2018 | Mauldin, Jr. et al. |
| 2018/0132724 A1 | 5/2018 | Waechter-Stehle et al. |
| 2018/0279992 A1 | 10/2018 | Frankel et al. |
| 2019/0150895 A1 | 5/2019 | Tian et al. |
| 2019/0209129 A1 | 7/2019 | Choi |
| 2020/0015783 A1 | 1/2020 | Sturnick |
| 2020/0113543 A1 | 4/2020 | Wasielewski |
| 2021/0077069 A1 | 3/2021 | Beacham et al. |
| 2021/0267572 A1* | 9/2021 | Sutton ............... A61B 5/6834 |

* cited by examiner

ULTRASONIC TRANSDUCER PROBE HOLDER

CROSS-REFERENCE TO RELATED APPLICATIONS

This application claims the benefit of U.S. provisional application No. 63/322,259, filed Mar. 22, 2022, and entitled ULTRASONIC TRANSDUCER PROBE HOLDER, which provisional application is hereby incorporated by reference herein in its entirety.

FIELD OF THE INVENTION

The present invention relates generally to medical ultrasound systems used to test for and diagnose heart and other medical conditions, and more particularly, to an ultrasonic transducer probe holder suitable for holding an ultrasonic transducer probe of a medical ultrasound system in place against the skin of a patient as an ultrasound technician manually releases the probe.

Background of the Invention

Clinical medicine may utilize various procedures for diagnostic, therapeutic and/or monitoring purposes. These procedures may be carried out by a skilled operator. Examples of these types of medical procedures include diagnostic and therapeutic radiology, anesthesia, cardiology and surgery.

Medical ultrasound procedures may be used extensively to image soft tissues as well as to carry out interventional procedures such as guidance or placement of needles or catheters. For example, ultrasound procedures may be used in the diagnostic imaging of organs such as the heart or liver. Interventional procedures that utilize ultrasound guidance include central line placement and guidance of nerve blocks. Ultrasound systems may be optimized for contrast and resolution in soft tissue.

Ultrasound imaging is widely used in medical diagnostics procedures. Ultrasound imaging may provide high-resolution images of internal organs and biological tissues deep inside the body as well as functional information which indicates cardiac function and blood flow, for example. Ultrasound imaging may be carried out using an ultrasonic transducer. A typical ultrasonic transducer may include an array of elements that emit incident ultrasonic waves and receive reflected ultrasonic waves. The reflected ultrasonic waves indicate differences in acoustic impedance between respective organs and tissues and are converted into electric signals. Ultrasonic transducers may be capable of operation in a brightness mode, or B-node, and a Doppler mode. In the B-mode, the ultrasonic transducer may use the received ultrasonic waves to generate two-dimensional images of the organ or structure in real-time. In the Doppler mode, the ultrasonic transducer may provide measurements including blood velocity. Doppler ultrasound may be used to estimate blood velocity by transmitting streams of high-frequency ultrasonic waves through the blood, receiving reflected ultrasonic waves reflected or echoed from red blood cells circulating in the blood and analyzing the reflected waves. A velocity profile of the blood is derived from measured changes in the phase of the reflected waves. Doppler scans may be used in the diagnosis of such conditions as heart valve defects, congenital heart disease, artery occlusions, and aneurysms.

Early in a cardiac sonographers' training they are instructed on how to direct a narrow ultrasound beam between ribs of the chest wall and obtain orientations that allow for full interrogation of the heart chambers, vessels, and valves. Using a cigar sized probe in a pencil holding grip they perform a variety of rotations, twists and angulations focusing on obtaining the best quality images. Like a choreographed hand and arm ballet sonographers progress through the various views and obtain images in a coordinated standardized manner. These various contortions required in obtaining these images over time can be very taxing to the muscles and joints of the sonographer. In a 2009 sample by Evans et al, 90% of sonographers reported shoulder pain, with 69% reporting low back pain and more than half (54%) reporting work-related symptoms of the hand and wrist.[2] Unfortunately, there appears to be a culture of "toughness" which frowns upon individuals who might otherwise complain about their musculoskeletal discomforts. From generation-to-generation sonographers share stories of endurance and fighting through pains. Aches and pains have become the rites of passage of a seasoned sonographer. As a result of this work-related trauma international statistics indicate that 80% to 95% of sonographers experience work-related pain with 90% experiencing pain for more than half of their career and 1 in 5 sonographers sustain a career ending work-related injury.

In typical implementation of an ultrasound procedure, an ultrasound technician, also known as a sonographer, may manually place a hand-held ultrasonic transducer against the patient. A water-based gel may be placed between the transducer and the skin of the patient. High frequencies of 7-18 MHz may be emitted from the transducer to image shallow structures, whereas lower frequencies of 1-6 MHz typically having better penetration may be used to image deeper structures. An image is generated and displayed in real time on a display. The sonographer may move the transducer to various locations or positions to obtain the desired image scan.

Due to its manual nature, the output of an ultrasound procedure is highly dependent on the experience and capability of the technician performing the procedure. The results from an ultrasound procedure are not always reproducible between different technicians or scans. Furthermore, the manual process can be tiring for the technician and can cause musculoskeletal disorders due to sustained forces applied in unnatural positions. This may particularly be the case in applications in which the procedure is carried out on obese patients or patients with loose skin, in which it may be required that the transducer be pressed more firmly against the skin of the patient. Thus, a need exists for an ultrasound device that can automate the process of performing ultrasound imaging in order to achieve uniform, consistent, and reproducible ultrasound images.

Work-related musculoskeletal disorders (WRMSDs) are painful injuries affecting the muscles, nerves, ligaments, and tendons of sonographers and of the users of diagnostic medical sonography. WRMSDs develop gradually over time from repeated exposure to risk factors and are among the most frequently reported causes of restricted or lost work time. The Bureau of Labor Statistics predicts an increase of 24% or 27,600 additional sonographers will be needed by 2024, an increase that exceeds average growth. With injury rates as high as 90%, it will be difficult to maintain a skilled work force. WRMSDs can impose a substantial personal toll on those affected since they may no longer be able to work or perform their simple personal tasks and activities of daily living.

These workplace injuries are more prevalent because of intensified work schedules with less resting periods. New imaging modalities add to the already growing and protracted imaging protocols which is associated with increased imaging time and interaction between the sonographer and the computer. In general, the populous has become more obese with prevalence of lung disease both of which intensify the need of the sonographer to use more mechanical forces to improve the inherently poor image quality that these conditions cause. The force required in pushing, pulling, lifting, and gripping and pinching in addition to repetition of studies with very little recovery time and the inherent awkwardness of body position and alignment of head and neck shoulders and arm and wrist all intensify these work-related musculoskeletal traumas. The most common injuries among sonographers are carpal tunnel of the wrist, shoulder capsulitis and tendinitis, epicondylitis of the elbow as well as neck and back strain.

One simple intervention would consist of doing fewer studies and taking longer breaks however, employers typically incentivize doing more studies in the least time possible. Those individuals who might speak out and mention concerns of musculoskeletal trauma are generally viewed as slacker's and complainers. As a result, sonographers take their pain medications in secrecy making use of their hand and wrist supports and work until the pain subdues them into an early retirement or taking time off. Work schedule changes and ergonomic equipment design has only minimally mitigated the ultimate musculoskeletal trauma and possible career ending pain associated within the field of sonography.

The industry standards for the prevention of Work-Related Musculoskeletal Disorders (WRMSDs) in the sonography is the work product of a 2016 Consensus Conference on Work-Related Musculoskeletal Disorders involving 26 sonography related professional organizations, accredited bodies, and manufacturers. This collaborative effort updated the 2003 standards and produced a detailed resource to assist in the reduction of WRMSDs among users of sonographic equipment. These overseeing bodies, organizations and sonographers are all in agreement that attrition rate secondary to musculoskeletal discomforts is much too prevalent in our industry. In this seminal report they give responsibilities and details of action to manufacturers, employers, and sonographers. Leading manufacturers of the more detailed and professional quality cardiac sonography systems require using small grocery cart sized consoles equipped with an upper monitor, mid-level keyboard and lower-level computer system. This console is pushed about on its 4 wheels to various locations within the hospital where a probe is pressed against the patient's chest wall and images transferred through a cord connecting the probe to the computer. It is recommended that the system console not require more than 50 pounds of push pull force with the ability to angulate the monitoring screen as well as the keyboard positioning in a manner to maintain neutral posture during the exam. Further recommendations include light weight transducers and cables, adjustable chair, and exam table with height adjustable to maintain arm abduction of less than 30° as well as a drop away or cut out section on the edge of the table to allow less stressful wrist and hand positioning when imaging the apical region of the chest wall. On behalf of the employer the committee suggests that a culture of safety be a shared commitment between management and employees to ensure safety in the work environment. Effective Jan. 1, 2017, revised occupational safety and health administration (OSHA) requirements for reporting include provisions that encourage workers to report work-related injuries or illnesses to their employers and prohibit employers from retaliating against workers for making those reports. Employers are encouraged to maintain ideal workplace conditions, scheduling breaks and anonymous input of symptoms from their sonographers. Sonographers should follow and be aware of best practices to reduce risk of developing WRMSDs. Sonographers are encouraged to be aware of and proactive in managing personal risks by being mindful of job specific risk, signs, and symptoms for WRMSD. Sonographer should employ muscle recovery time throughout the day.

Point-Of-Care ultrasound systems are smaller, portable, compact ultrasound devices used to image the patient at the site of initial care such as in the emergency room, by paramedic or anesthesiologist. These systems are light weight hand-held and configured to be used without a cart or console but rather images are transferred to an iPad or smart phone. These systems by and large are not used for more detailed studies of professionally trained sonographers but rather give some degree of insight and understanding at the moment of need to immediately help guide medical planning. Since such devices are used by non-traditionally trained sonographers, they have similar risk factors and potential to increase exposure to awkward postures and increased observation of WRMSDs.

To date, there has never been an accessory which could be seamlessly implemented into the regular workflow and profoundly reduce the chronic musculoskeletal trauma endured by full-time sonographers.

Accordingly, there is a need for an ultrasonic transducer probe holder suitable for holding an ultrasonic transducer probe of a medical ultrasound system in place against the skin of a patient as an ultrasound technician manually releases the probe.

SUMMARY OF THE INVENTION

The present invention is directed to an ultrasonic transducer probe holder suitable for holding an ultrasonic transducer probe of a medical ultrasound system in place against the skin of a patient as an ultrasound technician manually releases the probe. The ultrasonic transducer probe holder may include a grip portion and a skirt portion. The grip portion may be configured for deployment on the ultrasonic transducer probe. The grip portion may provide a comfortable and secure grip for the ultrasound technician as the technician applies the ultrasonic transducer probe against the skin of the patient. The ultrasonic transducer probe with the grip portion thereon may be insertable in the skirt portion of the ultrasonic transducer probe holder. The skirt portion may be configured to hold or support the ultrasonic transducer probe in an upward-standing position while forming a vacuum seal against the skin of the patient. A stand assembly may be configured for mounting on a bed, table, or other support on which the patient reclines. The stand assembly may be configured to hold or support the ultrasonic transducer probe holder as the holder remains deployed on the ultrasonic transducer probe. Accordingly, the stand assembly may maintain the ultrasonic transducer probe in place against the patient's skin to reduce or eliminate the manual pressure required for the technician to maintain the ultrasonic transducer probe in place during an echocardiography or other ultrasound procedure. The ultrasonic transducer probe holder may prevent carpal tunnel syndrome and other repetitive stress injuries in the hand of the technician.

In an illustrative implementation of the invention, an ultrasonic transducer probe holder suitable for holding an ultrasonic transducer probe of a medical ultrasound system in place against the skin of a patient as an ultrasound technician manually releases the probe may include a grip portion and a skirt portion. The ultrasonic transducer probe of the medical ultrasound system may include a probe handle. A transducer probe may extend from the probe handle. The grip portion of the ultrasonic transducer probe holder may be configured for deployment around the probe handle of the ultrasonic transducer probe. The grip portion may provide a comfortable and secure grip for the ultrasound technician as the technician applies the ultrasonic transducer probe against the skin of the patient. The ultrasonic transducer probe with the grip portion thereon may be insertable in the skirt portion of the ultrasonic transducer probe holder. The skirt portion may contain, enclose or surround the transducer probe of the ultrasonic transducer probe. A stand assembly may be configured for mounting on a bed, table, or other support on which the patient reclines. The stand assembly may be configured to hold or support the ultrasonic transducer probe holder as the holder remains deployed on the ultrasonic transducer probe. Accordingly, the stand assembly may maintain the ultrasonic transducer probe in place against the patient's skin to reduce or eliminate the manual pressure required for the technician to maintain the ultrasonic transducer probe in place during an echocardiography or other ultrasound procedure. The ultrasonic transducer probe holder may prevent carpel tunnel syndrome and other repetitive stress injuries in the hand of the technician.

In a second aspect, the grip portion of the ultrasonic transducer probe holder may include a grip portion wall, A grip portion interior may be formed by the grip portion wall. The grip portion interior may be suitably sized and configured to contain the probe handle of the ultrasonic transducer probe.

In another aspect, the grip portion wall of the grip portion may include at least one elastic or stretchable material. The grip portion wall may be configured to substantially conform to the diameter or width of the probe handle of the ultrasonic transducer probe.

In another aspect, the grip portion may include a pair of mating or interfacing grip portion sections. The grip portion sections may be configured to receive and contain opposite sides of the probe handle of the ultrasonic transducer probe.

In another aspect, the at least one elastic or stretchable material of the grip portion wall may include silicone.

In another aspect, the ultrasonic transducer probe may include a probe shaft which connects the transducer probe to the probe handle. The grip portion wall of the grip portion may include a grip portion base which is configured to engage the probe shaft and a grip portion middle section extending from the grip portion base and a grip portion apex extending from the grip portion middle section. The grip portion middle section and the grip portion apex of the grip portion may be configured to engage the probe handle of the ultrasonic transducer probe.

In another aspect, the probe handle may have a greater diameter or width than the probe shaft of the ultrasonic transducer probe. The grip portion middle section of the grip portion wall may be expandable to a greater diameter or width than that of the grip portion base and the grip portion apex of the grip portion wall to accommodate the relatively greater diameter or width of the probe handle.

In another aspect, the grip portion base of the grip portion wall may have a grip portion base edge. In placement of the ultrasonic transducer probe in the skirt portion, the grip portion base edge of the grip portion wall may be configured to engage the skirt portion.

In another aspect, a grip portion base opening may be circumscribed by the grip portion base edge of the grip portion base.

In another aspect, the grip portion apex of the grip portion wall may have a grip portion apex edge which is opposite the grip portion base edge of the grip portion base.

In another aspect, a grip portion apex opening may be circumscribed by the grip portion apex edge of the grip portion apex.

In another aspect, the skirt portion may be generally funnel-shaped.

In another aspect, the skirt portion of the ultrasonic transducer probe holder may include a skirt portion wall. A skirt portion interior may be formed by the skirt portion wall. The skirt portion interior may be suitably sized and configured to contain the transducer probe of the ultrasonic transducer probe.

In another aspect, the skirt portion wall of the skirt portion may include at least one elastic or stretchable material. The skirt portion wall may flare or extend outwardly from the transducer probe of the ultrasonic transducer probe.

In another aspect, the at least one elastic or stretchable material of the skirt portion wall may include silicone.

In another aspect, the skirt portion wall of the skirt portion may include a relatively wide skirt portion base and a relatively narrow skirt portion apex extending from the skirt portion base.

In another aspect, the skirt portion base of the skirt portion may have a skirt portion base opening through which the transducer probe is exposed to facilitate contact of the transducer probe with the skin of the patient.

In another aspect, the skirt portion base of the skirt portion wall may include a skin engaging edge which circumscribes the skirt portion base opening of the skirt portion base. The skin engaging edge may be configured to engage the skin of the patient.

In another aspect, the skirt portion apex of the of the skirt portion wall may have a skirt portion apex opening. The skirt portion apex opening may be configured to interface and communicate with the grip portion base opening of the grip portion base of the grip portion wall.

In another aspect, the skirt portion apex of the skirt portion wall may have a skirt portion apex edge which circumscribes the skirt portion apex opening. The skirt portion apex edge of the skirt portion apex may be configured to engage or may be continuous with the grip portion base edge on the grip portion base of the grip portion wall.

In another aspect, the skirt portion wall of the skirt portion may have a skirt portion middle section extending between the skirt portion base and the skirt portion apex. The skirt portion middle section may gradually expand in width or diameter from the skirt portion apex to the skirt portion base.

In another aspect, the stand assembly may include a stand base. A cradle base may be supported by the stand base. An elongated cradle gooseneck may extend from the cradle base. A cradle may be supported by the cradle gooseneck. The ultrasonic transducer probe with the probe holder thereon may be supported by the cradle during use of the probe.

In another aspect, the stand assembly may include a lower base member. At least one base arm may extend from the lower base member. An tipper base member may be supported by the base arm. The cradle base may be supported by the upper base member.

In another aspect, the cradle base may be adjustably mounted with respect to the upper base member.

In another aspect, an elongated base slot may extend through the upper base member of the stand base. The cradle base may adjustably engage the base slot.

In another aspect, the upper base member of the stand base may include at least one electrical outlet.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

Detailed Description

Figure 1:
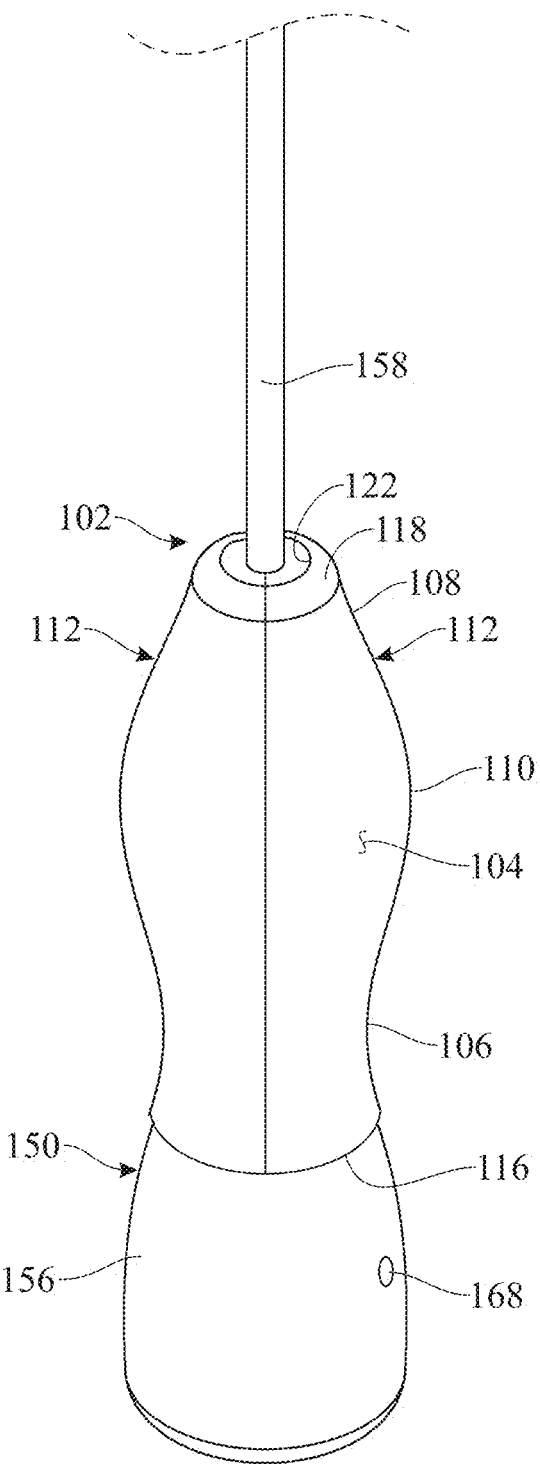
FIG. 1 presents a perspective view of a typical grip portion of an ultrasonic transducer probe holder in accordance with an illustrative embodiment of the present invention, with the grip portion deployed in place on an ultrasonic transducer probe in typical application of the ultrasonic transducer probe holder.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an ultrasonic transducer probe holder suitable for holding an ultrasonic transducer probe of a medical ultrasound system in place against the skin of a patient as an ultrasound technician manually releases the probe.

Figure 11:
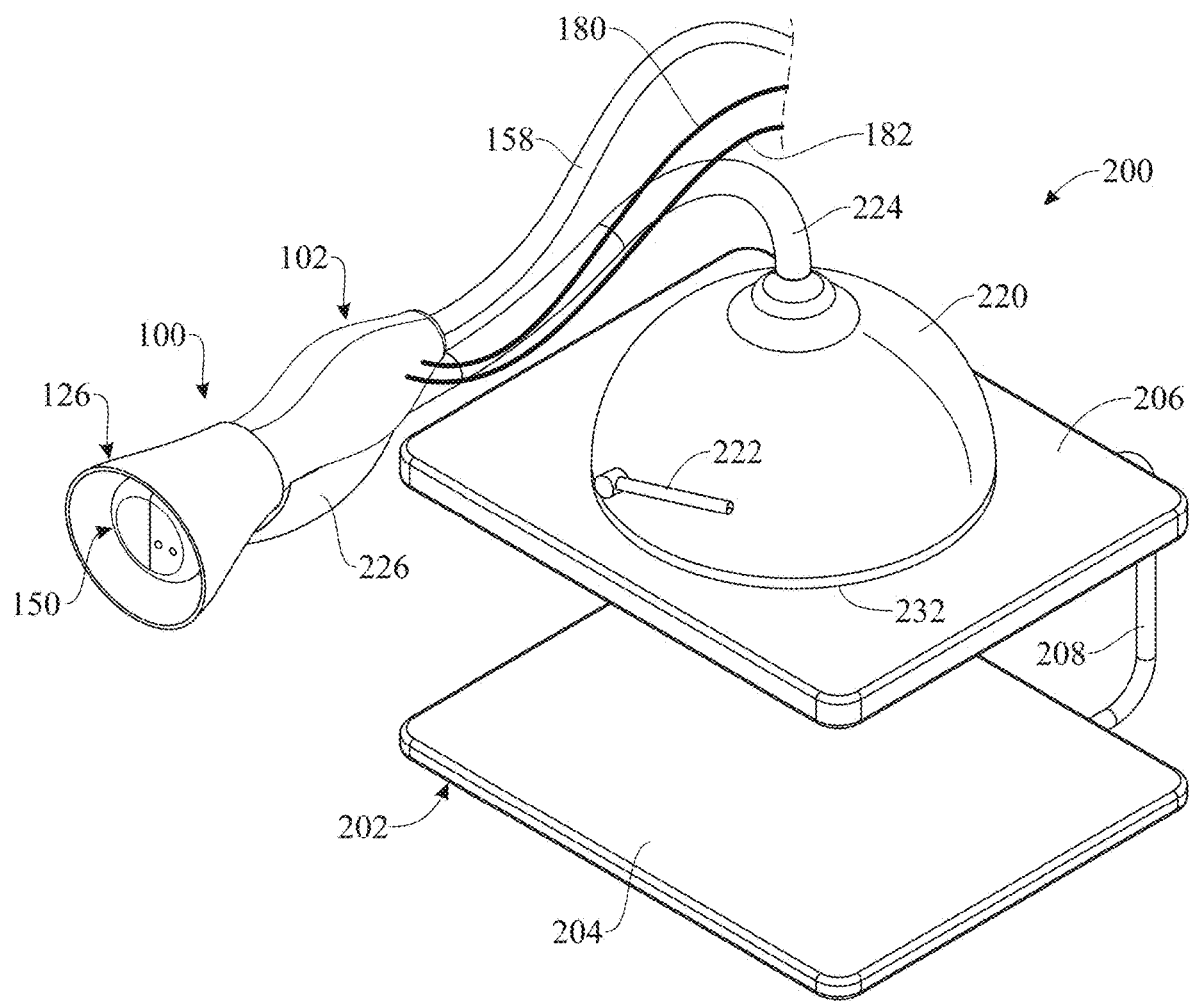
FIG. 11 presents a top perspective view of the stand assembly with the ultrasonic transducer probe holder deployed on the ultrasonic transducer probe and the ultrasonic transducer probe placed in a cradle of the stand assembly.
Figure 12:
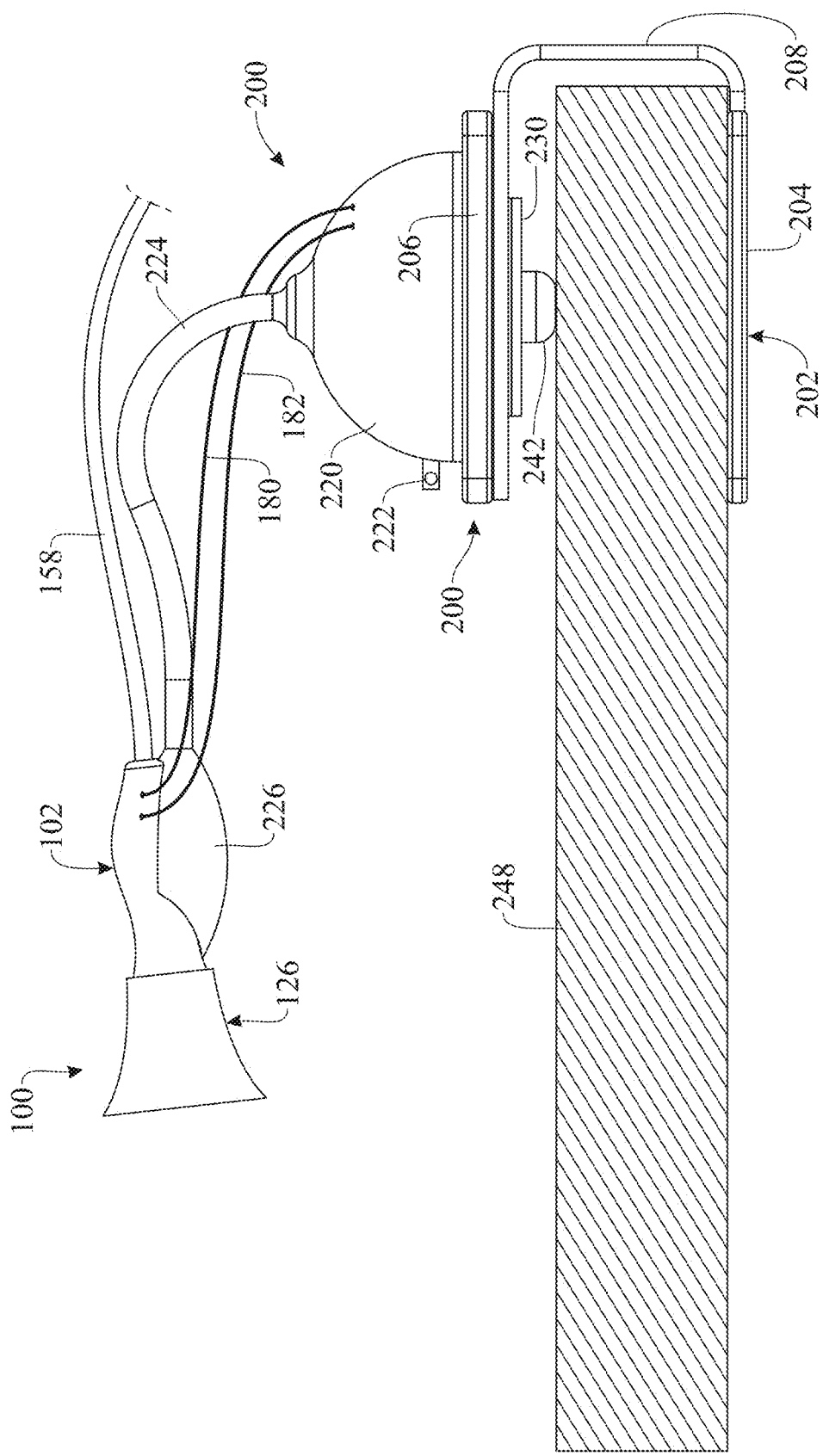
FIG. 12 presents a side view of the stand assembly with ultrasonic transducer probe and probe holder illustrated in FIG. 11, with the stand base of the stand assembly deployed on a table, bed or other support in typical application of the ultrasonic transducer probe holder.

Referring initially to FIGS. 1-6, 11, 12, 14 and 15, an ultrasonic transducer probe holder, hereinafter probe holder 100, is illustrated in accordance with an exemplary embodiment of the present invention. As will be hereinafter further described, the probe holder 100 may be configured for deployment on an ultrasonic transducer probe 150 of a medical ultrasound system (not illustrated). The medical ultrasound system may be standard or conventional, typically having a computer with a user interface and a display. A probe cable 158 may connect the ultrasonic transducer probe 150 to the computer. Accordingly, in typical operation of the medical ultrasound system, which will be hereinafter further described, the ultrasonic transducer probe 150 may be placed against the skin 164 of a patient 162 typically as the patient 162 reclines on a table or bed (not illustrated). As illustrated in FIGS. 11 and 12, a stand assembly 200 may be configured for mounting on a bed, table, or other support 248 (FIG. 12) on which the patient reclines. The stand assembly 200 may be configured to hold or support the probe holder 100 as the probe holder 100 remains deployed on the ultrasonic transducer probe 150. The ultrasonic transducer probe 150 may generate sonic waves which impinge against and through the skin 164 of the patient 162 and receive the reflected sonic waves which echo from the organ or tissue being imaged. The computer may generate 2D or 3D images of the imaged organ or tissue of the patient on the display, typically for diagnostic purposes.

Figure 3:
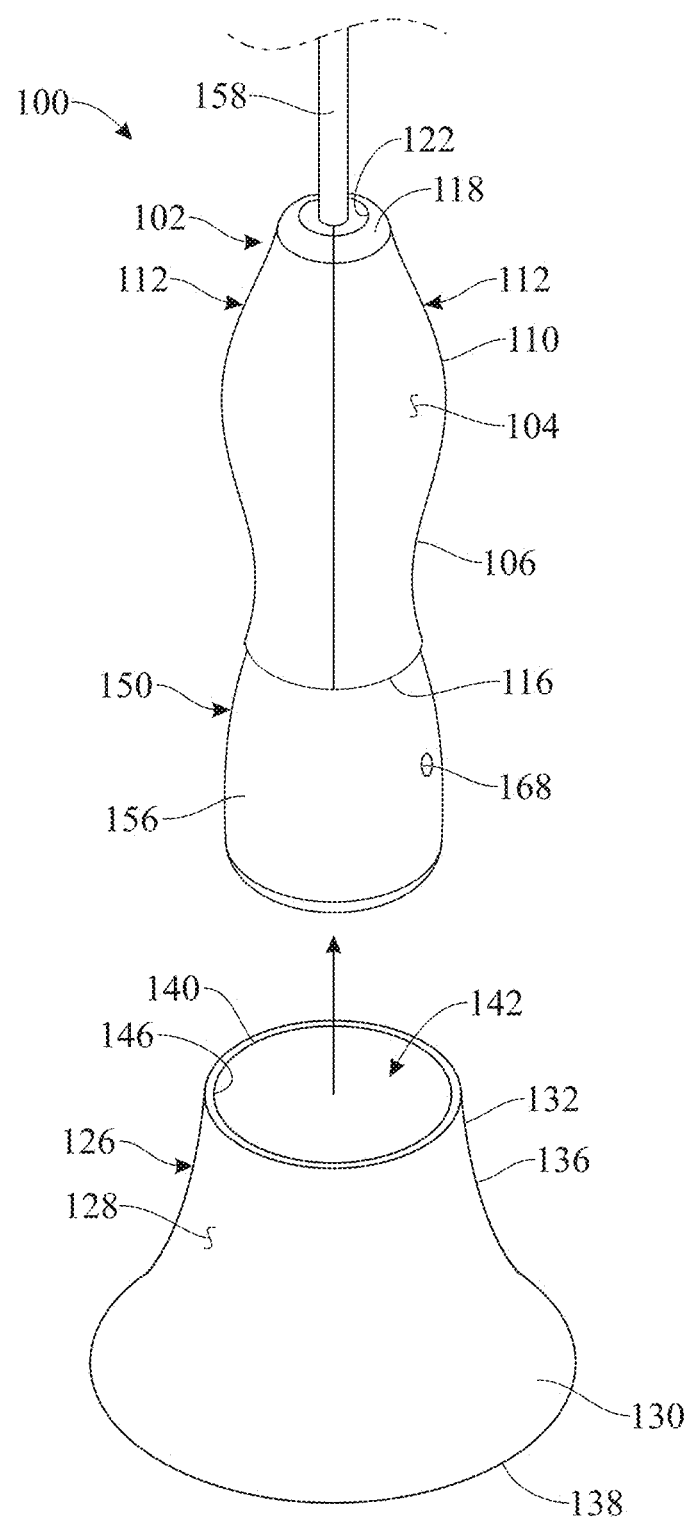
FIG. 3 presents an exploded perspective view of the illustrative ultrasonic transducer probe holder, with the grip portion deployed on the ultrasonic transducer probe and further illustrating typical placement of the ultrasonic transducer probe in the skirt portion of the ultrasonic transducer probe holder.
Figure 14:
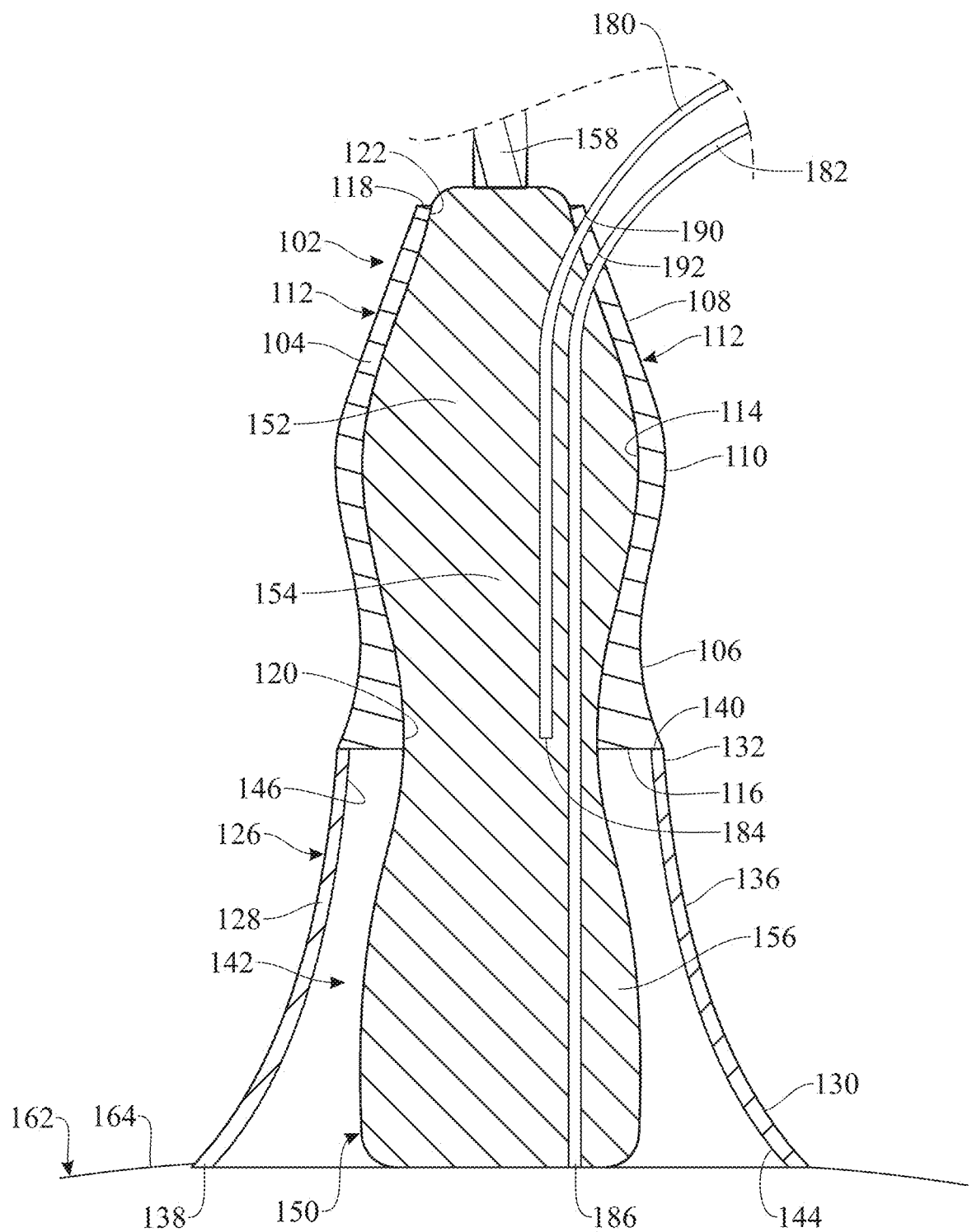
FIG. 14 presents a longitudinal sectional view of the ultrasonic transducer probe with the grip portion deployed in place on the probe, the probe deployed in place in the skirt portion of the ultrasonic transducer probe holder and the skirt portion engaging the skin of a patient in typical application of the ultrasonic transducer probe holder.
Figure 15:
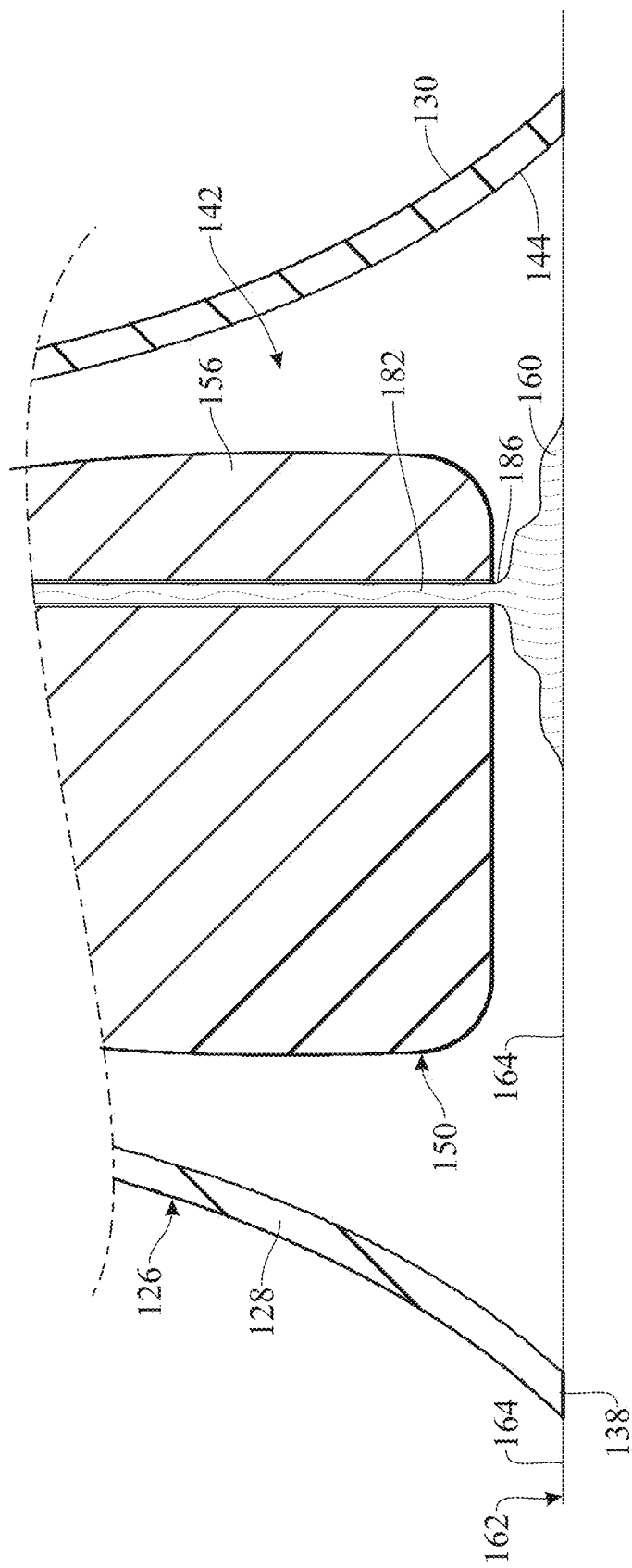
FIG. 15 presents an enlarged sectional view of the skirt portion engaging the skin of the patient and the ultrasonic transducer probe in the skirt portion, more particularly illustrating selective discharge of conductive gel through a gel tube and from a gel tube end in the probe onto the skin of the patient.
Figure 16:
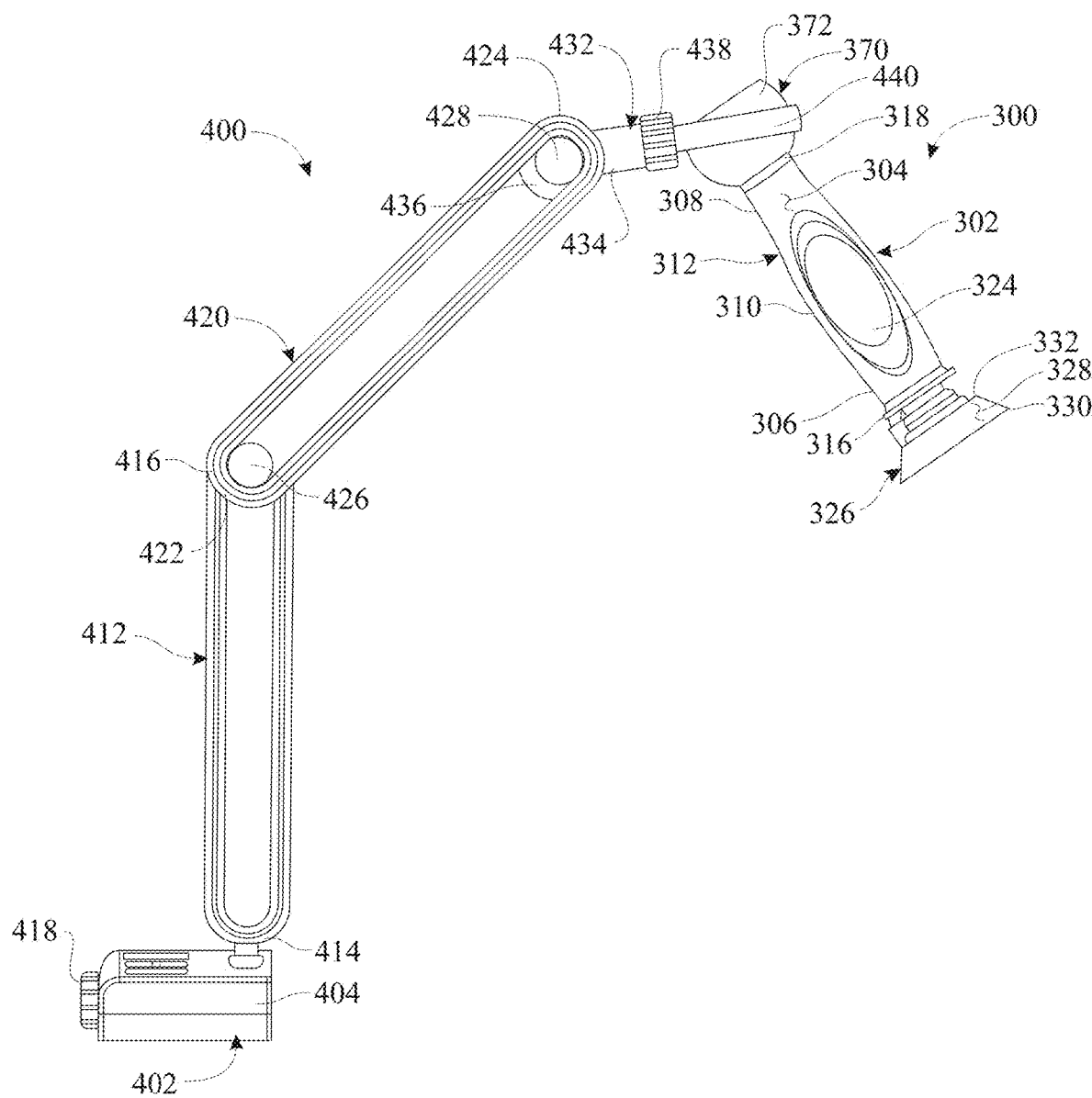
FIG. 16 presents a side view of an ultrasonic transducer probe holder and a typical stand assembly for the probe holder in accordance with an alternative illustrative embodiment of the present invention.
Figure 17:
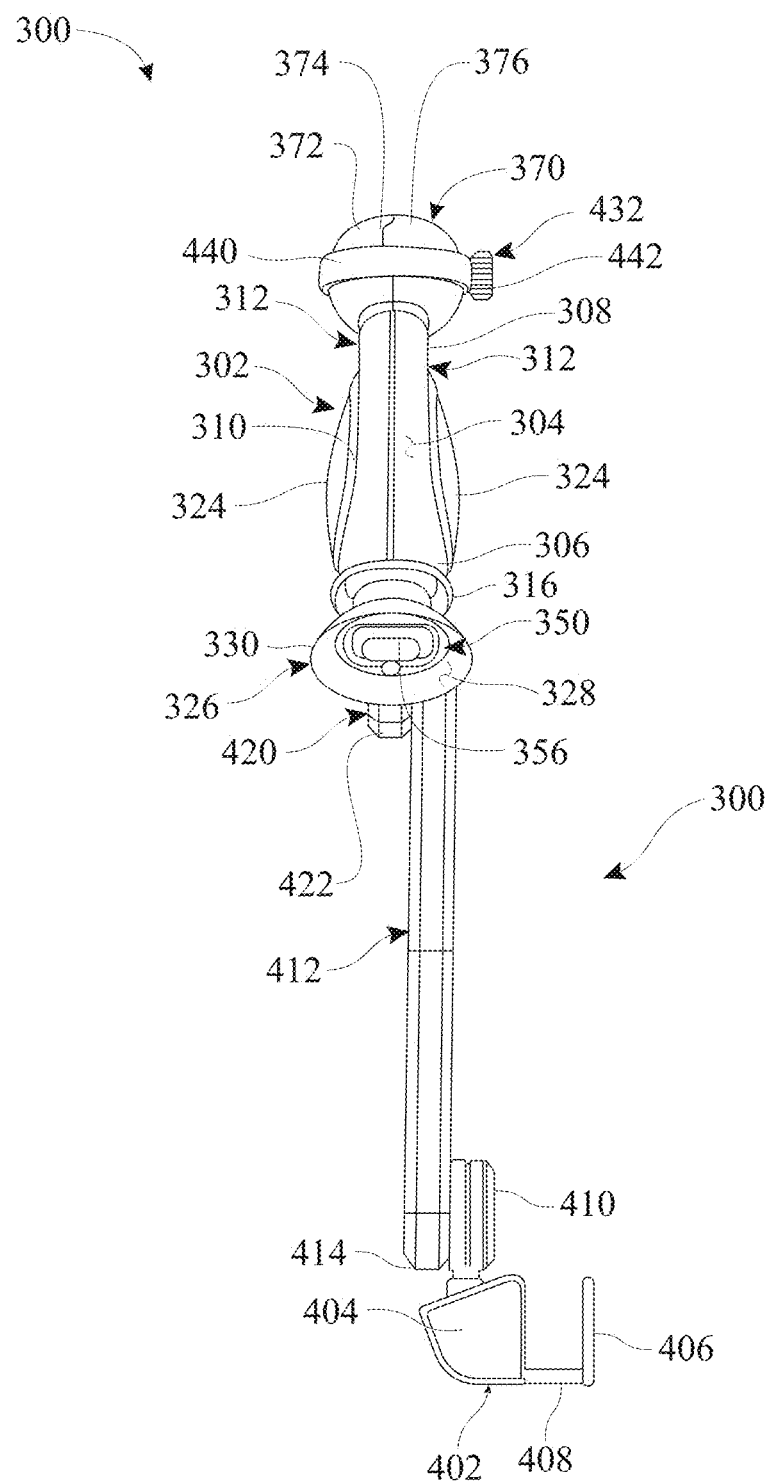
FIG. 17 presents a front view of the illustrative ultrasonic transducer probe holder and stand assembly illustrated in FIG. 16.
Figure 18:
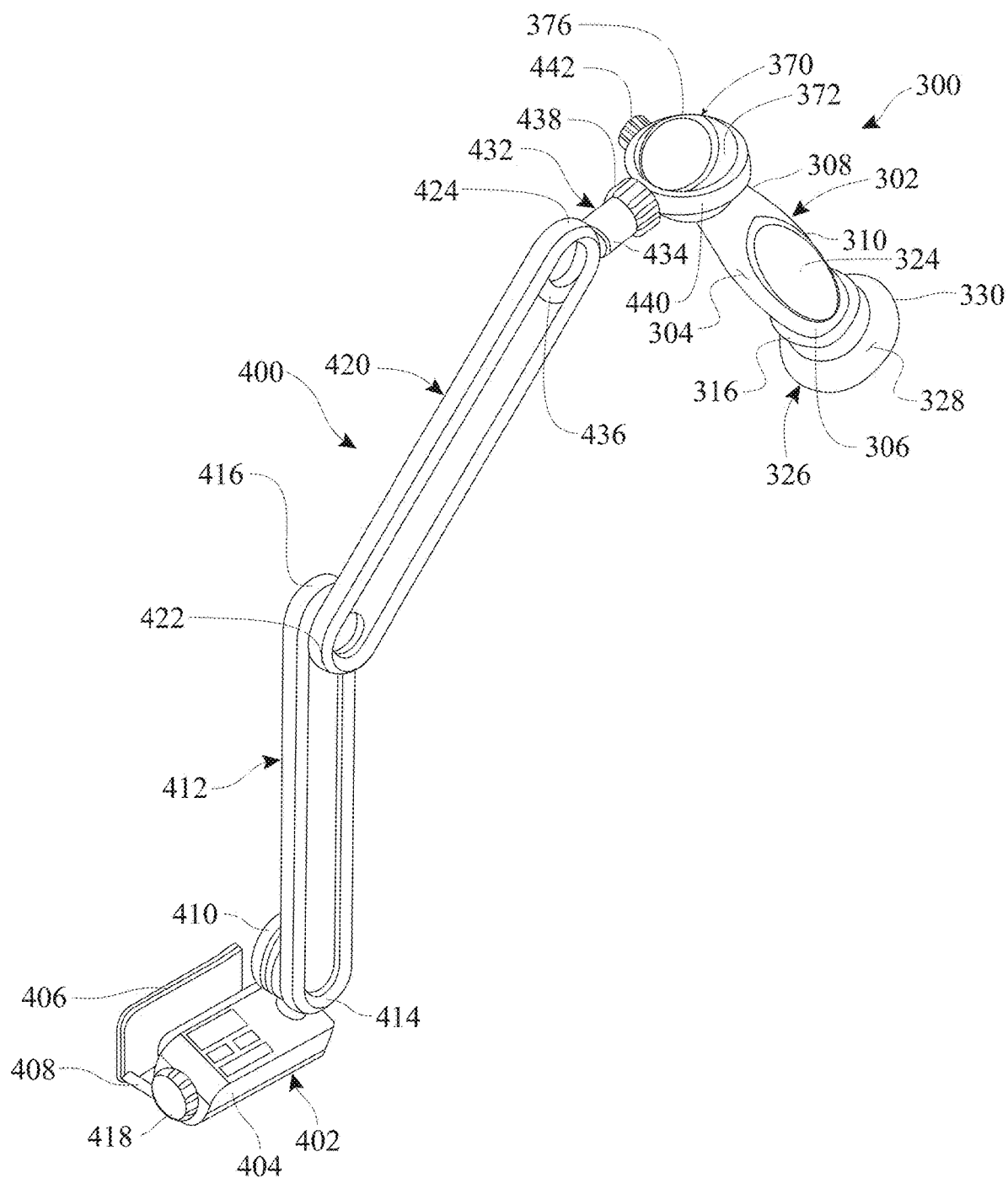
FIG. 18 presents a rear perspective view of the ultrasonic transducer probe holder illustrated in FIG. 16, with the stand assembly deployed in a raised position.
Figure 19:
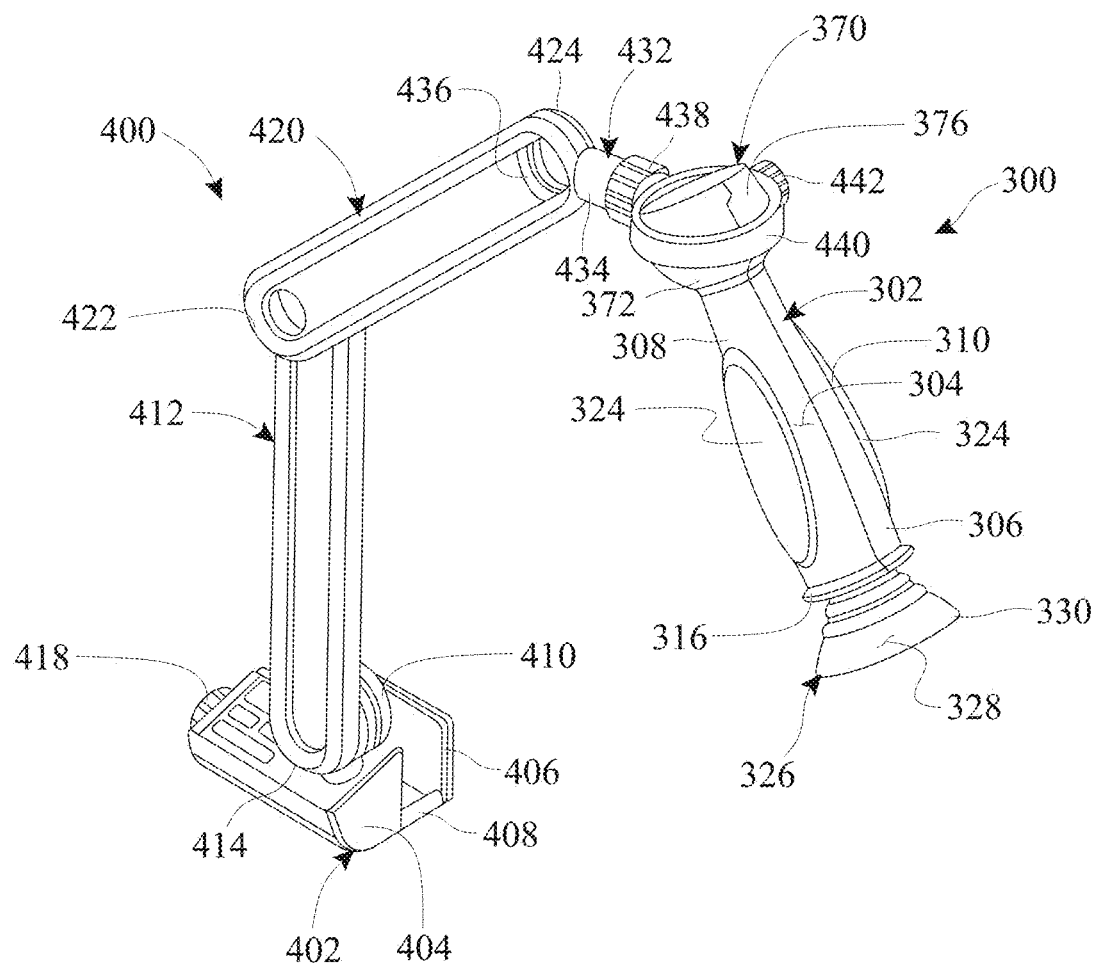
FIG. 19 presents a front perspective view of the ultrasonic transducer probe holder illustrated in FIG. 16, with the stand assembly of the probe holder deployed in a lowered position.
Figure 20:
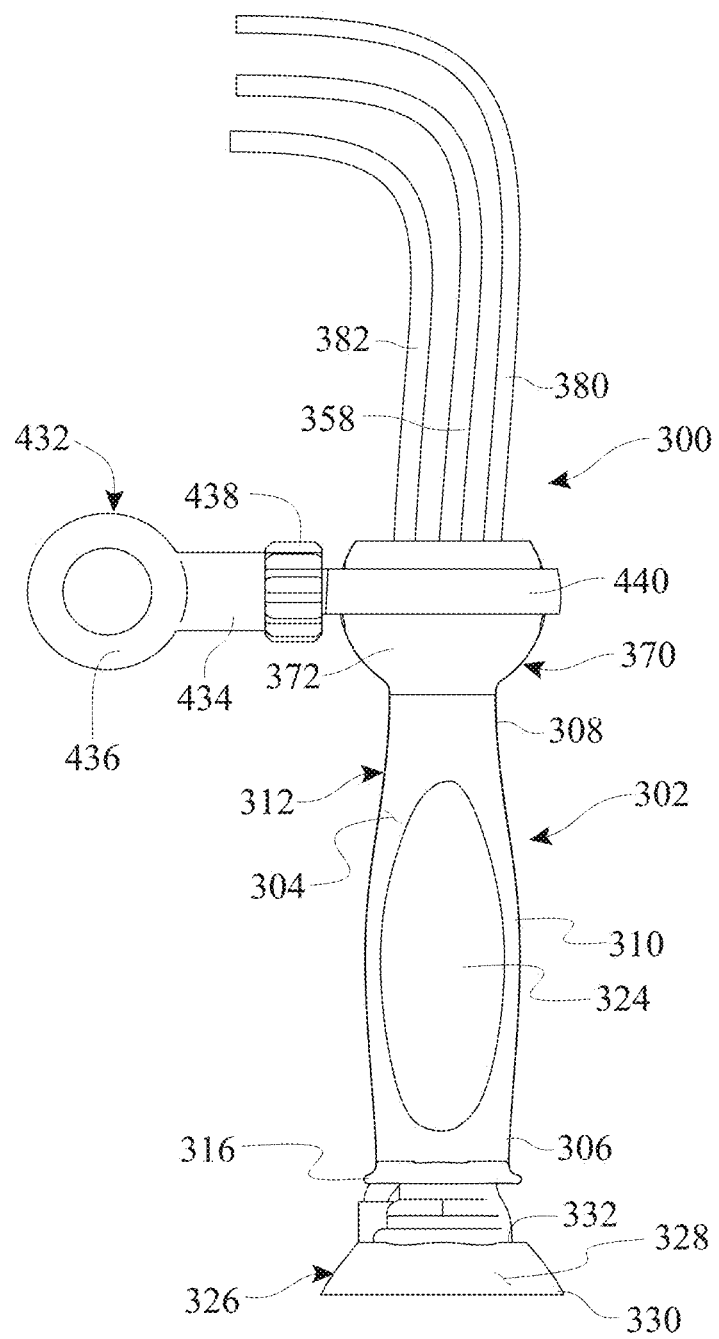
FIG. 20 presents a side view of the ultrasonic transducer probe holder illustrated in FIG. 16, detached from the stand assembly (not illustrated)
Figure 21:
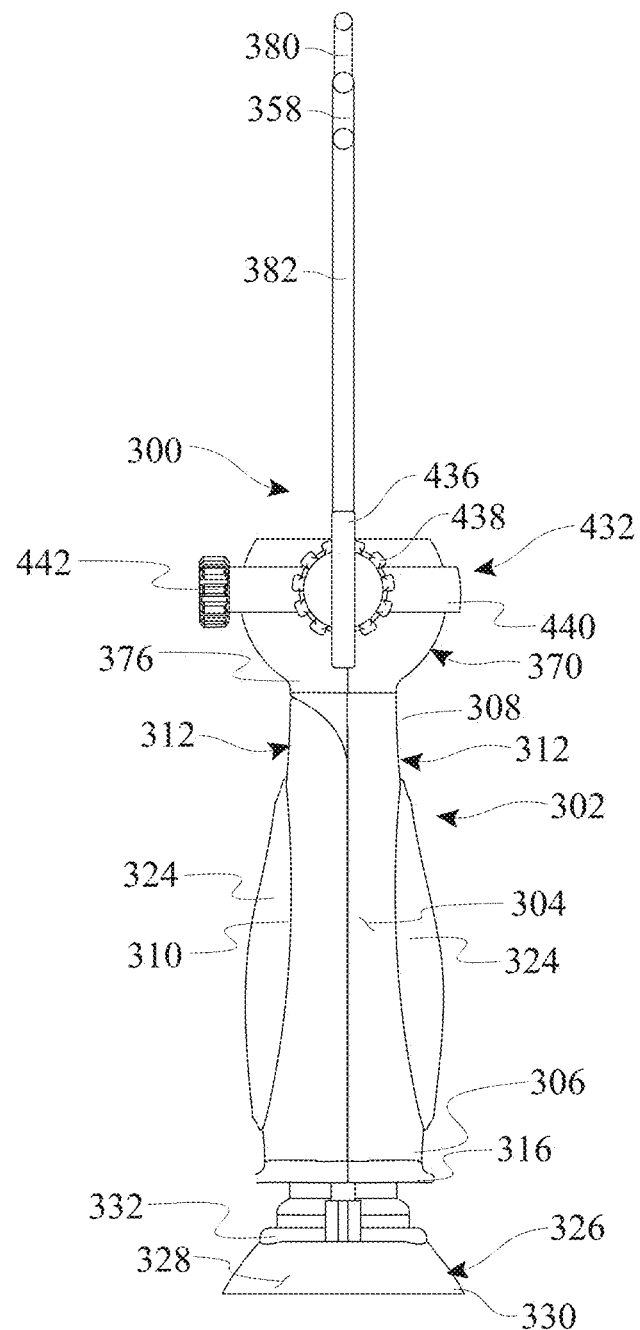
FIG. 21 presents a front view of the ultrasonic transducer probe holder illustrated in FIG. 20.
Figure 22:
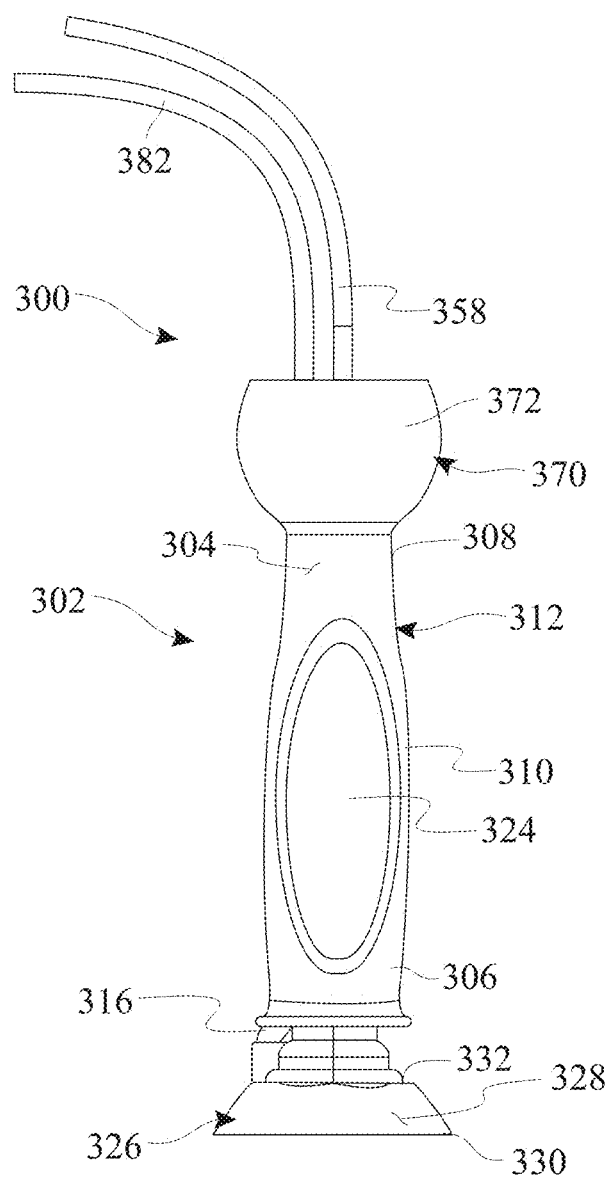
FIG. 22 presents a side view of the ultrasonic transducer probe holder, with a mount clevis (not illustrated) for the stand assembly detached from the probe holder.
Figure 23:
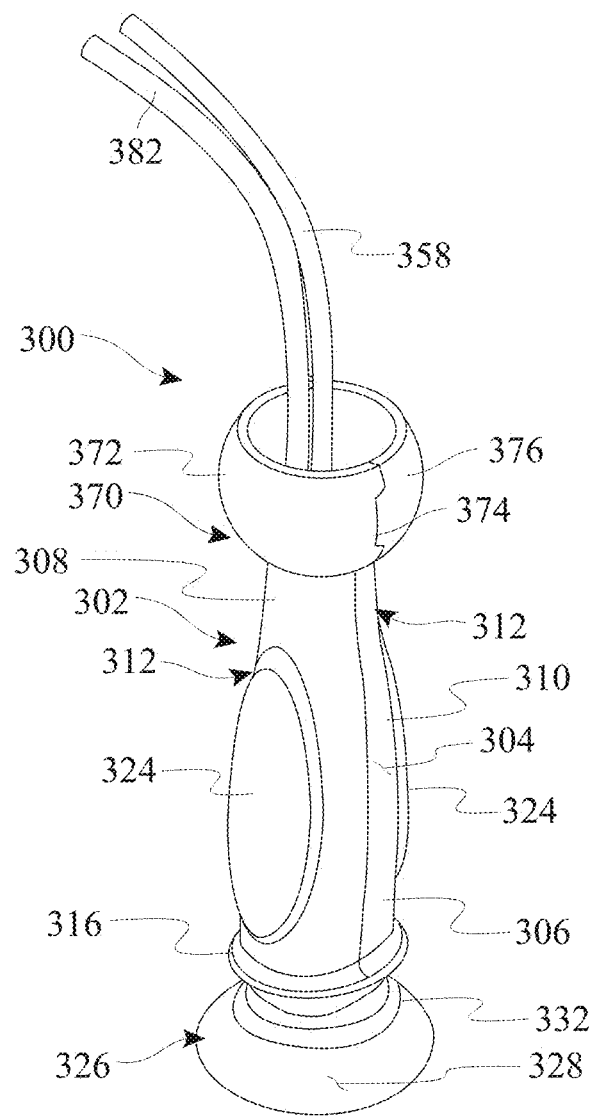
FIG. 23 presents a top perspective view of the ultrasonic transducer probe holder illustrated in FIG. 22.
Figure 24:
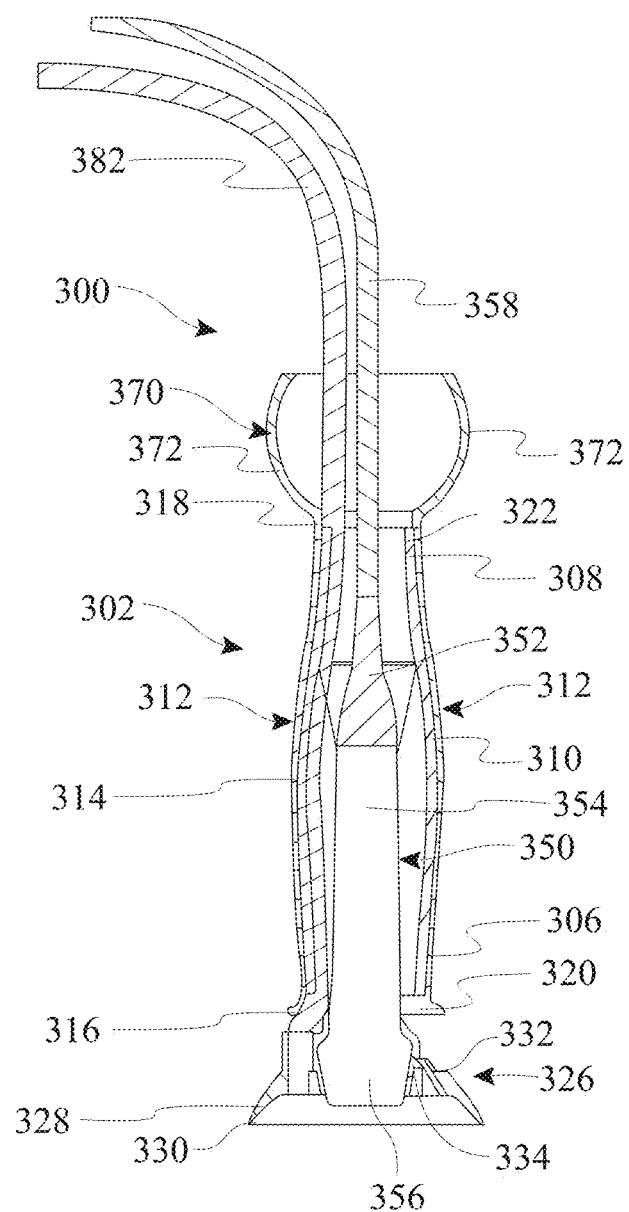
FIG. 24 presents a longitudinal sectional view, taken along section lines A-A in FIG. 25, of the ultrasonic transducer probe holder assembled on an ultrasonic transducer probe in typical application of the probe holder.
Figure 25:
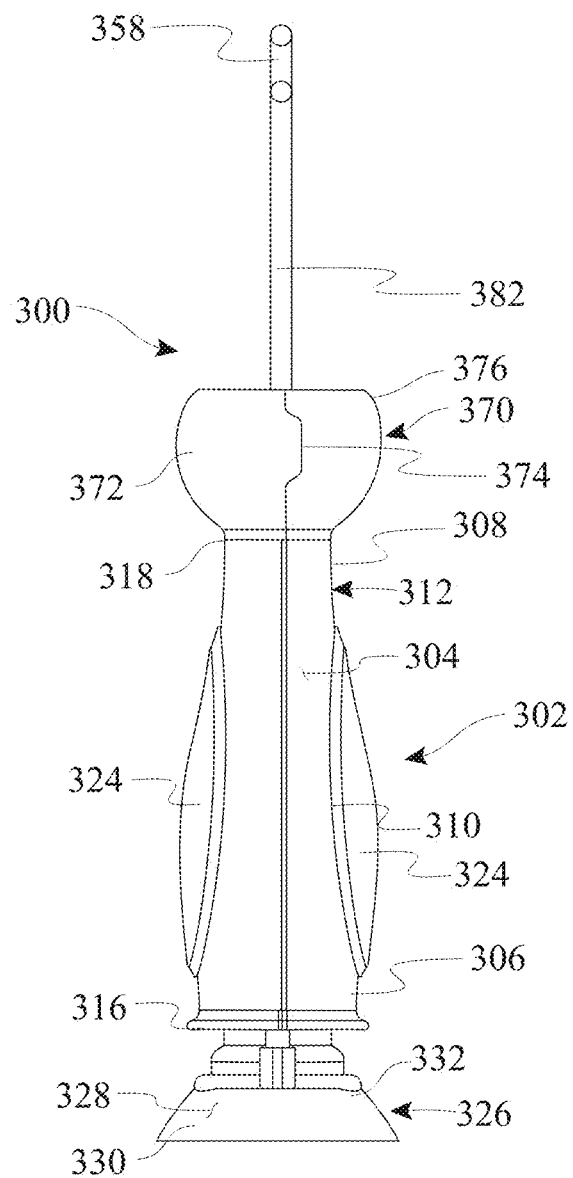
FIG. 25 presents a front view of the ultrasonic transducer probe holder illustrated in FIG. 24.
Figure 26:
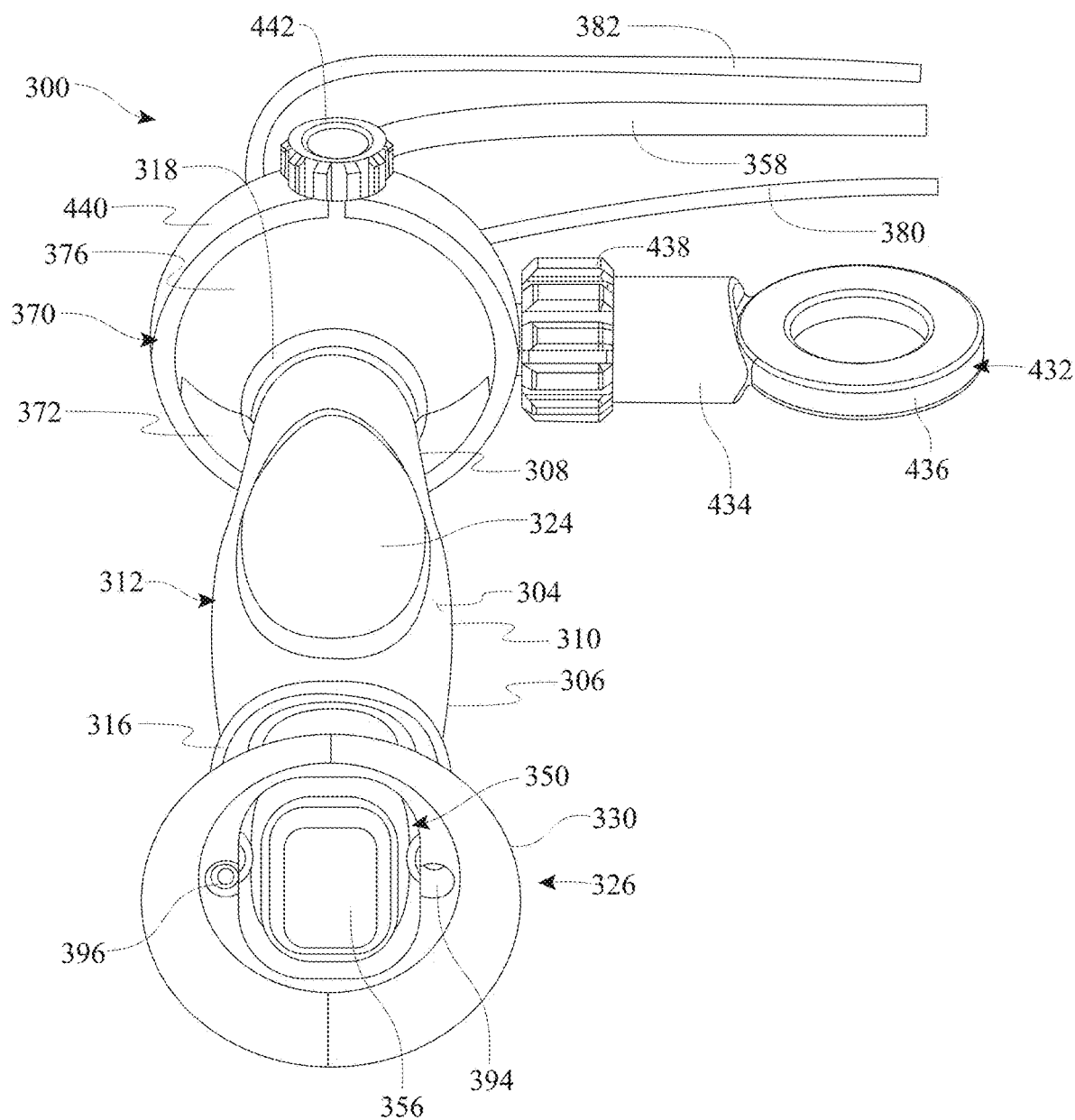
FIG. 26 presents a bottom perspective view of the ultrasonic transducer probe holder and ultrasonic transducer probe.
Figure 27:
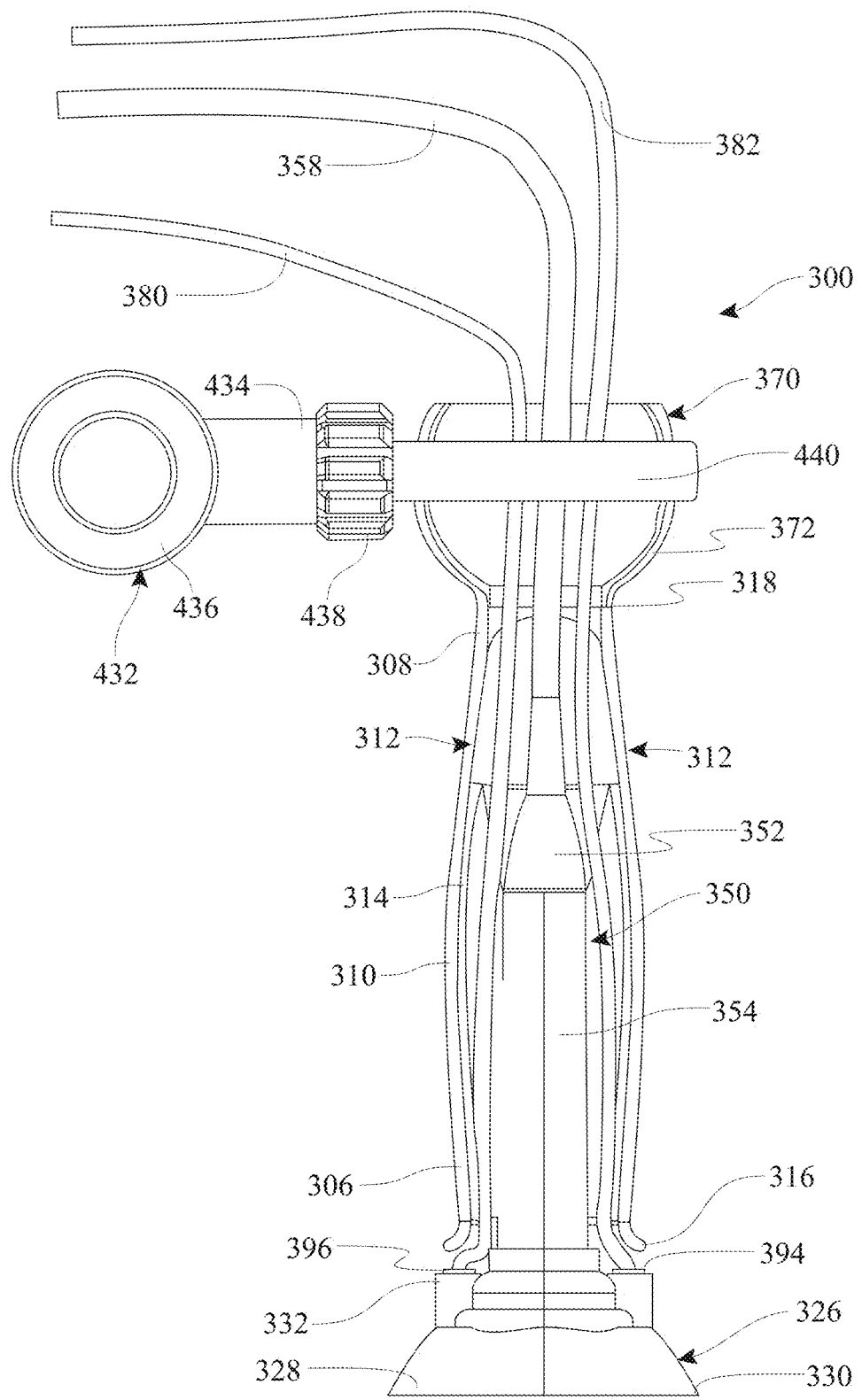
FIG. 27 presents a side view of the partially assembled ultrasonic transducer probe holder, with a grip portion section of the grip portion assembled in place on the ultrasonic transducer probe, more particularly illustrating a typical ball socket ring technique suitable for attaching the probe holder mount clevis to the ball socket of the probe holder.
Figure 28:
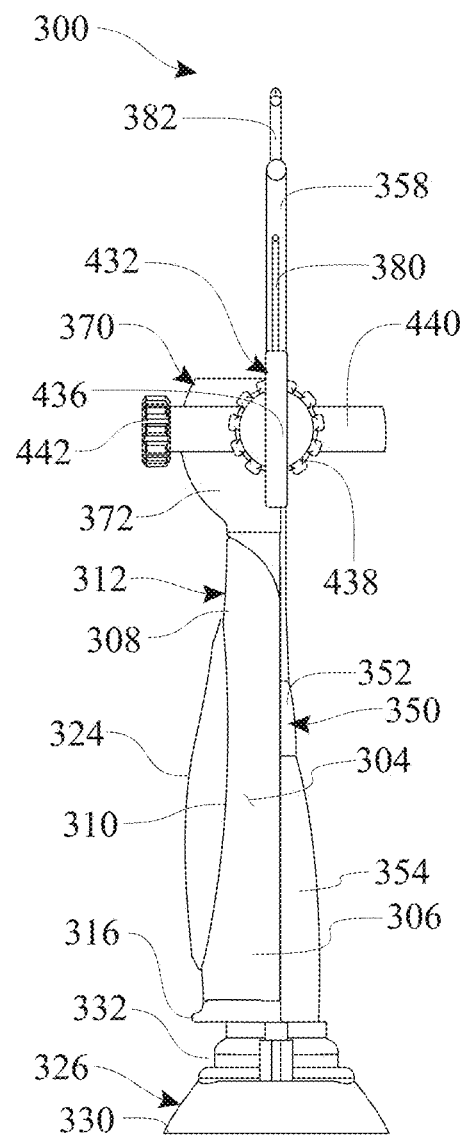
FIG. 28 presents a front view of the partially assembled ultrasonic transducer probe holder illustrated in FIG. 27.
Figure 29:
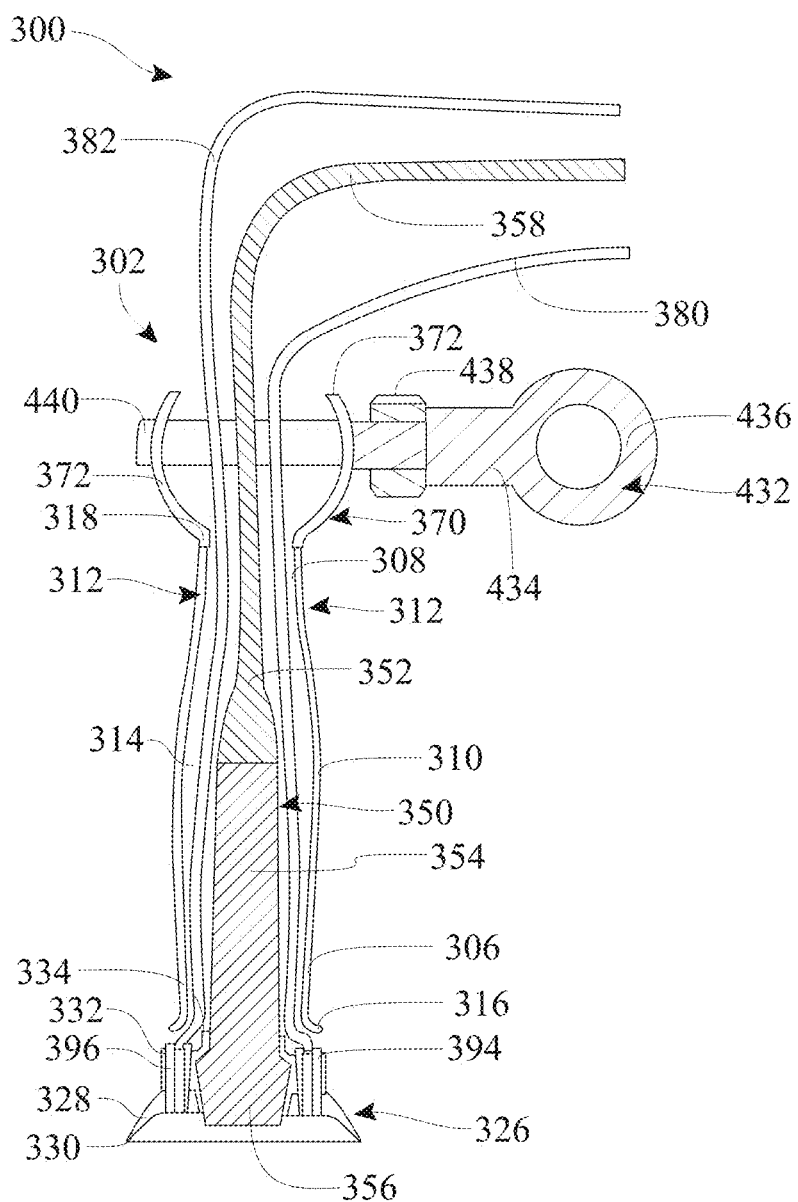
FIG. 29 presents a longitudinal sectional view, taken along section lines 29-29 in FIG. 28, of the ultrasonic transducer probe holder, assembled on the ultrasonic transducer probe, and the mount clevis attached to the ball socket of the probe holder.

As shown for instance in FIG. 3, the probe holder 100 may include a grip portion 102 and a skirt portion 126. The grip portion 102 may be configured for deployment on the ultrasonic transducer probe 150. The grip portion 102 may provide a comfortable and secure grip for an ultrasound technician (not illustrated) as the technician applies the ultrasonic transducer probe 150 against the skin 164 of the patient 162, as illustrated in FIGS. 14 and 15. The ultrasonic transducer probe 150 with the grip portion 102 thereon may be insertable in the skirt portion 126 of the probe holder 100, as illustrated in FIG. 3. The skirt portion 126 may be configured to hold or support the ultrasonic transducer probe 150 in an upward-standing position while forming a vacuum seal against the skin 164 of the patient 162. Accordingly, the skirt portion 126 may maintain the ultrasonic transducer probe 150 in place against the patient's skin 164 to reduce the manual pressure required for the technician to maintain the ultrasonic transducer probe 150 in place during an echocardiography or other procedure.

Figure 2:
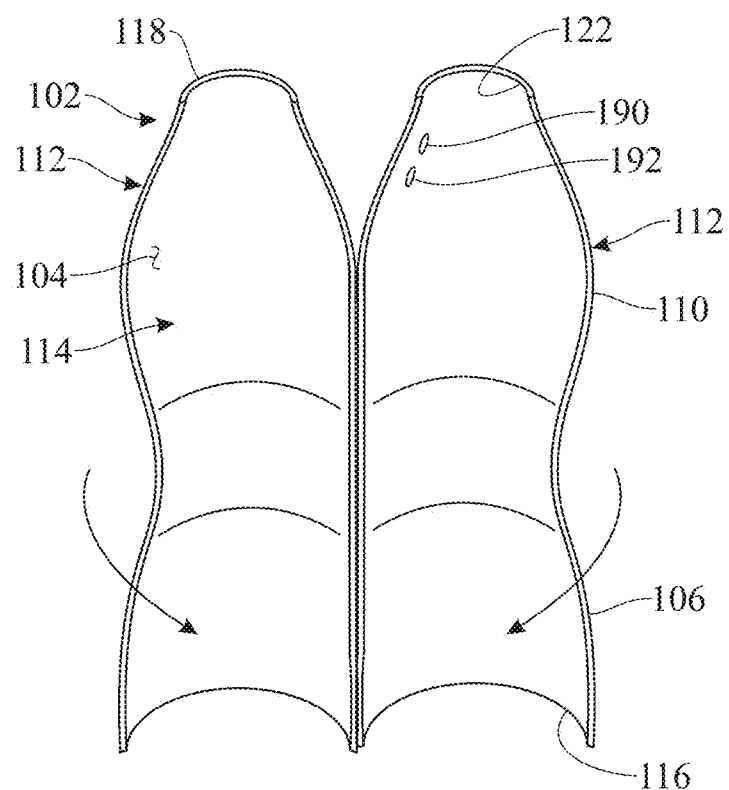
FIG. 2 presents an exploded perspective view of the illustrative ultrasonic transducer probe holder as the grip portion is being deployed in place on the ultrasonic transducer probe in typical application of the ultrasonic transducer probe holder.
Figure 2:
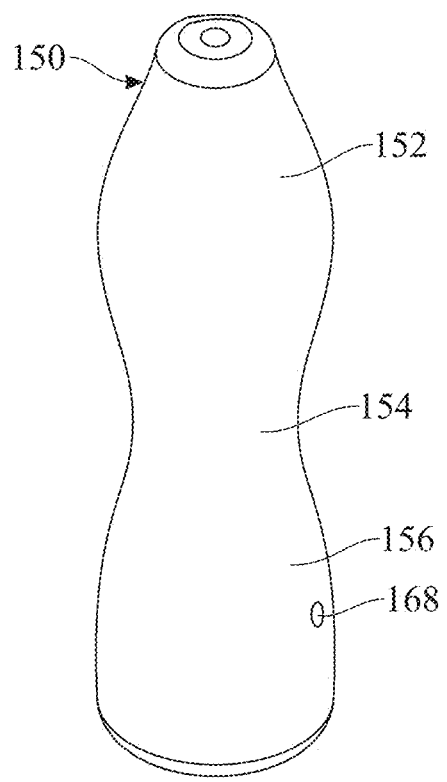

As illustrated in FIG. 2, in some applications, the ultrasonic transducer probe 150 of the medical ultrasound system may include a probe handle 152. A probe base 156 may extend from the probe handle 152. A colored, typically green light 168 may be provided on the ultrasonic transducer probe 150 such as to indicate the operational orientation of the probe 150. The grip portion 102 of the probe holder 100 may be configured for deployment around the probe handle 152 of the ultrasonic transducer probe 150. When the ultrasonic transducer probe 150 with the grip portion 102 thereon is inserted in the skirt portion 126, the skirt portion 126 may contain, enclose, or surround the probe base 156 of the ultrasonic transducer probe 150.

In some embodiments, the grip portion 102 of the probe holder 100 may include a grip portion wall 104. As illustrated in FIG. 14, a grip portion interior 114 may be formed by the grip portion wall 104. The grip portion interior 114 may be suitably sized and configured to contain the probe handle 152 of the ultrasonic transducer probe 150.

In some embodiments, the grip portion wall 104 of the grip portion 102 may include at least one elastic or stretchable material. Accordingly, the grip portion wall 104 may be configured to substantially conform to the diameter or width of the probe handle 152 of the ultrasonic transducer probe 150. As illustrated in FIG. 2, in some embodiments, the grip portion 102 may include a pair of mating or interfacing grip portion sections 112. The grip portion sections 112 may be configured to receive and contain opposite sides of the probe handle 152 of the ultrasonic transducer probe 150. In some embodiments, the grip portions 112 may have a hinged clamshell design, or may be configured to separately and detachably engage each other according to the knowledge of those skilled in the art.

In some embodiments, the at least one elastic or stretchable material of the grip portion wall 104 may include silicone, for example and without limitation. In other embodiments, the material may include stretchable plastic and/or rubber, for example and without limitation. In various applications, the ultrasonic transducer probe 150 may have different sizes, shapes and configurations. Accordingly, the typically elastic construction of the grip portion wall 104 may facilitate deployment of the grip portion 102 on ultrasonic transducer probes 150 having the different sizes, shapes and configurations. In some embodiments, the grip portion wall 104 of the grip portion 102 may be fabricated to match the specific size and configuration of the ultrasonic transducer probe 150.

As further illustrated in FIG. 2, in some applications of the probe holder 100, the ultrasonic transducer probe 150 may include a probe shaft 154 which connects the probe base 156 to the probe handle 152. The grip portion wall 104 of the grip portion 102 may include a grip portion base 106 which is configured to engage the probe shaft 154. A grip portion middle section 110 may extend from the grip portion base 106. A grip portion apex 108 may extend from the grip portion middle section 110. The grip portion middle section 110 and the grip portion apex 108 of the grip portion 102 may be configured to engage the probe handle 152 of the ultrasonic transducer probe 150.

In some applications, the probe handle 152 of the ultrasonic transducer probe 150 may have a greater diameter or width than that of the probe shaft 154 of the ultrasonic transducer probe 150. Thus, the grip portion middle section 110 of the grip portion wall 104 may be expandable to a greater diameter or width than that of the grip portion base 106 and the grip portion apex 108 of the grip portion wall 104 to accommodate the relatively greater diameter or width of the probe handle 152.

As illustrated in FIG. 14, a vacuum tube 180 and a gel tube 182 may be insertable into the ultrasonic transducer probe 150. The vacuum tube 180 may be connected to a vacuum system (not illustrated), The gel tube 182 may be connected to a pump and supply mechanism (not illustrated) which contains a conductive gel 160 (FIG. 15). The vacuum tube 180 may terminate in a vacuum tube end 184 in the ultrasonic transducer probe 150. As illustrated in FIG. 15, an open gel tube end 186 may terminate the gel tube 182 at the lower end of the probe base 156. Accordingly, vacuum pressure may be selectively applied to the ultrasonic transducer probe 150 through the vacuum tube 180. A selected quantity or volume of the conductive gel 160 may be dispensed from the probe base 156 of the ultrasonic transducer probe 150 through the gel tube 182 and the gel tube end 186, respectively.

In some embodiments, the grip portion base 106 of the grip portion wall 104 may have a grip portion base edge 116. A grip portion base opening 120 may be circumscribed by the grip portion base edge 116 of the grip portion base 106. The grip portion base opening 120 may communicate with the grip portion interior 114 of the grip portion 102. In placement of the ultrasonic transducer probe 150 in the skirt portion 126, as illustrated in FIG. 3, the grip portion base edge 116 of the grip portion wall 104 may be configured to engage the skirt portion 126.

The grip portion apex 108 of the grip portion wall 104 may have a grip portion apex edge 118 which is opposite the grip portion base edge 116 of the grip portion base 106. A grip portion apex opening 122 may be circumscribed by the grip portion apex edge 118 of the grip portion apex 108. The grip portion apex opening 122 may be sized and configured to facilitate passage of the probe cable 158 from the ultrasonic transducer probe 150 to the computer 172 of the medical ultrasound system 170.

As illustrated in FIGS. 2 and 14, a vacuum tube opening 190 may extend through the grip portion wall 104 at the grip portion apex 108 of the grip portion 102. The vacuum tube opening 190 may accommodate the vacuum tube 180 as the vacuum tube 180 extends from the vacuum system (not illustrated) to the ultrasonic transducer 150. A gel tube opening 192 may extend through the grip portion wall 104 at the grip portion apex 108. The gel tube opening 192 may accommodate the gel tube 182 as the gel tube 182 extends from the pump and supply mechanism (not illustrated) which contains the conductive gel 160 to the ultrasonic transducer 150.

The skirt portion 126 of the probe holder 100 may be generally funnel-shaped. In some embodiments, the skirt portion 126 may include a skirt portion wall 128. A skirt portion interior 142, where the vacuum is applied, may be formed by the skirt portion wall 128. The skirt portion interior 142 may be suitably sized and configured to contain the probe base 156 of the ultrasonic transducer probe 150.

Figure 5:
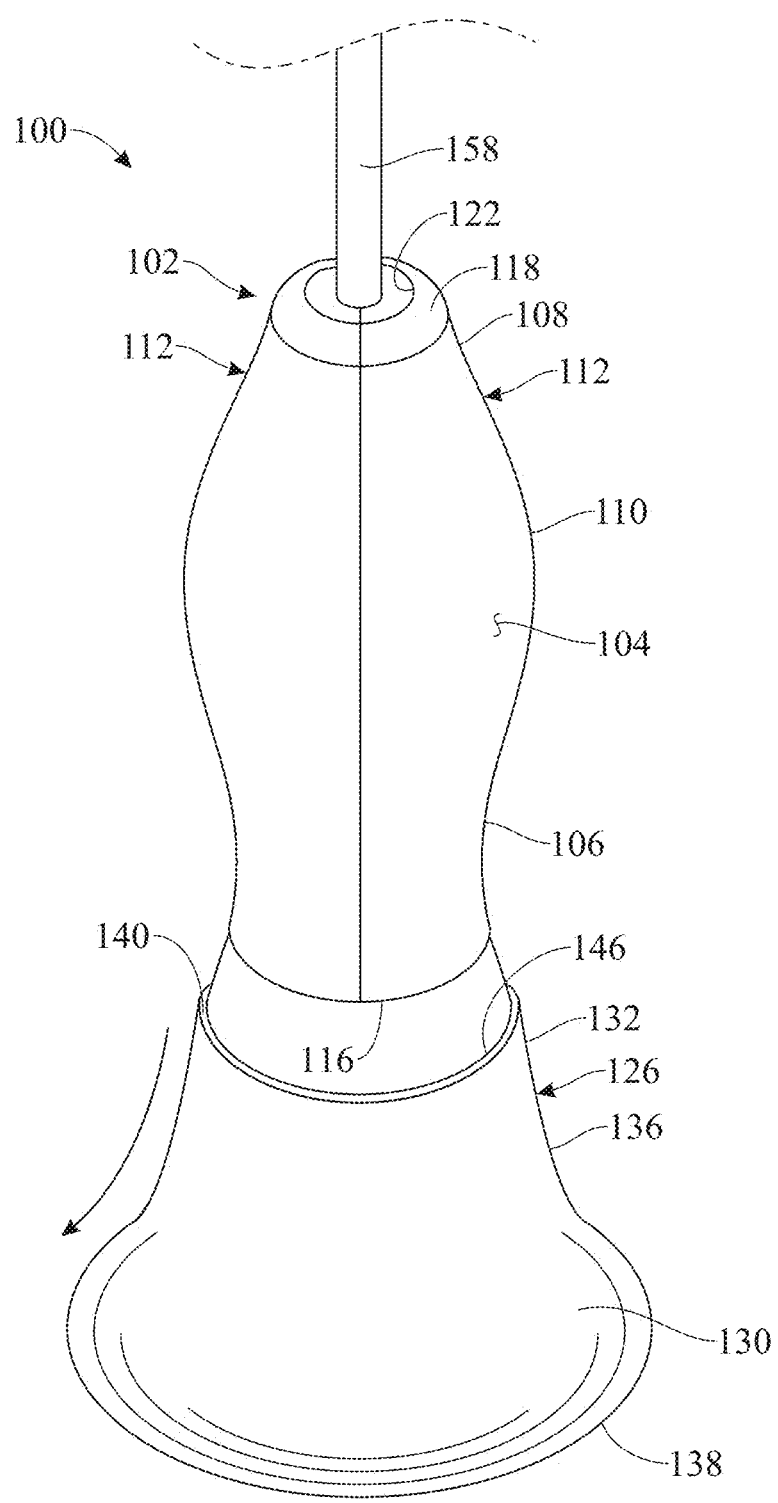
FIG. 5 presents a perspective view of the grip portion deployed on the ultrasonic transducer probe and the ultrasonic transducer probe placed in the skirt portion of the ultrasonic transducer probe holder and further illustrating typical downward application of the skirt portion against the skin of a patient in typical application of the ultrasonic transducer probe holder.

In some embodiments, the skirt portion wall 128 of the skirt portion 126 may include at least one elastic or stretchable material. For example and without limitation, in some embodiments, the at least one elastic or stretchable material of the skirt portion wall 128 may include silicone. In other embodiments, the material may include stretchable plastic and/or rubber, for example and without limitation. As illustrated in FIG. 5, when the ultrasonic transducer probe 150 is deployed in place in the skirt portion 126, the skirt portion wall 128 may flare or extend outwardly from the probe base 156 of the ultrasonic transducer probe 150.

In some embodiments, the skirt portion wall 128 of the skirt portion 126 may include a relatively wide skirt portion base 130. A relatively narrow skirt portion apex 132 may extend from the skirt portion base 130. As illustrated in FIG. 14, the skirt portion base 130 of the skirt portion 126 may have a skirt portion base opening 144 through which the probe base 156 may be exposed to facilitate contact of the probe base 156 with the skin 164 of the patient 162.

As further illustrated in FIG. 5, the skirt portion base 130 of the skirt portion wall 128 may include a skin engaging edge 138. The skin engaging edge 138 may circumscribe the skirt portion base opening 144 of the skirt portion base 130. The skin engaging edge 138 may be configured to engage the skin 164 of the patient 162 in typical application of the probe holder 100.

The skirt portion apex 132 of the of the skirt portion wall 128 may have a skirt portion apex opening 146. The skirt portion apex opening 146 may be configured to interface and communicate with the grip portion base opening 120 of the grip portion base 106 of the grip portion wall 104.

The skirt portion apex 132 of the skirt portion wall 128 may have a skirt portion apex edge 140 which circumscribes the skirt portion apex opening 146. The skirt portion apex edge 140 of the skirt portion apex 132 may be configured to engage or face the grip portion base edge 116 on the grip portion base 106 of the grip portion wall 104 in deployment of the skirt portion 126 on the ultrasonic transducer probe 150. Alternatively, in some embodiments, the skirt portion wall 128 of the skirt portion 126 may be fabricated in one piece or may be continuous with the grip portion wall 104 of the grip portion 102 according to the knowledge of those skilled in the art.

In some embodiments, the skirt portion wall 128 of the skirt portion 126 may have a skirt portion middle section 136 which extends between the skirt portion base 130 and the skirt portion apex 132. The skirt portion middle section 136 may gradually expand in width or diameter from the skirt portion apex 132 to the skirt portion base 130.

As illustrated in FIGS. 7-13 of the drawings, in some embodiments, a stand assembly 200 may be configured to hold or support the probe holder 100 as the probe holder 100 remains deployed on the ultrasonic transducer probe 150. The stand assembly 200 may support the ultrasonic transducer probe 150 as the ultrasonic transducer probe 150 is applied to the skin 164 of the patient 162. The stand assembly 200 may include a stand base 202. A cradle base 220 may be supported by the stand base 202. An elongated cradle gooseneck 224 may extend from the cradle base 220. A cradle 226 may be supported by the cradle gooseneck 224. As illustrated in FIG. 11, the cradle 226 may be suitably sized and configured to support the ultrasonic transducer probe 150 with the probe holder 100 in various positions on the patient as selected by the sonographer.

As illustrated in FIG. 12, the stand base 202 may be configured to engage a support 248 for support thereby throughout use of the ultrasonic transducer probe 150. For example and without limitation, in some embodiments, the support 248 may include a frame or other structural component on a bed or table on which the patient 162 reclines. In some embodiments, the stand base 202 may have a lower base member 204. At least one base arm 208 may extend from the lower base member 204. An upper base member 206 may be supported by the base arm 208. The cradle base 220 may be supported by the upper base member 206 of the stand base 202. The stand base 202 may be configured to receive the support 248 between the lower base member 204 and the upper base member 206.

Figure 10:
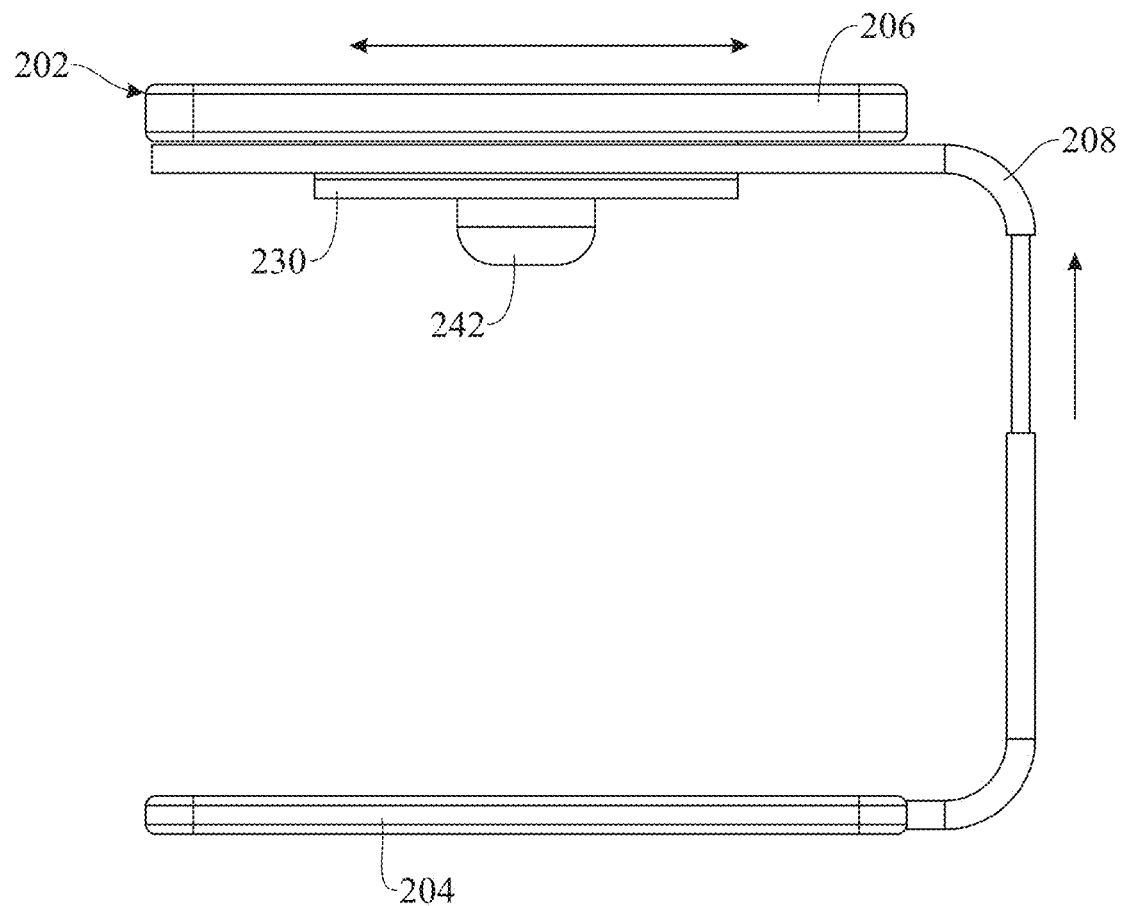
FIG. 10 presents a side view of a typical stand base of the stand assembly, more particularly vertical and horizontal adjustment capability of the stand base.

As illustrated in FIG. 10, in some embodiments, the position of the upper base member 206 may be selectively adjustable with respect to the lower base member 204 of the stand base 202 according to the knowledge of those skilled in the art. For example and without limitation, in some embodiments, the base arms 208 may be telescopically adjustable for the purpose. Accordingly, as illustrated in FIG. 12, the stand base 202 may be configured to accommodate supports 248 having different thicknesses between the lower base member 204 and the upper base member 206 by adjustment of the upper base member 206 with respect to the lower base member 204.

Figure 7:
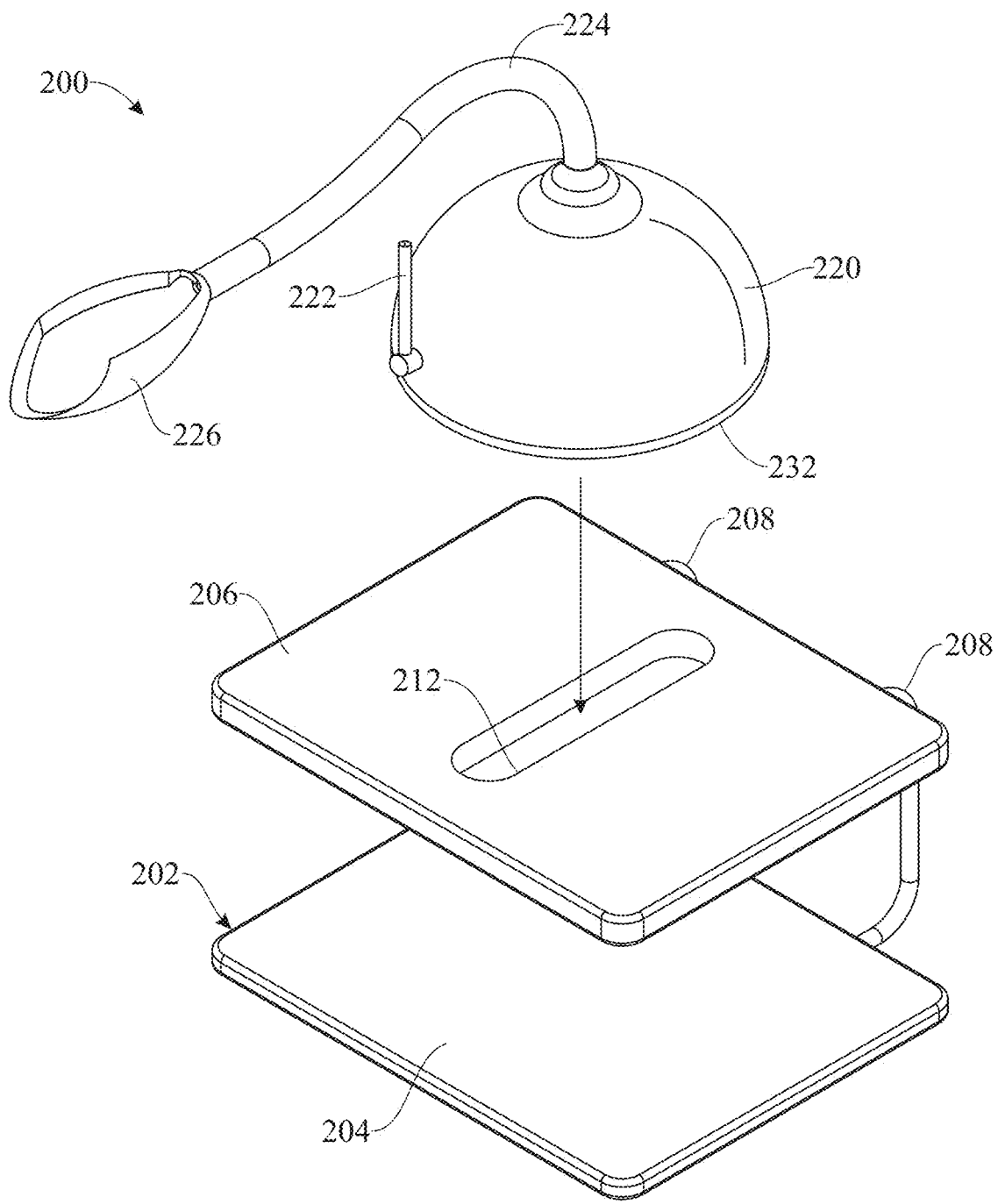
FIG. 7 presents an exploded top perspective view of a typical stand assembly configured to hold or support the probe holder as the probe holder remains deployed on the ultrasonic transducer probe.
Figure 8:
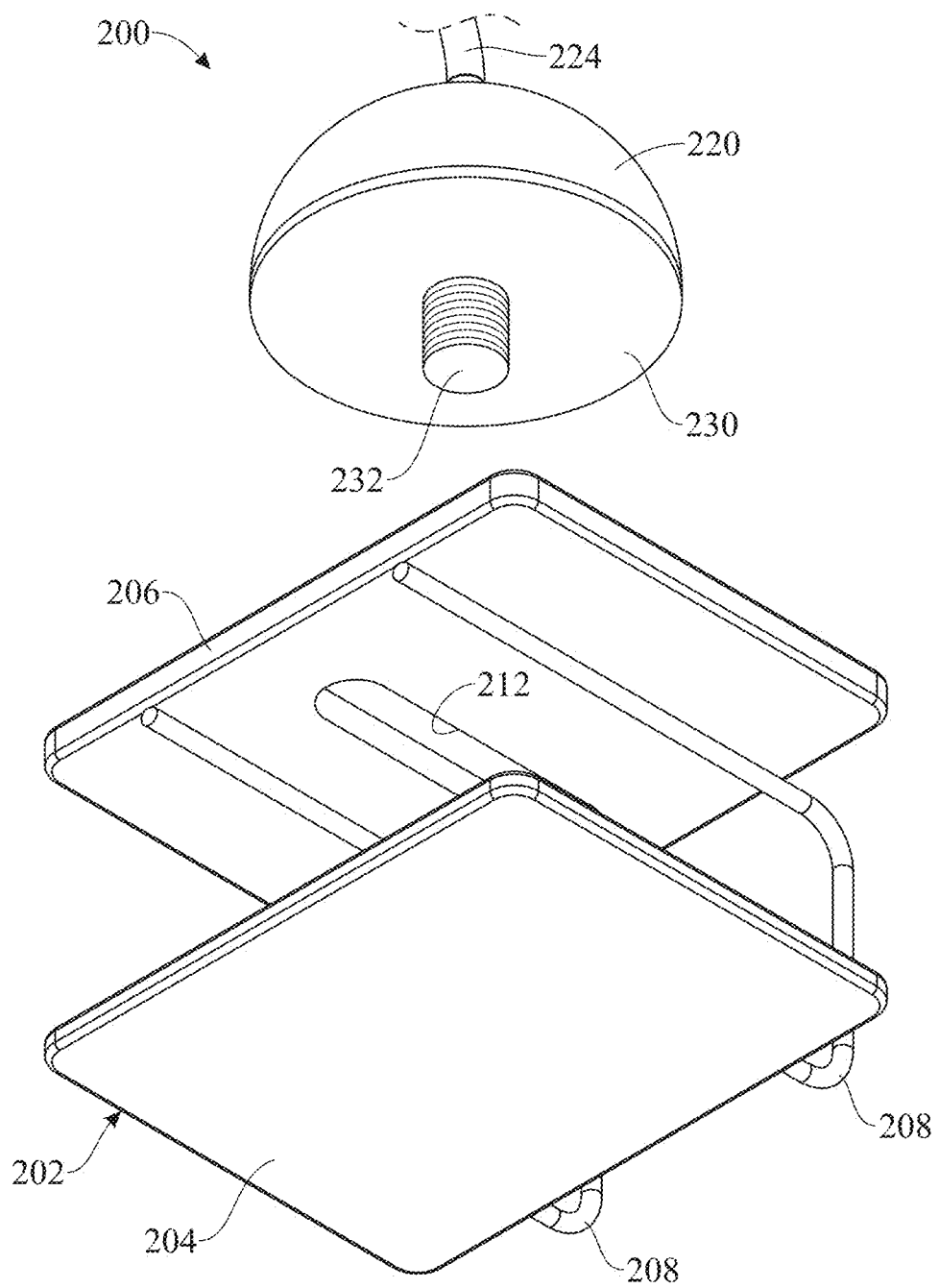
FIG. 8 presents an exploded bottom perspective view of the stand assembly.
Figure 9:
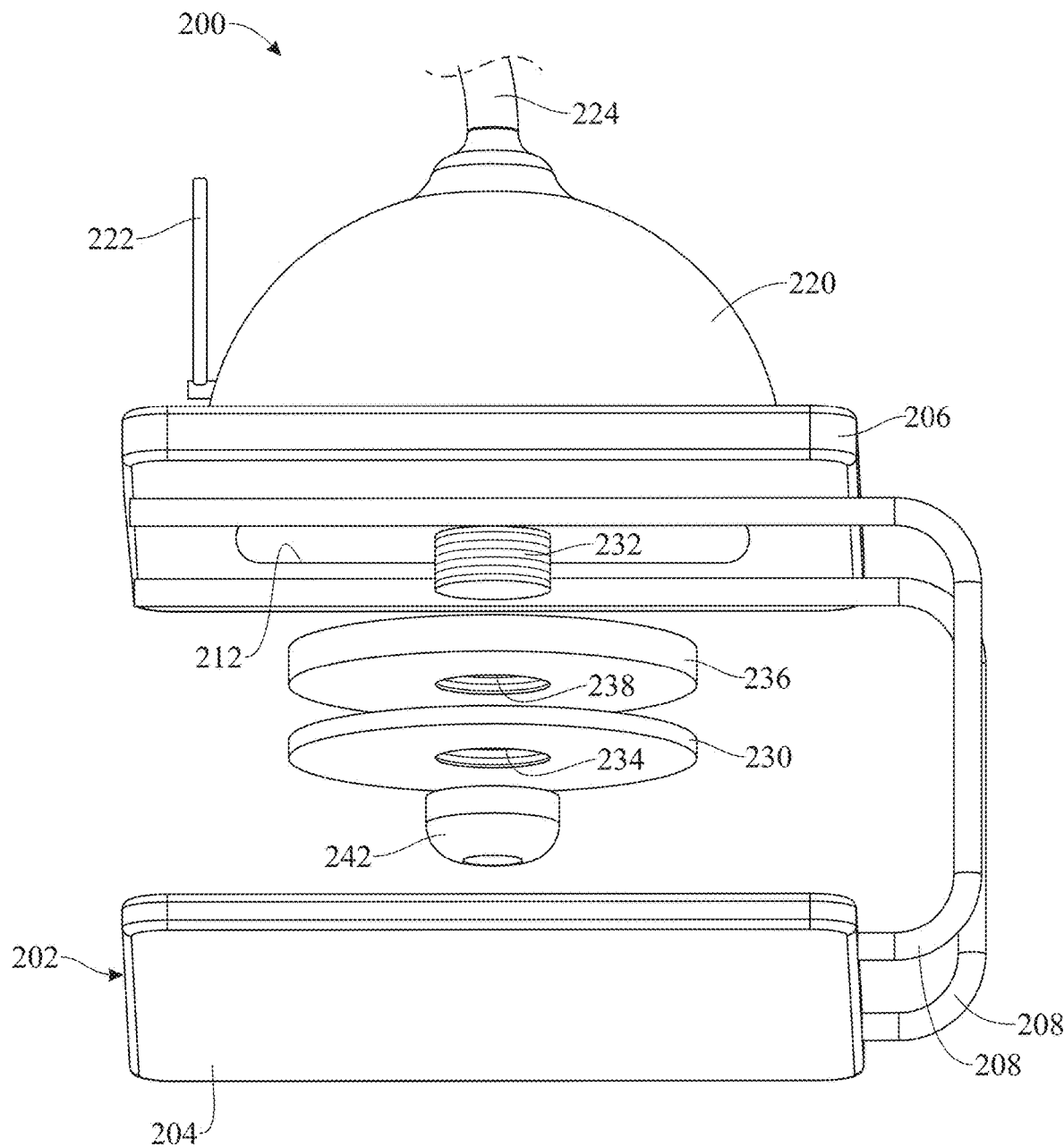
FIG. 9 presents an exploded side perspective view of the stand assembly, more particularly illustrating a typical technique for attaching the cradle base to the stand base of the stand assembly.

In some embodiments, the cradle base 220 may be adjustably mounted with respect to the upper base member 206 of the stand base 202. Accordingly, as illustrated in FIG. 7, in some embodiments, an elongated base slot 212 may extend through the upper base member 206 of the stand base 202. The cradle base 220 may adjustably engage the base slot 212. As illustrated in FIGS. 8 and 9, in some embodiments, a threaded cradle nipple 232 may extend downwardly from the cradle base 220. The cradle nipple 232 may extend downwardly through the base slot 212. As illustrated in FIG. 9, a cradle base plate 230 may have a central plate opening 234 which receives the cradle nipple 232. The cradle base plate 230 may be deployed on the cradle nipple 232 beneath the upper base member 206. In some embodiments, a cradle disk 236, having a central disk opening 238 and fabricated of rubber or other resilient material, may be placed on the cradle nipple 232 between the cradle base plate 230 and the cradle base 220. A cradle cap 242 may be threaded and tightened on the extending portion of the cradle nipple 232 to secure the cradle base 220 against the upper surface of the upper base member 206. Accordingly, the cradle cap 242 may be selectively loosened on the cradle nipple 232 to facilitate movement of the cradle base 220 with respect to the upper base member 206 as the cradle nipple 232 traverses the base slot 212. The cradle cap 242 may be subsequently tightened on the cradle nipple 232 to immobilize the cradle base 220 at the selected position on the upper base member 206.

In some embodiments, a cradle base lock lever 222 may be provided on the cradle base 220. The cradle base lock lever 222 may be selectively deployable in an unlock position (FIG. 9) and a lock position (FIGS. 11 and 12). The cradle base lock lever 222 may operably engage the cradle nipple 232 to facilitate selective advancement (in the unlock position) and retraction (in the lock position) of the cradle nipple 232 with respect to the cradle base 220 responsive to positional manipulation of the cradle base lock lever 222, according to the knowledge of those skilled in the art. Accordingly, movement of the cradle base 220 with respect to the upper base member 206 may be accomplished by manipulation of the cradle base lock lever 222 to the unlock position Securement of the cradle base 220 at the selected position on the upper base member 206 may be accomplished by manipulation of the cradle base lock lever 222 from the unlock position to the lock position.

Figure 13:
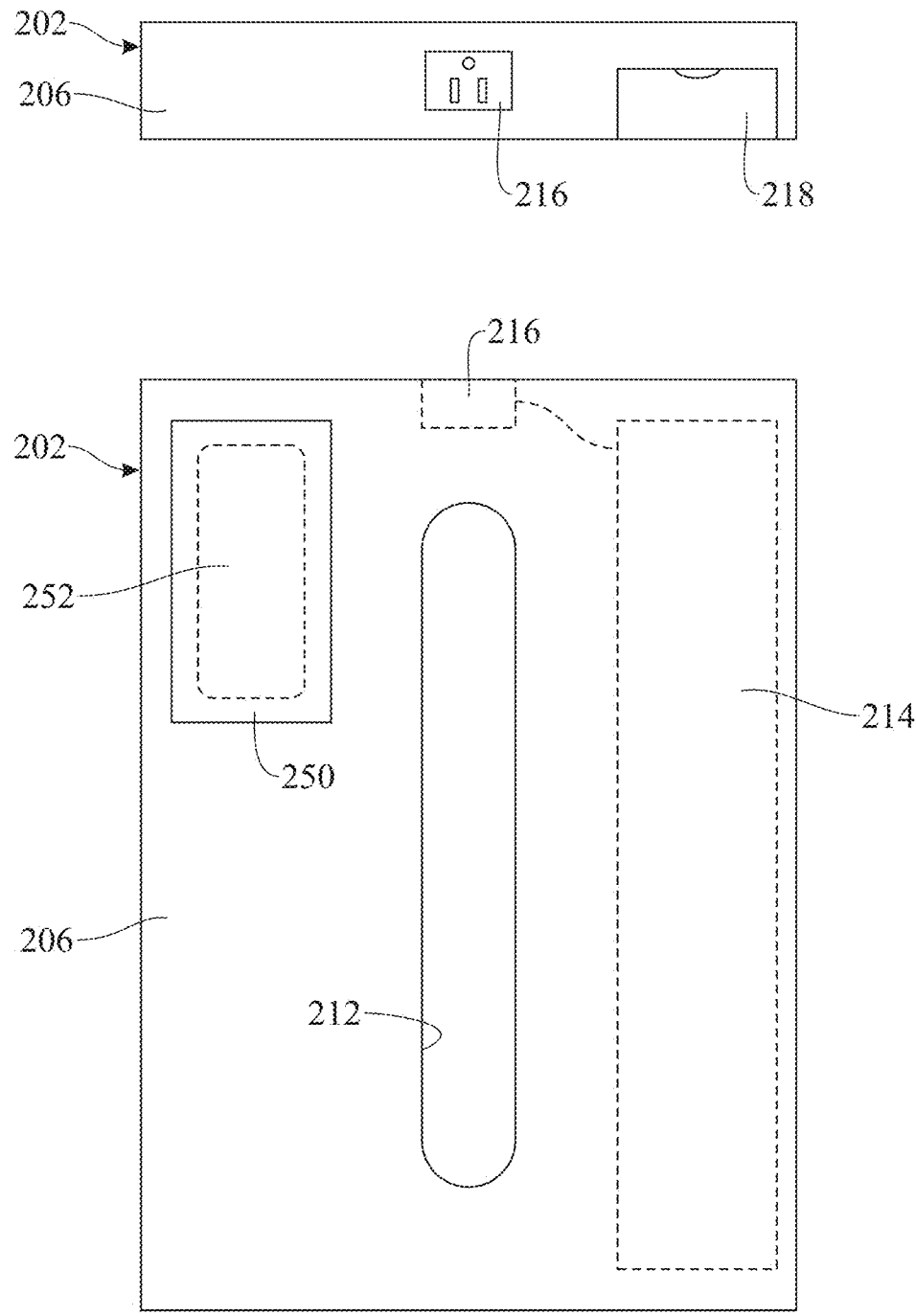
FIG. 13 presents a side view (top image) and a top view (bottom image) of the upper base member of the stand base, more particularly illustrating a battery compartment in the upper base member, a battery in the battery compartment and an electrical outlet electrically interfacing with the battery compartment.

As illustrated in FIG. 13, in some embodiments, the upper base member 206 of the stand base 202 may include at least one electrical outlet 216. The electrical outlet 216 may be provided along an edge, as illustrated, or in any other accessible position of the upper base member 206. A battery compartment 218 may be provided in the upper base member 206. The battery compartment 218 may electrically interface with the electrical outlet 216. The battery compartment 218 may be sized and configured to contain at least one battery 214 which supplies electrical current to the electrical outlet 216. Accordingly, the electrical outlet 216 may provide electrical current to the ultrasonic transducer probe 150 and/or to one or more electrical accessories during use of the ultrasonic transducer probe 150.

As further illustrated in FIG. 13, in some embodiments, at least one gel container storage compartment 250 may be provided in the upper base member 206, as illustrated, and/or in the lower base member 204 of the stand base 202. The gel container storage compartment 250 may be suitably sized and configured to contain at least one gel container 1 which contains a supply of the conductive gel 160.

Figure 6:
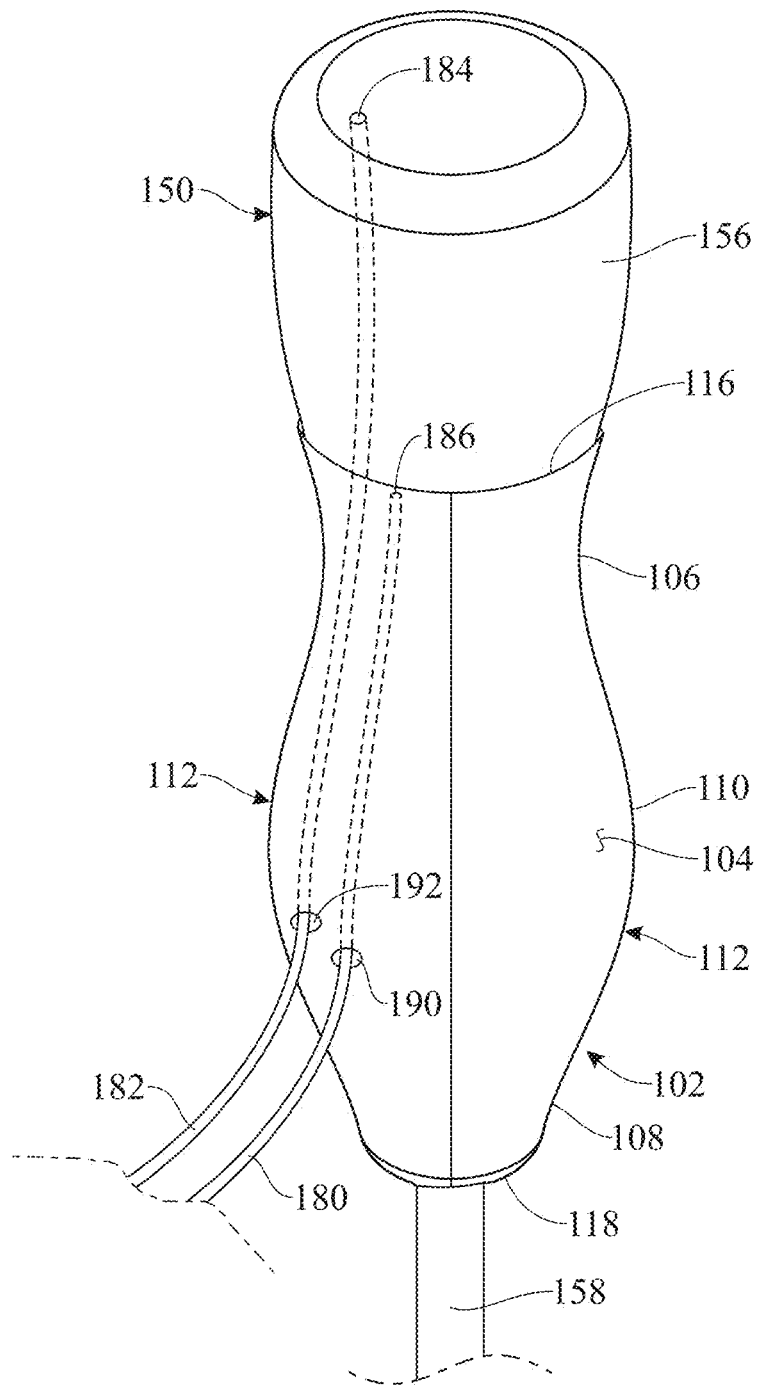
FIG. 6 presents a bottom perspective view of the grip portion of the ultrasonic transducer probe holder deployed on the ultrasonic transducer probe, more particularly illustrating a vacuum tube opening and a gel tube opening in the grip portion and a vacuum tube and a gel tube extending through the respective vacuum tube opening and gel tube opening in typical application of the ultrasonic transducer probe holder.

As illustrated in FIGS. 1-6, 14 and 15, in typical application of the probe holder 100, the grip portion 102 may initially be deployed in place on the probe handle 152 and the probe shaft 154 of the ultrasonic transducer probe 150. Accordingly, the grip portion inner wall 104 may be stretched over the ultrasonic transducer probe 150 as the probe base 156 and then the probe shaft 154 and the probe handle 152, respectively, are inserted through the grip portion base opening 120 in the grip portion base 106. The grip portion wall 104 may then be released to recoil snugly against the probe handle 152 and the probe shaft 154. As illustrated in FIG. 2, in some applications, the grip portion 102 may be deployed by placing the grip portion sections 112 around the respective sides of the ultrasonic transducer probe 150 and attaching the grip portions 112 to each other. As illustrated in FIGS. 6, the vacuum tube 180 and the gel tube 182 may be inserted through the respective vacuum tube opening 190 and gel tube opening 192 in the grip portion apex 108 of the grip portion 102. The vacuum tube 180 may be connected to the vacuum system (not illustrated). The gel tube 182 may be connected to the pump and supply mechanism (not illustrated) which contains a supply of the conductive gel 160 (FIG. 15). The probe cable 158 which connects the ultrasonic transducer probe 150 to the computer of the medical ultrasound system may extend through the grip portion apex opening 122 at the grip portion apex edge 118 of the grip portion apex 108.

Figure 4:
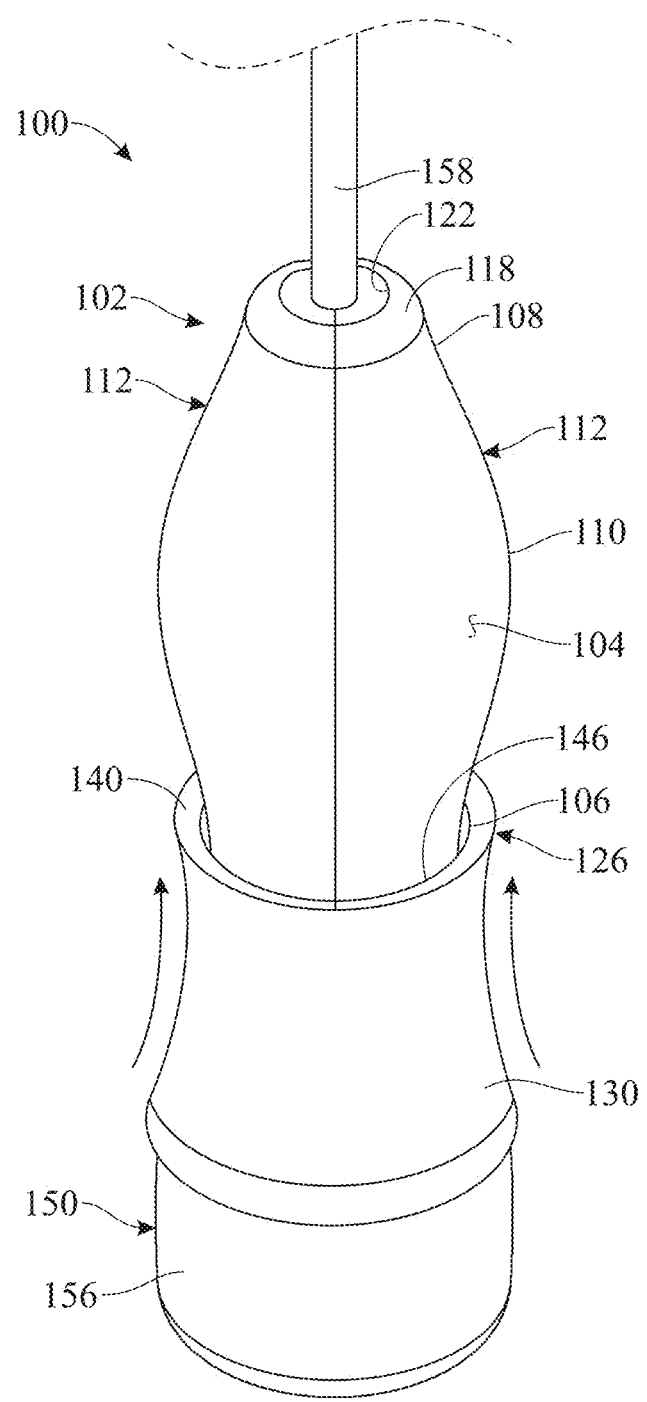
FIG. 4 presents a perspective view illustrating typical sliding deployment of the skirt portion on the ultrasonic transducer probe.

As illustrated in FIG. 4, the skirt portion 126 may be deployed in place on the ultrasonic transducer probe 150 beneath or adjacent to the grip portion 102. Accordingly, the skirt portion 126 may be stretched and initially slid over and then released against the probe base 156 of the ultrasonic transducer probe 150. As illustrated in FIGS. 11 and 12, the ultrasonic transducer probe 150 with the probe holder 100 thereon may be placed in the cradle 226 of the stand assembly 200. The position of the cradle 226 may be selected by adjustment of the lower base member 204 and tipper base member 206 of stand base 202 with respect to each other (FIG. 10), horizontal adjustment of the cradle base 202 with respect to the upper base member 206 (FIG. 10) and universal adjustment of the cradle gooseneck 224.

The patient 162 may recline on the bed, table, or other support 248 (FIG. 12) on which the stand assembly 200 is deployed. The ultrasound technician may grasp the grip portion 102 of the probe holder 100 as the probe holder 100 remains in place in the cradle 226 of the stand assembly 200. As the ultrasound technician locates a position on the skin 164 of the patient 162 and releases the probe holder 100, the cradle gooseneck 224 may enable the probe base 156 to remain in position. As illustrated in FIGS. 14 and 15, the skin engaging edge 138 on the skirt portion base 130 of the skirt portion 126 may next be placed against the skin 164 of the patient 162 at the selected position on the skin 164. For example and without limitation, in an echocardiography procedure, the skirt portion 126 may be placed on the torso of the patient 162 as the patient 162 lies in a supine position on the support 248. As illustrated by the arrow in FIG. 5, the technician may initially manually apply downward force on the grip portion 102 such that an airtight suction seal is formed between the skin engaging edge 138 of the skirt portion base 130 and the surface of the patient's skin 164. The technician may then release the grip portion 102 as cradle 226 on the cradle gooseneck 224 continues to support the probe holder 100 and the ultrasonic transducer probe 150 held therein typically in an upward-standing position on the skin 164 of the patient 162.

As the ultrasonic transducer probe 150 remains suspended by the cradle 226 of the stand assembly 200 without touch by the ultrasound technician, removal of the hand of the technician from the probe holder 100 typically activates the vacuum system connected to the ultrasonic transducer probe 150 through the vacuum tube 180. The vacuum system may generate closer and tighter approximation of the probe base 156 to the skin 164 of the patient 162, thereby simulating direct pressure of the probe base 156 into the chest of the patient 162 that would otherwise be applied by the hand of the technician. This hands-free mechanism of operating the ultrasonic transducer probe 150 will greatly reduce the musculoskeletal trauma so prevalent among ultrasound technicians today.

As illustrated in FIG. 15, the conductive gel 160 may be dispensed through the gel tube 182 from the open gel tube end 186 at the lower end of the probe base 156 and onto the patient's skin 164. The probe base 156 of the ultrasonic transducer probe 150 may generate sonic waves which impinge against and through the skin 164 of the patient 162 and receive the reflected sonic waves which echo from the organ or tissue being imaged. The computer may generate 2D or 3D images of the imaged organ or tissue of the patient 162 on the display, typically in the conventional manner, for diagnostic purposes. As illustrated in FIGS. 11 and 12, when not in use, the ultrasonic transducer probe 150 with the probe holder 100 thereon may remain in place in the cradle 226 of the stand assembly 200.

It will be appreciated by those skilled in the art that, by enabling the ultrasound technician to manually release the ultrasonic transducer probe 150 during much of the ultrasound procedure, the probe holder 100 and stand assembly 200 may prevent carpel tunnel syndrome and other repetitive stress injuries in the hand of the technician. In some embodiments, the grip portion 102 may be manually rotatable with respect to the skirt portion 126 as the grip portion base edge 116 on the grip portion base 106 slides on and with respect to the skirt portion apex edge 140 on the skirt portion apex 132 of the skirt portion 126. This expedient may facilitate corresponding rotation of the probe base 156 with respect to the skin 164 of the patient 162, enabling the technician to obtain different images of the organ or tissues being imaged.

In some applications, after use of the probe holder 100, the ultrasonic transducer probe 150 may be removed from the skirt portion 126, the grip portion 102 removed from the ultrasonic transducer probe 150 and the skirt portion 126 removed from the skin 164 of the patient 162. The grip portion 102 and the skirt portion 126 may be discarded or cleaned and reused.

Referring next to FIGS. 16-52 of the drawings, an alternative illustrative embodiment of the ultrasonic transducer probe holder, hereinafter probe holder 300, is illustrated. Unless otherwise noted, in the probe holder 300, elements which are analogous to the respective elements of the probe holder 100 that was heretofore described with respect to FIGS. 1-15 are designated by the same respective numerals in the 300-399 series in FIGS. 16-52. Accordingly, the same description which was set forth hereinabove with respect to the probe holder 100 in FIGS. 1-15 is incorporated by reference herein in its entirety with respect to the holder 300.

As illustrated in FIGS. 16-19, in some embodiments, a stand assembly 400 may facilitate mounting of the probe holder 300 on the bed, table, or other support 348 (FIGS. 38-45) on which the patient 362 reclines. The stand assembly 400 may facilitate multi-positioning of the probe holder 300 as the ultrasound technician 398 (FIGS. 42-49) operates and manipulates the ultrasonic transducer probe 350 in the probe holder 300 against the skin 364 of the patient 362. The stand assembly 400 may have any design which is suitable for the purpose. For example and without limitation, in some embodiments, the stand assembly 400 may include a stand base 402. The stand base 402 of the stand assembly 400 may be configured to securely engage a structural component of the support 348. Accordingly, the stand base 402 may include a main base member 404. A base member flange 406 may be disposed in spaced-apart relationship to the main base member 404. A base member arm 408 may connect the base member flange 406 to the main base member 404. The stand base 402 may be attached to a rail, panel, or other structural component (not illustrated) on the support 348 by placement of the component between the main base member 404 and the base member flange 406.

In some embodiments, a base adjustment knob 418 may be provided on the main base member 404 of the stand base 402. The base adjustment knob 418 may threadably engage the base member arm 408 according to the knowledge of those skilled in the art to facilitate extension and retraction of the base member arm 408 with respect to the stand base 402 by rotation of the base adjustment knob 418. Accordingly, the spacing between the main base member 404 and the base member arm 408 may be selectively adjusted by rotation of the base adjustment knob 418 to accommodate various thicknesses and facilitate placement and tightening of the stand base 402 on the support 348.

In some embodiments, various controls for the pump and supply mechanism 450 for the gel, the vacuum system 460, and/or other components of the ultrasonic transducer probe system may be provided on the main base member 404 of the stand base 402, typically as will be hereinafter described. The controls ray interface with the respective components via a wired or wireless connection according to the knowledge of those skilled in the art.

A first stand arm 412 may extend from the stand base 402. A second stand arm 420 may extend from the first stand arm 412. The probe holder 300 may be supported by the second stand arm 420, typically as will be hereinafter described. The stand assembly 400 may be selectively adjustable positionally to facilitate adjustment in the height and orientation of the probe holder 300. Accordingly, the first stand arm 412 may be selectively adjustable with respect to the stand base 402. The second stand arm 420 may be selectively adjustable with respect to the first stand arm 412. The probe holder 300 may be selectively adjustable with respect to the second stand arm 420.

In some embodiments, the first stand arm 412 of the stand assembly 400 may be elongated with a proximal arm end 414 and a distal arm end 416. The proximal arm end 414 of the first stand arm 412 may be pivotally attached to the stand base 402. Accordingly, in some embodiments, a base pivot fastener 410 may pivotally attach the proximal arm end 414 of the first stand arm 412 to the main base member 404 of the stand base 402. The base pivot fastener 410 may facilitate pivoting of the first stand arm 412 with respect to the stand base 402 typically within a vertical plane.

In some embodiments, the base pivot fastener 410 may be rotatably mounted to the main base member 404 of the stand base 402. Accordingly, the base pivot fastener 410 may additionally facilitate rotation of the first stand arm 412 along the longitudinal axis of the first stand arm 412.

The second stand arm 420 of the stand assembly 400 may be elongated with a proximal arm end 422 and a distal arm end 424. A first pivot fastener 426 may pivotally attach the proximal arm end 422 of the second stand arm 420 to the distal arm end 416 of the first stand arm 412. The first pivot fastener 426 may facilitate pivoting of the second stand arm 420 with respect to the first stand arm 412 typically within a vertical plane.

A holder mount clevis 432 may extend from the distal arm end 424 of the second stand arm 420. In some embodiments, a second pivot fastener 428 may pivotally attach the holder mount clevis 432 to the distal arm end 424 of the second stand arm 420. The holder mount clevis 432 may have any design which is configured to hold or support the probe holder 300. Accordingly, in some embodiments, the holder mount clevis 432 may have a clevis shaft 434. A clevis ring 436 may terminate a proximal end of the clevis shaft 434. The clevis ring 436 may be configured to receive the second pivot fastener 428 for pivotal attachment of the holder mount clevis 432 to the distal arm end 424 of the second stand arm 420. A ball socket ring 440 may extend from a distal end of the clevis shaft 434. The ball socket ring 440 may be sized and configured to engage the probe holder 300 in such a manner that the probe holder 300 is capable of swiveling within the ball socket ring 440, typically in a manner which will be hereinafter described. In some embodiments, a clevis attachment knob 438 may facilitate detachable attachment of the ball socket ring 440 to the clevis shaft 434 according to the knowledge of those skilled in the art.

A ring tensioning knob 442 may engage the ball socket ring 440. The ring tensioning knob 442 may be configured to threadably engage the ball socket ring 440 to facilitate selective adjustments in the width or diameter of the ball socket ring 440 for optimum engagement between the probe holder 300 and the ball socket ring 440.

As illustrated in FIGS. 20-34, the grip portion 302 of the probe holder 300 may include a grip portion wall 304 having a grip portion base 306, a grip portion apex 308 and an expanded grip portion middle section 310. A ball socket 370 may extend from the grip portion apex 308 of the grip portion 302. The ball socket 370 may be suitably sized and configured to be received in the ball socket ring 440 of the holder mount clevis 432 for swivel mounting of the ball socket 370 in the ball socket ring 440 and multi-positional mounting of the probe holder 300 with respect to the stand assembly 400.

Figure 32:
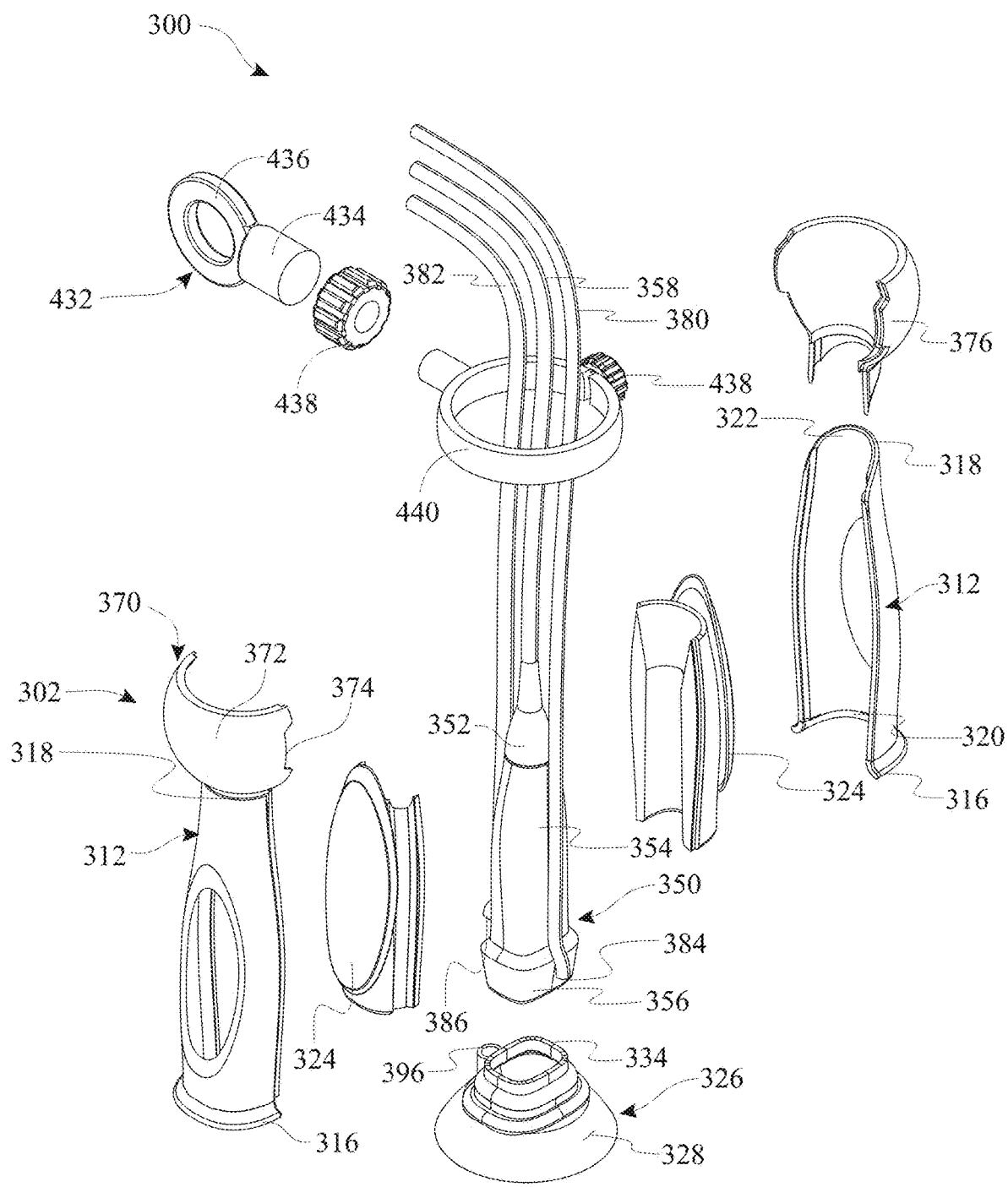
FIG. 32 presents an exploded perspective view of the ultrasonic transducer probe and the disassembled ultrasonic transducer probe holder.
Figure 33:
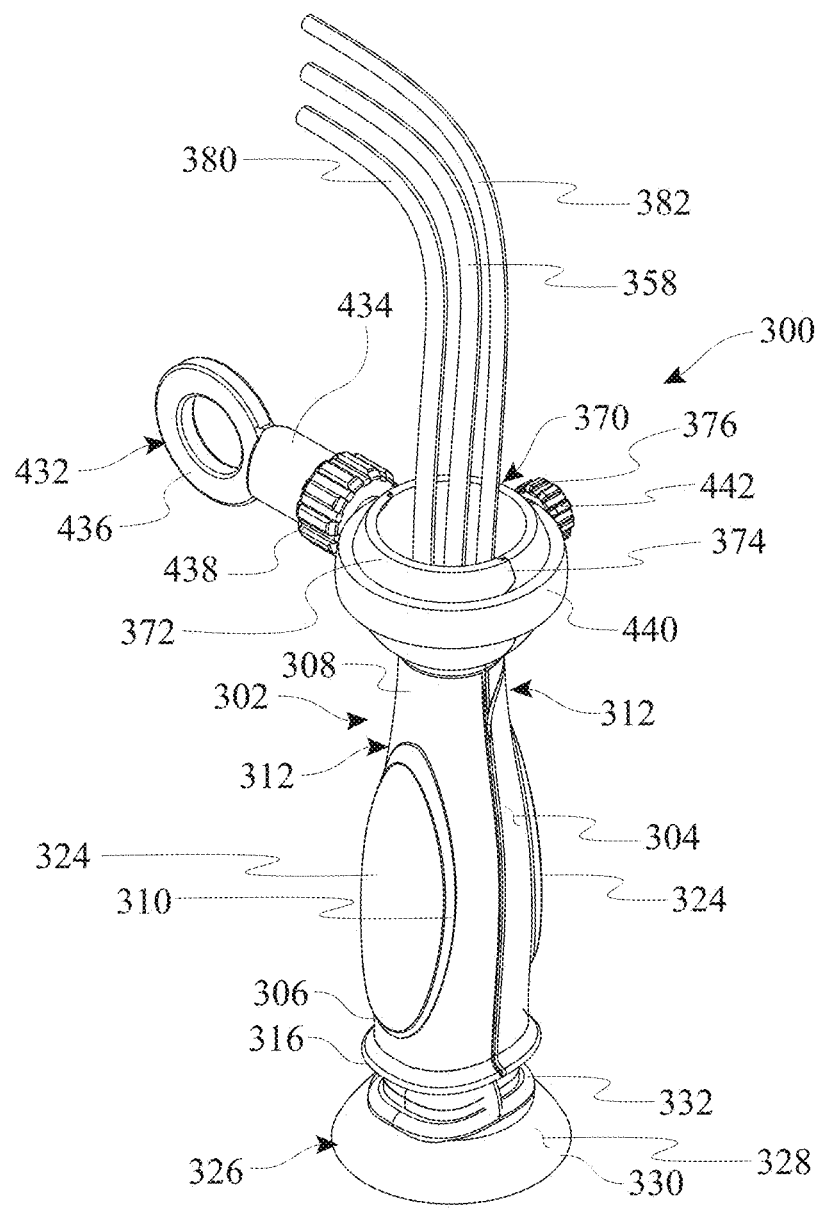
FIG. 33 presents a top perspective view of the assembled ultrasonic transducer probe holder, with the mount clevis attached to the ball socket of the probe holder.
Figure 34:
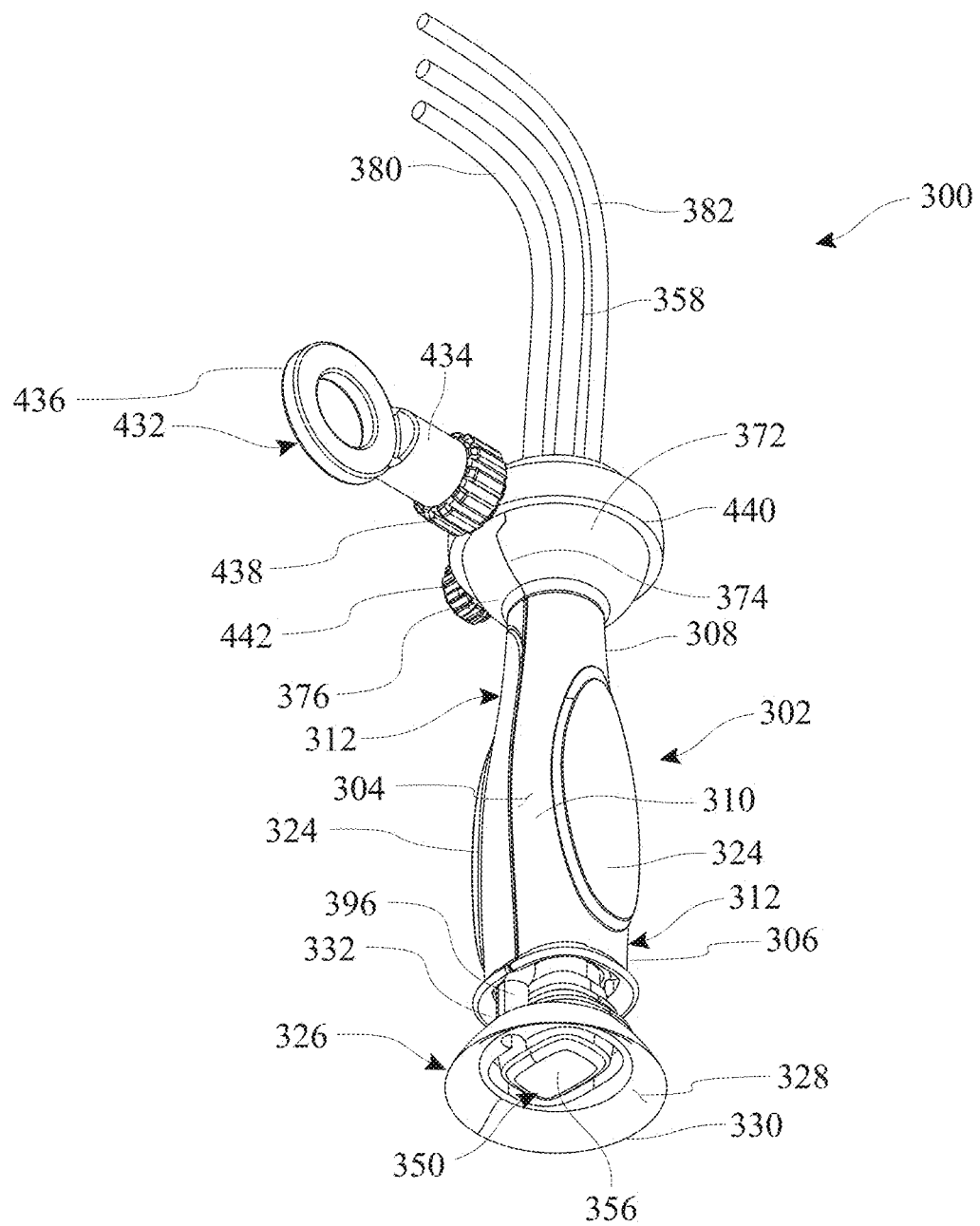
FIG. 34 presents a bottom perspective view of the assembled ultrasonic transducer probe holder and ultrasonic transducer probe.

The grip portion 302 may have a pair of mating grip portion sections 312. The grip portion sections 312 of the grip portion 302 may be configured to detachably engage each other via a flanged connection, a tongue in groove connection, or the like. In some embodiments, the ball socket 370 may have a fixed ball socket section 372 and a detachable ball socket section 376. The fixed ball socket section 372 may extend from one of the mating grip portion sections 312 of the grip portion 302. The detachable ball socket section 376 may be configured to detachably engage the fixed ball socket section 372 at a suitable attachment interface 374. Accordingly, in typical assembly of the probe holder 300 on the ultrasonic transducer probe 350, as illustrated in FIG. 32 and will be hereinafter described, the grip portion sections 312 may detachably engage each other. The detachable ball socket section 376 may detachably engage the fixed ball socket section 372 to form the ball socket 370 for swivel attachment of the probe holder 300 to the stand assembly 400.

As further illustrated in FIG. 32, in some embodiments, each grip portion section 312 of the grip portion 302 may be fitted with a grip pad 324. Each grip pad 324 may be inserted from the inside out through an elongated grip pad opening (not numbered) in each corresponding grip portion section 312.

Figure 30:
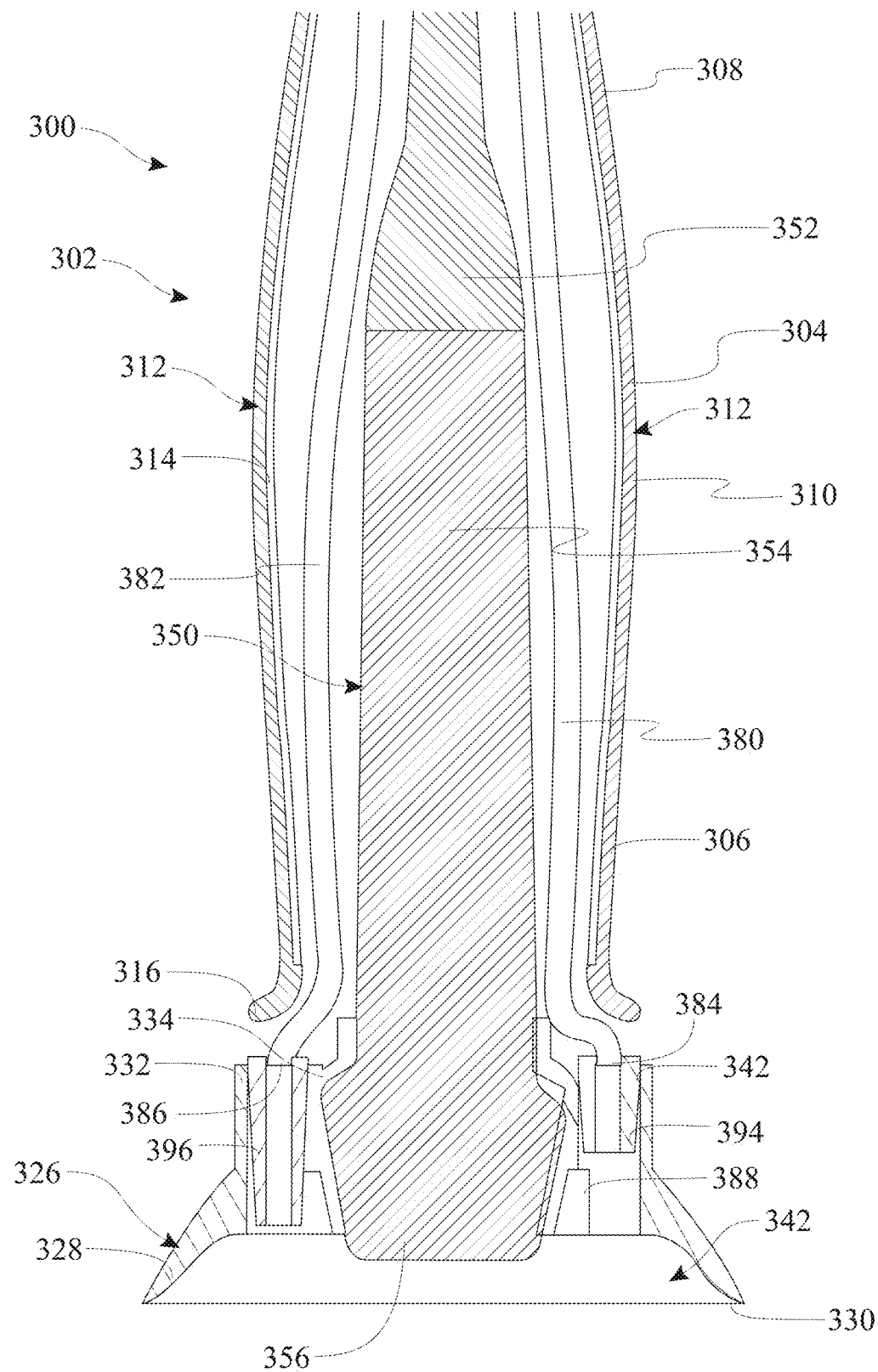
FIG. 30 presents an enlarged longitudinal sectional view of the grip portion of the ultrasonic transducer probe holder assembled on the ultrasonic transducer probe illustrated in FIG. 29.
Figure 31:
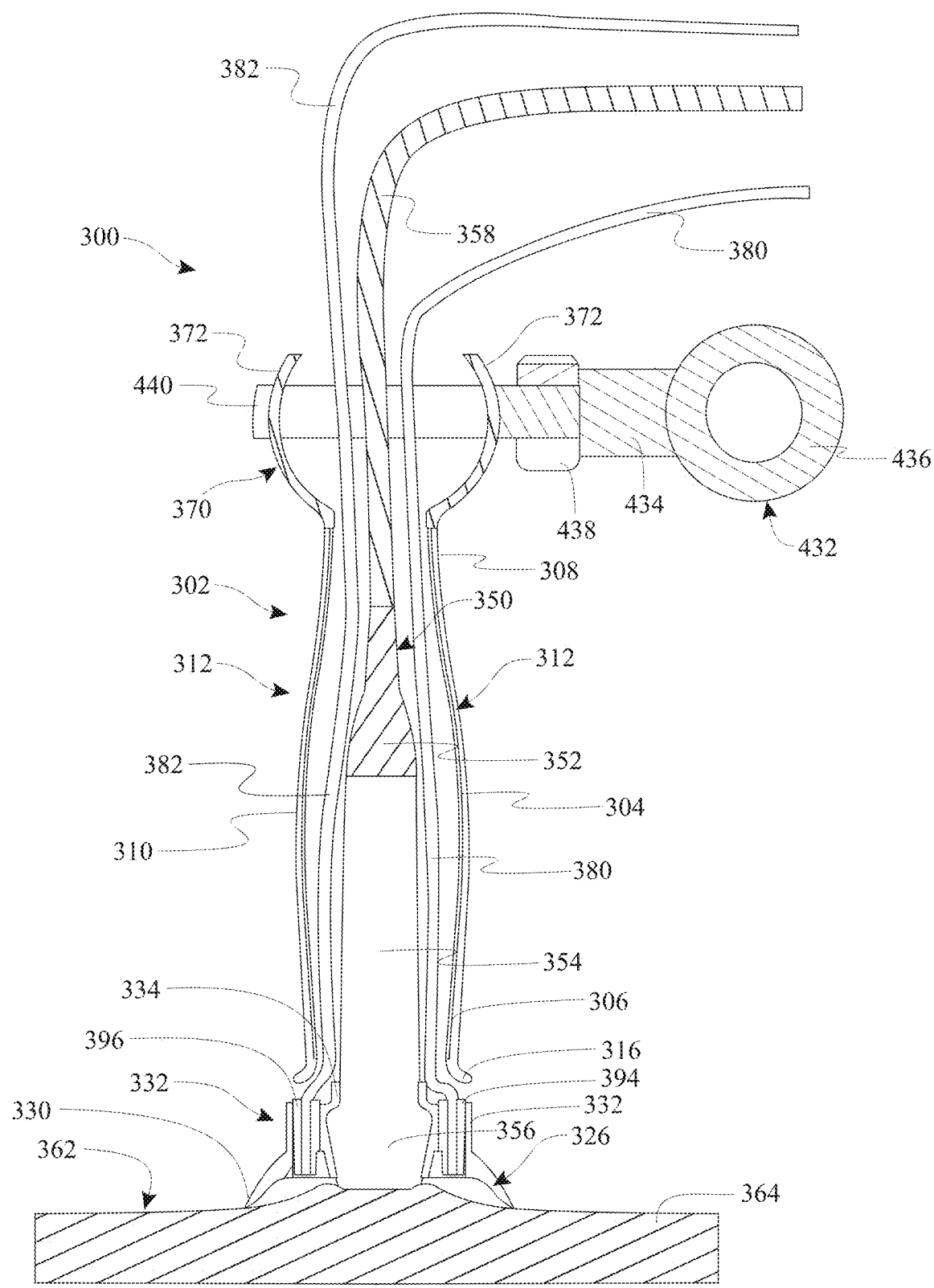
FIG. 31 presents a longitudinal sectional view of the assembled ultrasonic transducer probe holder and ultrasonic transducer probe with the probe applied to the skin of a patient in typical application of the probe holder.

As illustrated in FIG. 30, the skirt portion 326 may include a skirt portion wall 328 formed with a skirt portion base 330 and a skirt portion apex 332. A central transducer mount portion 334 may be disposed in the skirt portion interior 342 of the skirt portion 326. The transducer mount portion 334 may be suitably sized and configured to receive and support the probe base 356 of the ultrasonic transducer probe 350 in assembly of the grip portion 302 on the ultrasonic transducer probe 350.

The skirt portion wall 328 of the skirt portion 326 may be fabricated of a flexible material such as silicone, rubber or plastic, for example and without limitation. In some embodiments, the resiliency of the skirt portion wall 328 may render the skirt portion 326 capable of retracting or folding backwards, or turning inside out, in a manner which is similar to that of an umbrella being flipped inside out by a strong gust of wind, typically for purposes which will be hereinafter described. The flipped skirt portion 326 may be deployed back into position with a downward swipe of the hand.

A vacuum tube port 394 and a gel tube port 396 may be provided in the skirt portion interior 342 of the skirt portion 326. The vacuum tube end 384 of the vacuum tube 380 may terminate in fluid communication with the vacuum tube port 394. The gel tube end 386 of the gel tube 382 may terminate in fluid communication with the gel tube port 396. In some embodiments, the vacuum tube end 384 of the vacuum tube 380 and the gel tube end 386 of the gel tube 382 may be suitably sized and configured to insert into the respective vacuum tube port 394 and gel tube port 396.

The vacuum tube 380 and the gel tube 382 may extend from the skirt portion apex 332 of the skirt portion 326. The vacuum tube 380 may be connected to a vacuum system 460 (FIG. 37), and the gel tube 382 may be connected to a pump and supply mechanism 450 (FIG. 37) which contains a conductive gel (not illustrated).

As further illustrated in FIG. 30, in some embodiments, an annular vacuum distribution trough 388 may be provided in the skirt portion 326. The vacuum distribution trough 388 may be disposed in fluid communication with the vacuum tube port 394. The vacuum distribution trough 388 may be formed by and between the skirt portion wall 328 and the transducer mount portion 334 of the skirt portion 326.

Figure 35:
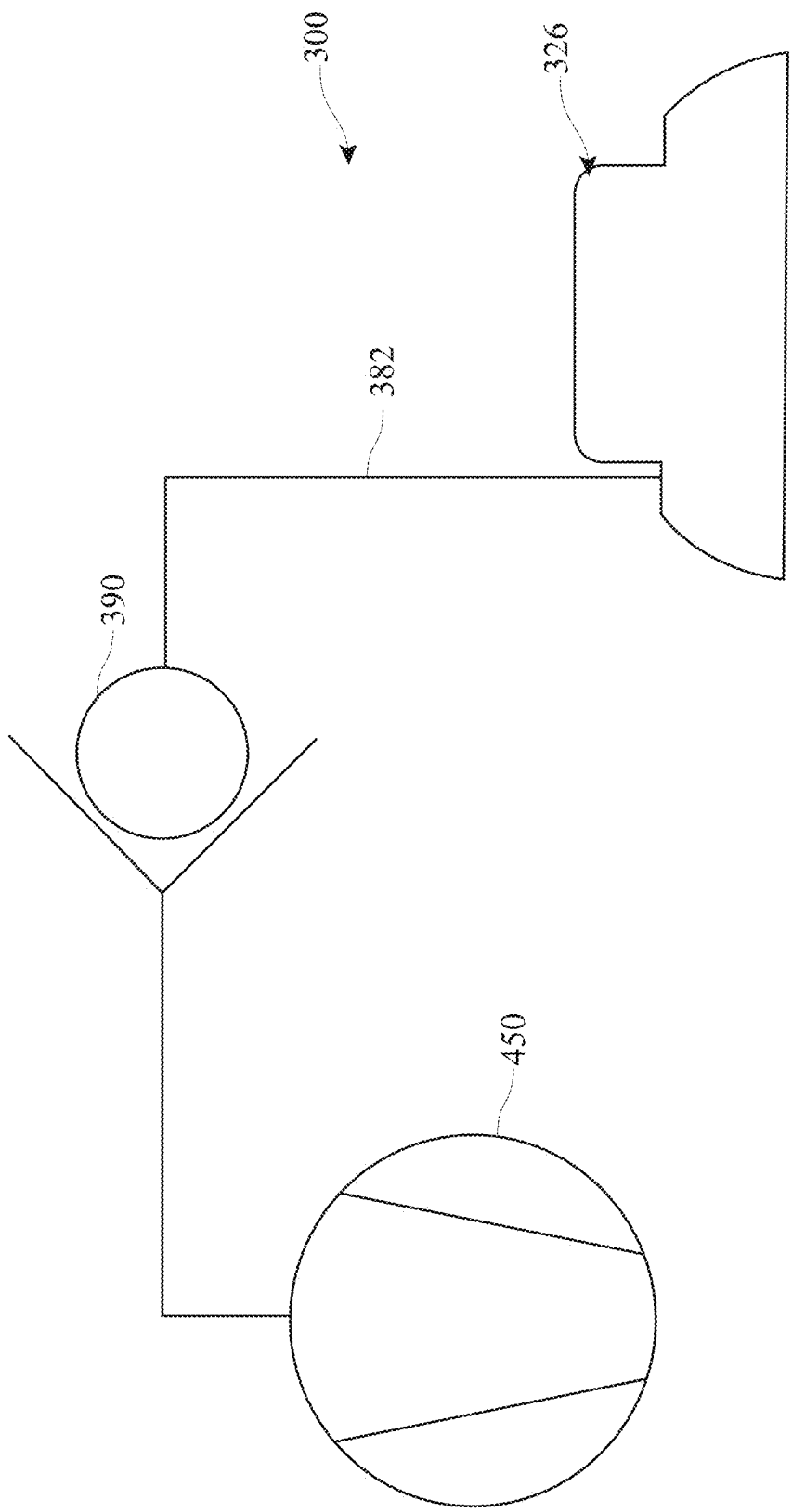
FIG. 35 presents a block diagram of a typical gel distribution circuit suitable for distributing gel from a pump and supply mechanism to the skirt portion of the ultrasonic transducer probe holder.
Figure 36:
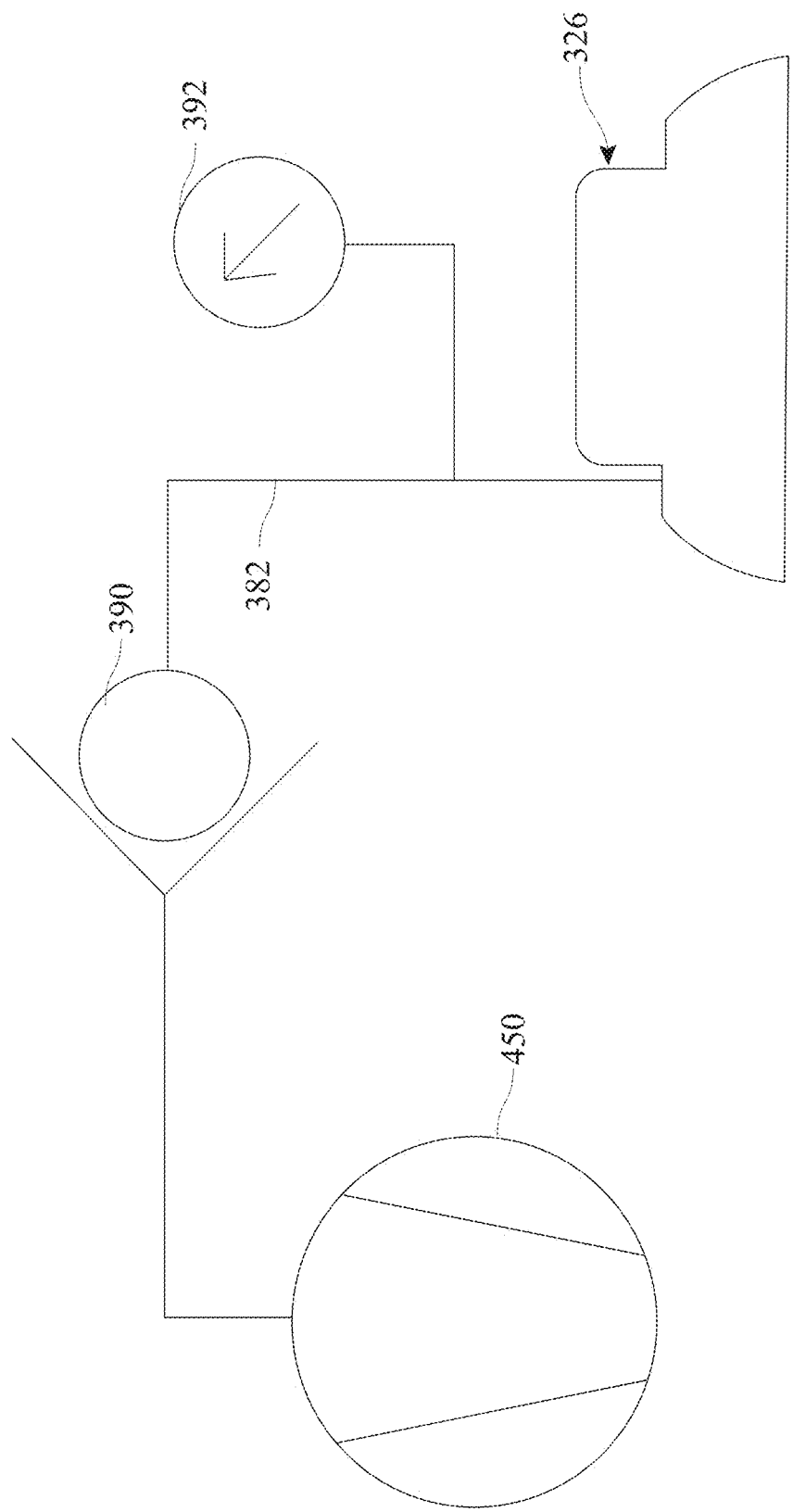
FIG. 36 presents a block diagram of the gel distribution circuit with a pressure transducer between a check valve and the skirt portion of the ultrasonic transducer probe holder.

As illustrated in FIGS. 35 and 36, a typical gel distribution circuit which is suitable for distributing gel from the pump and supply mechanism 450 to the skirt portion 326 of the probe holder 300 is shown. The gel tube 382 may establish fluid communication between the pump and supply mechanism 450 and the gel tube port 396 (FIG. 30) in the skirt portion interior 342 of the skirt portion 326. At least one check valve 390 may be provided in the gel tube 382. The check valve 390 may facilitate unidirectional flow of the gel from the pump and supply mechanism 450 to the skirt portion 326 while preventing backflow of the gel through the gel tube 382.

As illustrated in FIG. 36, in some embodiments, at least one pressure transducer 392 may be provided in the gel tube 382 of the gel distribution circuit. The pressure transducer 392 may be configured to measure the pressure of the gel as the gel flows through the gel tube 382. In some embodiments, the pressure transducer 392 may operationally interface with the pump and supply mechanism 450 to facilitate feedback control of the pumping action for regulation of the pressure of the gel as the gel flows through the gel tube 382. In some embodiments, a pressure gauge (not illustrated) may operationally interface with the pressure transducer 392. The pressure gauge may be configured to visually indicate the pressure of the gel as the gel flows through the gel tube 382.

Figure 37:
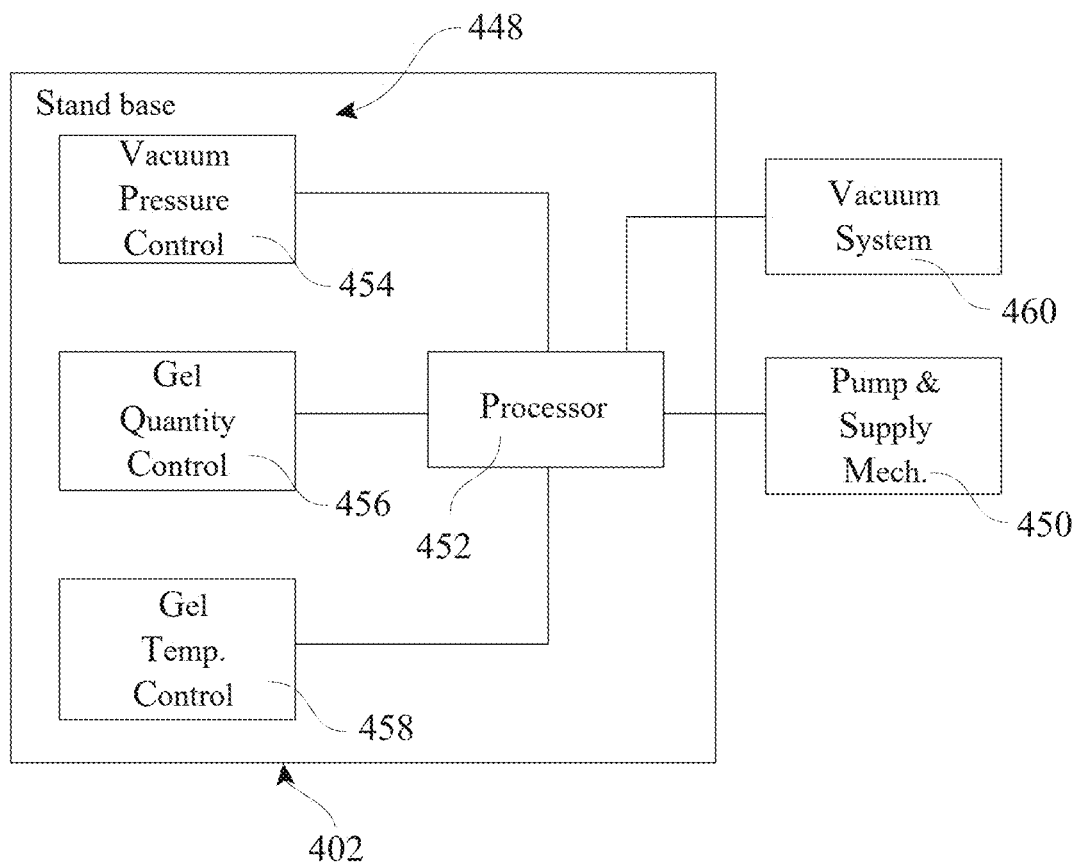
FIG. 37 presents a block diagram of a typical vacuum pressure control, gel quantity control and gel temperature control for the pump and supply mechanism of the ultrasonic transducer probe holder.

As illustrated in FIG. 37, in some embodiments, a user interface 448 for at least some or all of the components of the medical ultrasound system may be provided on the stand base 402 of the stand assembly 400. Accordingly, the user interface 448 may include a vacuum pressure control 454. The vacuum pressure control 454 may operationally interface with the vacuum system 460, typically through a processor 452. The vacuum system 460 may be configured to control or regulate the vacuum pressure which is applied to the vacuum tube port 394 (FIG. 30) through the vacuum tube 380 responsive to manipulation of the vacuum pressure control 454. Accordingly, the vacuum pressure control 454 may be configured to control the pressure of the skirt portion 326 against the skin 364 of the patient 362 as the gel is dispensed from the skirt portion 326 of the probe holder 300 onto the skin 364 of the patient 362. In some applications, for example and without limitation, the vacuum strength applied through the vacuum tube 380 may quickly ramp up and then level off or plateau at the preferred vacuum pressure strength.

In some embodiments, the user interface 448 may include a gel quantity control 456. The gel quantity control 456 may operationally interface with the pump and supply mechanism 450, typically through the processor 452. The pump and supply mechanism 450 may be configured to control or regulate the quantity or volume of the gel responsive to manipulation of the gel quality control 458. Accordingly, the gel quantity control 456 may thus be configured to control the quantity of volume of the gel dispensed from the skirt portion 326 of the probe holder 300 onto the skin 364 of the patient 362.

In some embodiments, the user interface 448 may include a gel temperature control 458. The gel temperature control 458 may operationally interface with the pump and supply mechanism 450. The pump and supply mechanism 450 may include one or more heating elements (not illustrated) configured to heat the gel responsive to manipulation of the gel temperature control 458. Additionally or alternatively, at least one warming coil (not illustrated) may be provided typically at or adjacent to the gel tube end 386 (FIG. 30) of the gel tube 382 for warming of the gel before or as it is dispensed from the gel tube port 396 for increased comfort to the patient 362. Accordingly, the gel temperature control 458 can be manipulated to control the temperature of the gel dispensed from the skirt portion 326 of the probe holder 300 onto the skin 364 of the patient 362.

The vacuum pressure control 454, the gel quantity control 456 and/or the gel temperature control 458 and/or other features of the user interface 448 may be provided in any location or position which is accessible to the ultrasound technician 398. For example and without limitation, in some embodiments, the user interface 448 may be provided on the main base member 404 of the stand base 402 of the stand assembly 400. Additional controls of the user interface 448, such as vacuum power, sustain, and/or time settings, for example and without limitation, may be included on the main base member 404 of the stand base 402 and/or in any other suitable accessible location or locations. In some embodiments, the vacuum pressure control 454, the gel quantity control 456, the gel temperature control 458 and/or other features of the user interface 448 may include a touch sensor with circuitry known by those skilled in the art.

As illustrated in FIGS. 38-52, in typical application, the stand assembly 400 may be mounted on the support 348 on which the patient 362 reclines. Accordingly, the ultrasound technician 398 may adjust the spacing between the base member flange 406 and the main base member 404 of the stand base 402, typically by rotation of the base adjustment knob 418, depending on the thickness of the rail, panel, or other element on the support 348 to which the stand assembly 400 is mounted.

Figure 38:
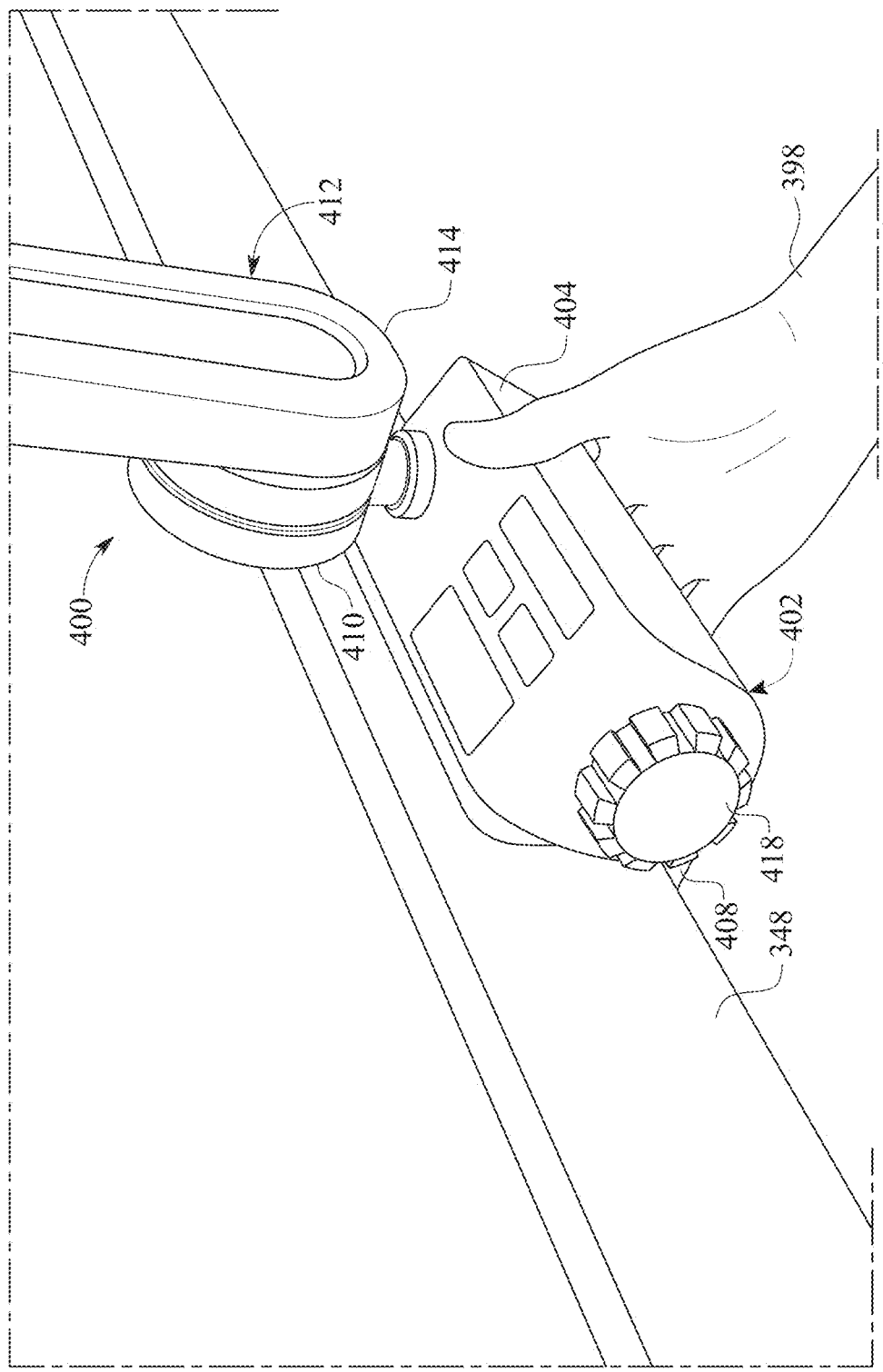
FIGS. 38-52 present perspective views of the ultrasonic transducer probe holder in typical application of the probe holder.
Figure 39:
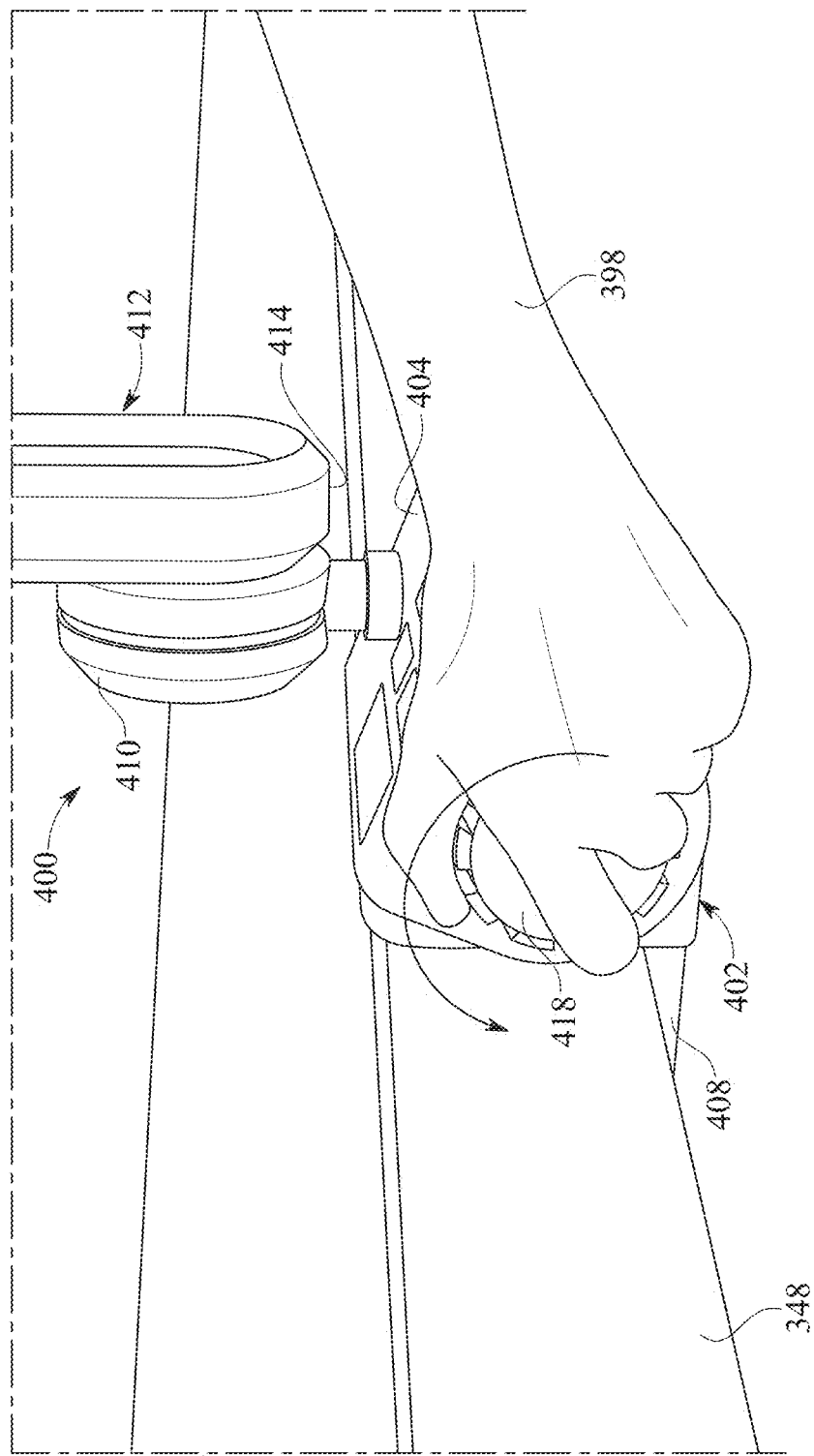

As illustrated in FIG. 38, the support 348 may be placed between the main base member 404 and the base member flange 406. As illustrated in FIG. 39, the base adjustment knob 418 may then be rotated to clamp or tighten the support 348 between the base member flange 406 and the main base member 404.

Figure 40:
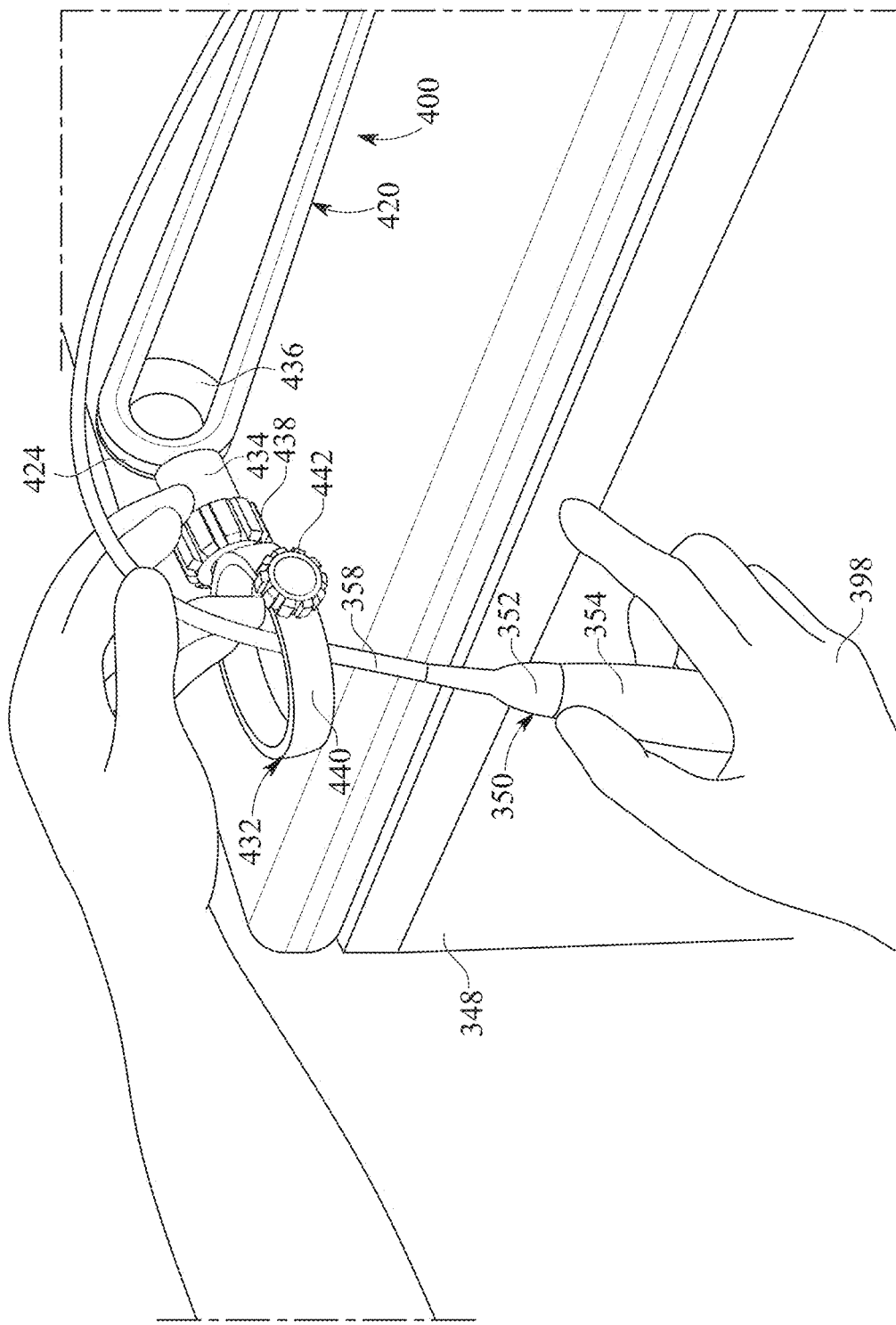
Figure 41:
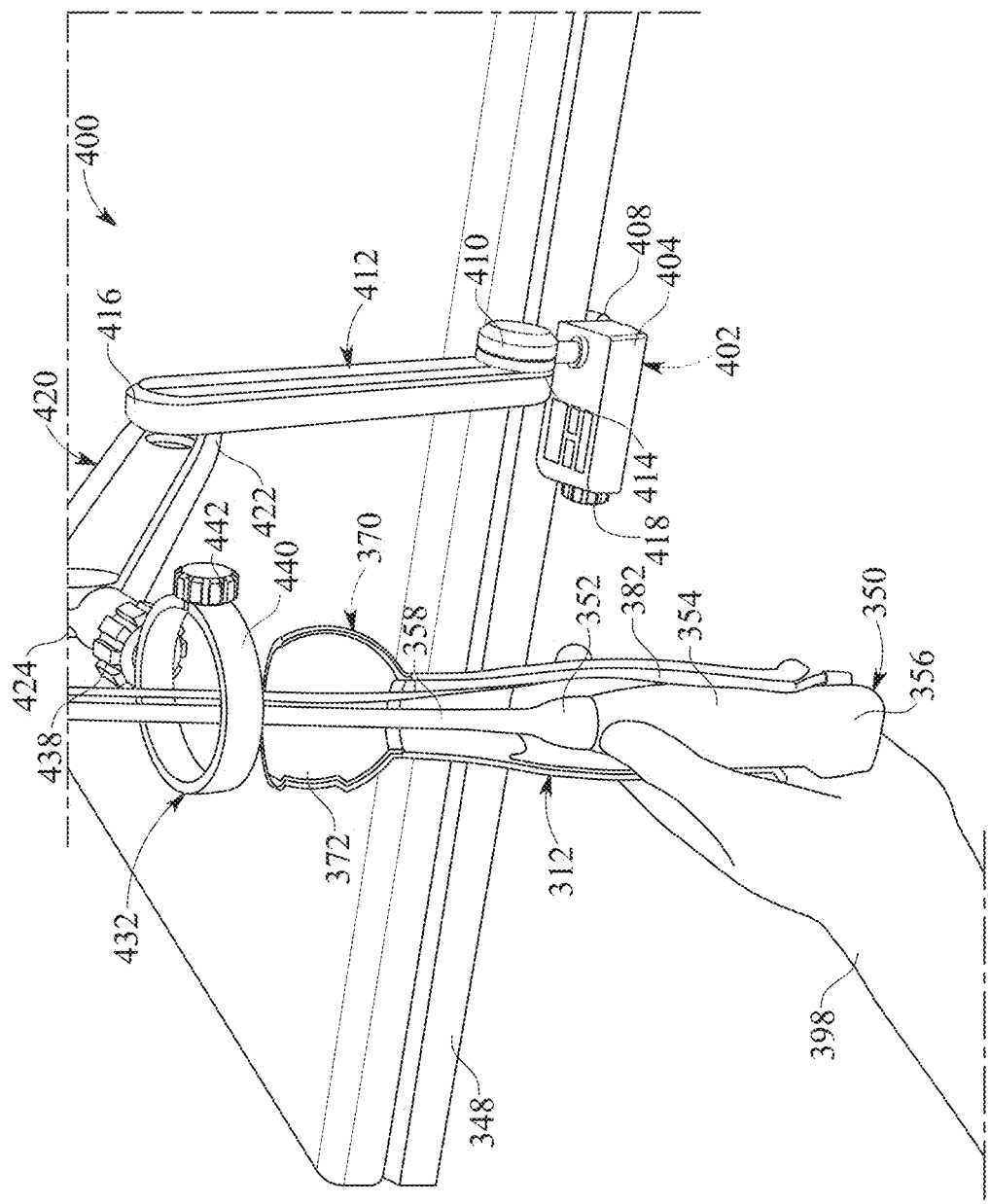
Figure 42:
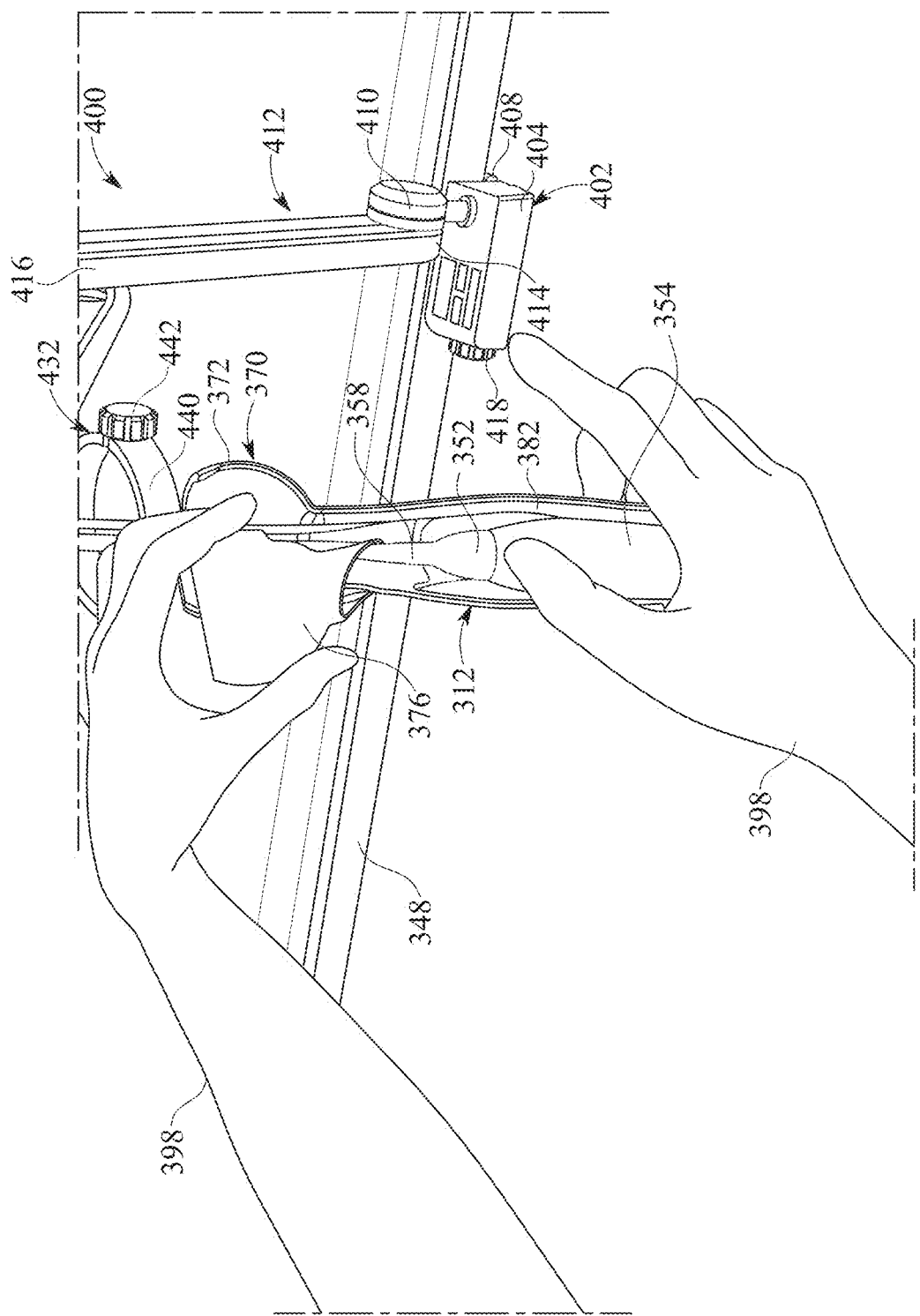

As illustrated in FIG. 40, the ultrasonic transducer probe 350 may next be fed through the ball socket ring 440 of the holder mount clevis 432 on the stand assembly 400 until the probe cable 358 extends through the ball socket ring 440. The ultrasonic transducer probe 350 may then be placed inside the grip portion section 312 of the grip portion 302 from which the fixed ball socket section 372 of the ball socket 370 extends, as illustrated in FIG. 41. As illustrated in FIG. 42, the detachable ball socket section 376 may then be snapped in place on the fixed ball socket section 372 to complete assembly of the ball socket 370.

Figure 43:
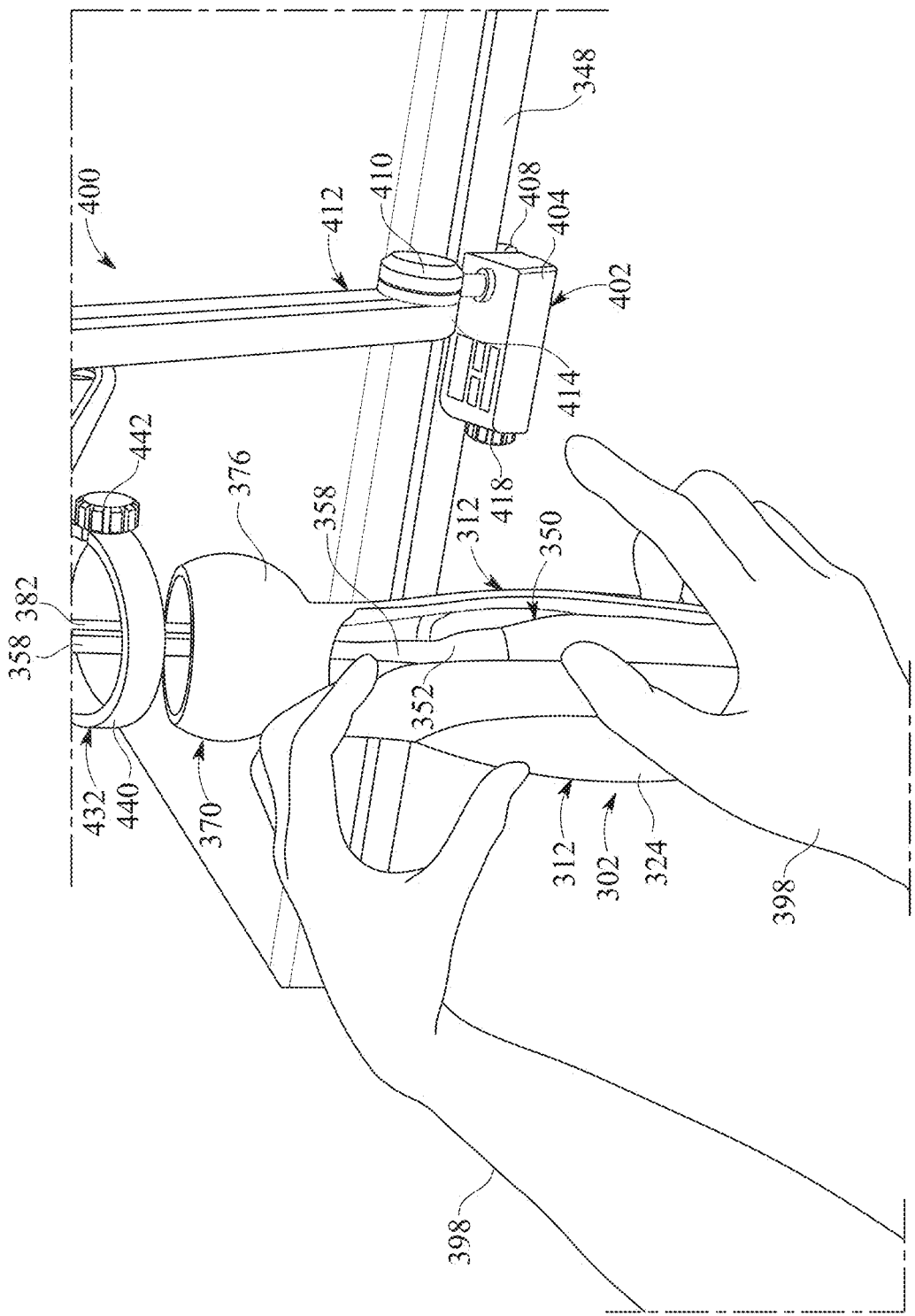
Figure 44:
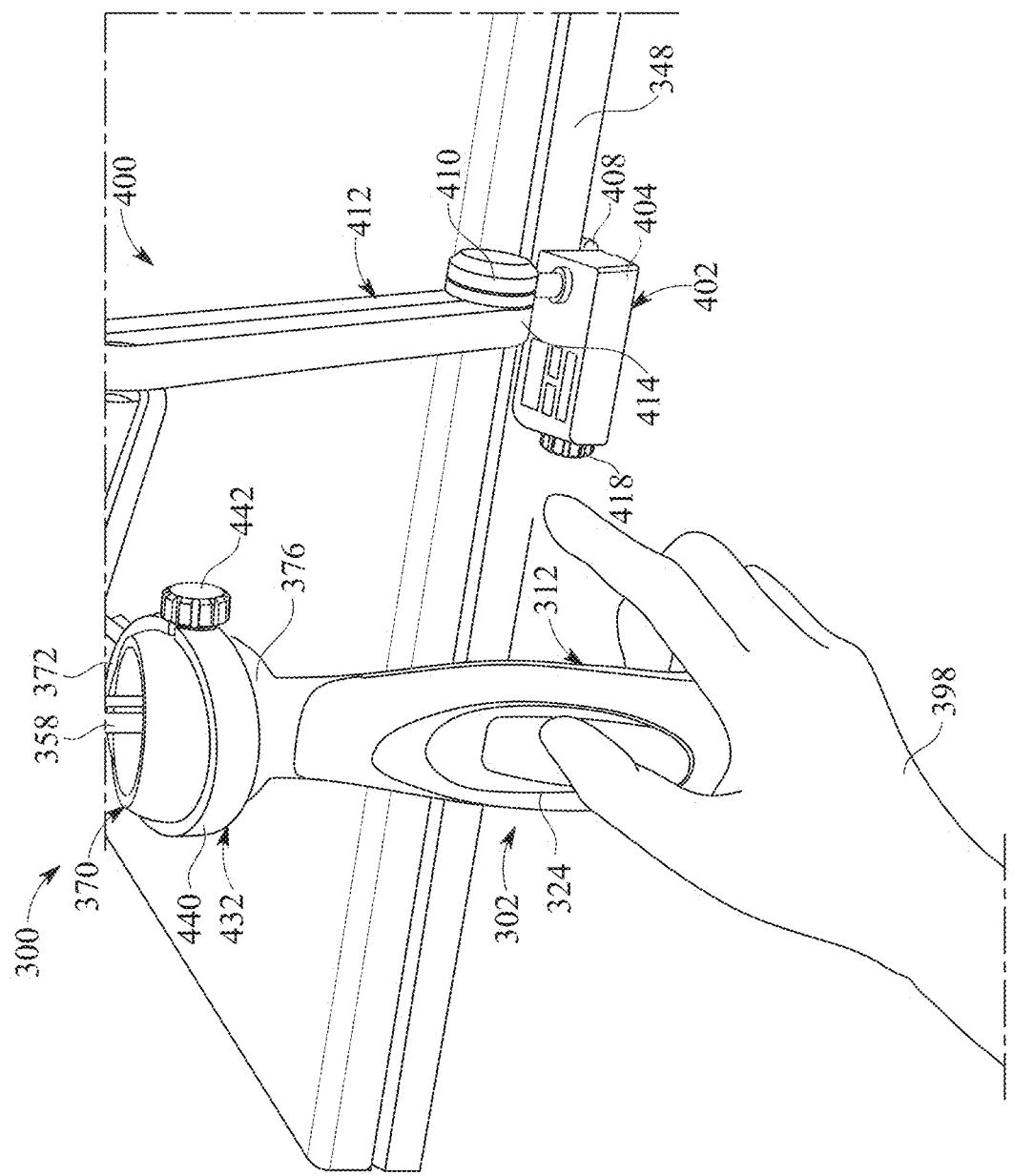

As illustrated in FIG. 43, the remaining grip portion section 312 may be snapped in place on the first grip portion section 312 to complete assembly of the grip portion 302. The remaining grip portion section 312 may remain structurally separate from the ball socket 370 to facilitate cleaning of the ultrasonic transducer probe 350 without the need to completely remove the ultrasonic transducer probe 350 from the ball socket 370. As illustrated in FIG. 44, the ball socket 370 may then be inserted into the ball socket ring 440 of the holder mount clevis 432.

Figure 45:
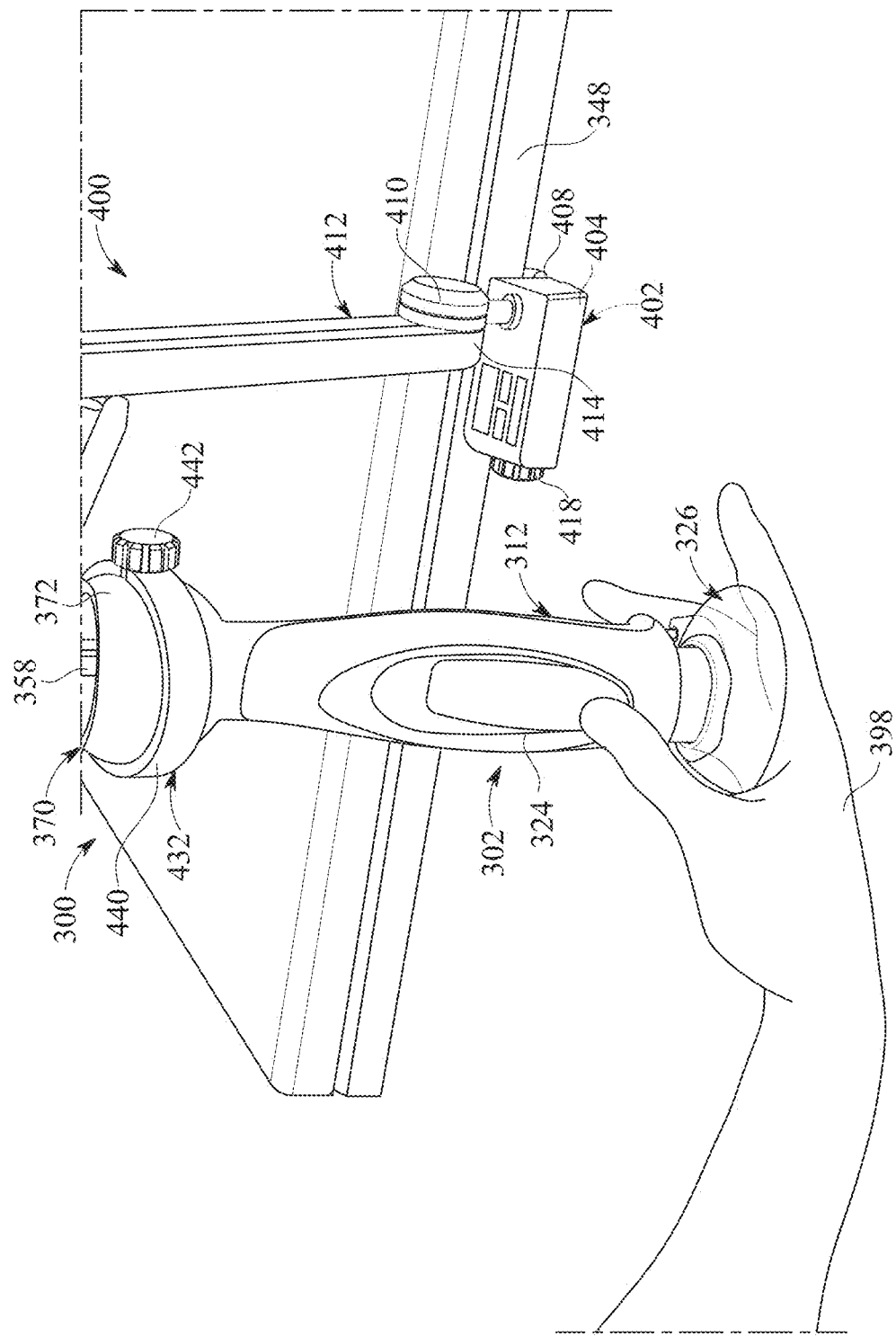
Figure 46:
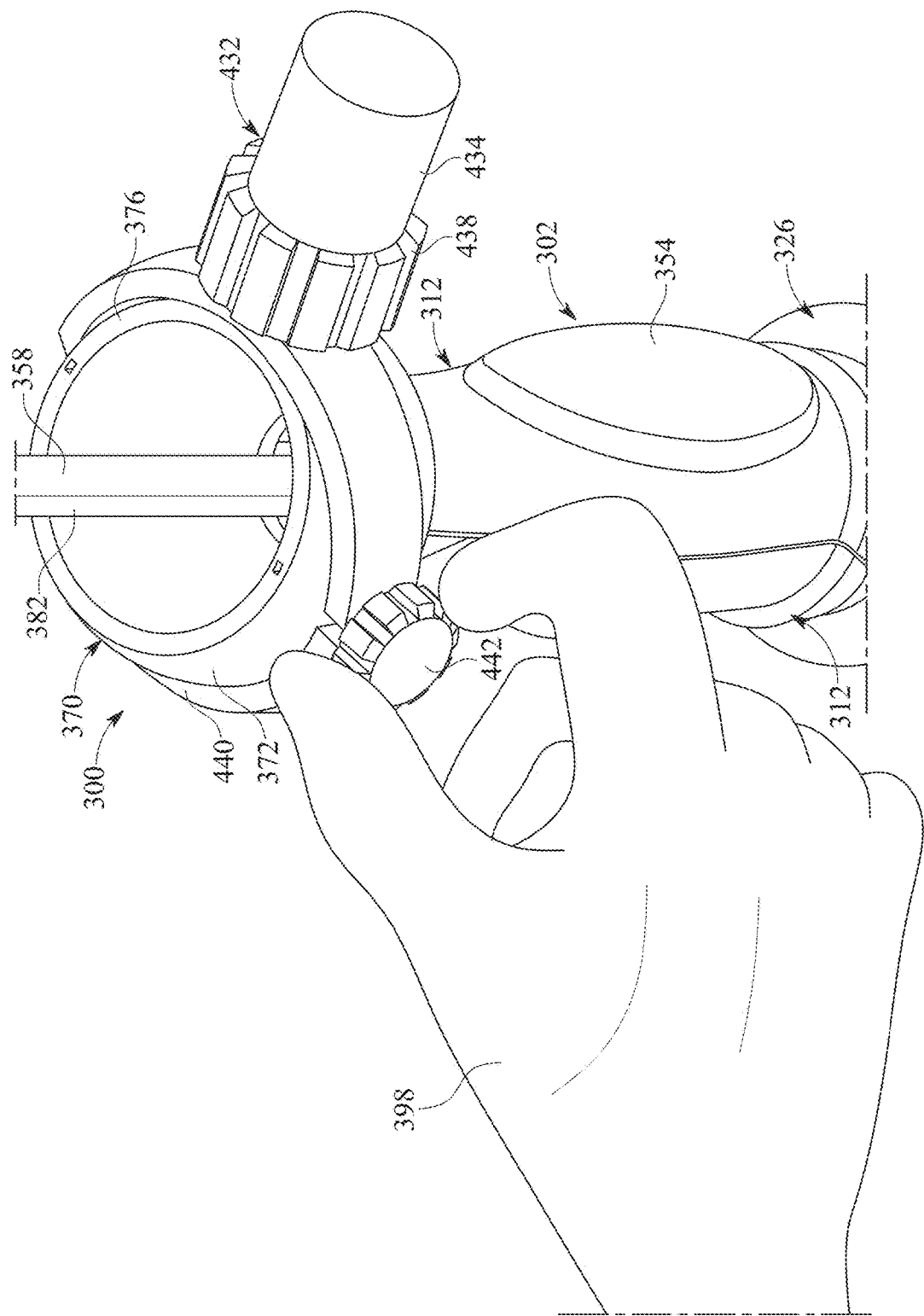

As illustrated in FIG. 45, the flexible skirt portion 326 may be placed over the probe base 356 of the ultrasonic transducer probe 350 as the vacuum tube end 384 (FIG. 30) of the vacuum tube 380 is inserted into the vacuum tube port 394. The gel tube end 386 of the gel tube 382 may be inserted into the gel tube port 396. The ball socket ring 440 of the holder mount clevis 432 may next be tightened against the ball socket 370 of the probe holder 300, typically by rotating the ring tensioning knob 442, as illustrated in FIG. 46.

Figure 47:
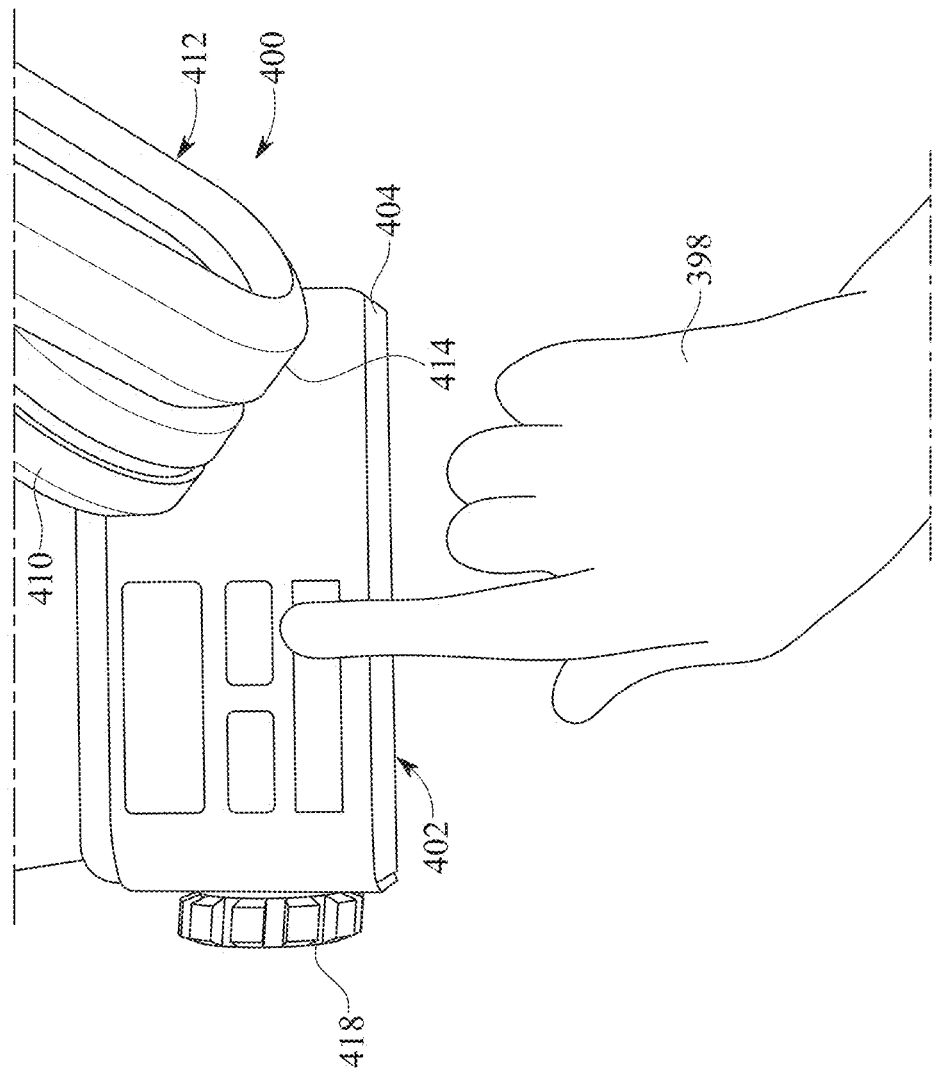

As illustrated in FIG. 47, the medical ultrasound system may be powered on typically by manipulation of the user interface 448. Settings such as vacuum power, sustain, and/or time settings may be adjusted by the ultrasonic technician 398. For example and without limitation, as illustrated in FIG. 37, in some applications, the vacuum pressure control 454, the gel quantity control 456 and/or the gel temperature control 458 may be manipulated by the ultrasonic technician 398 to facilitate adjustments in the vacuum pressure, the gel quantity or volume and/or the gel temperature, respectively.

Figure 48:
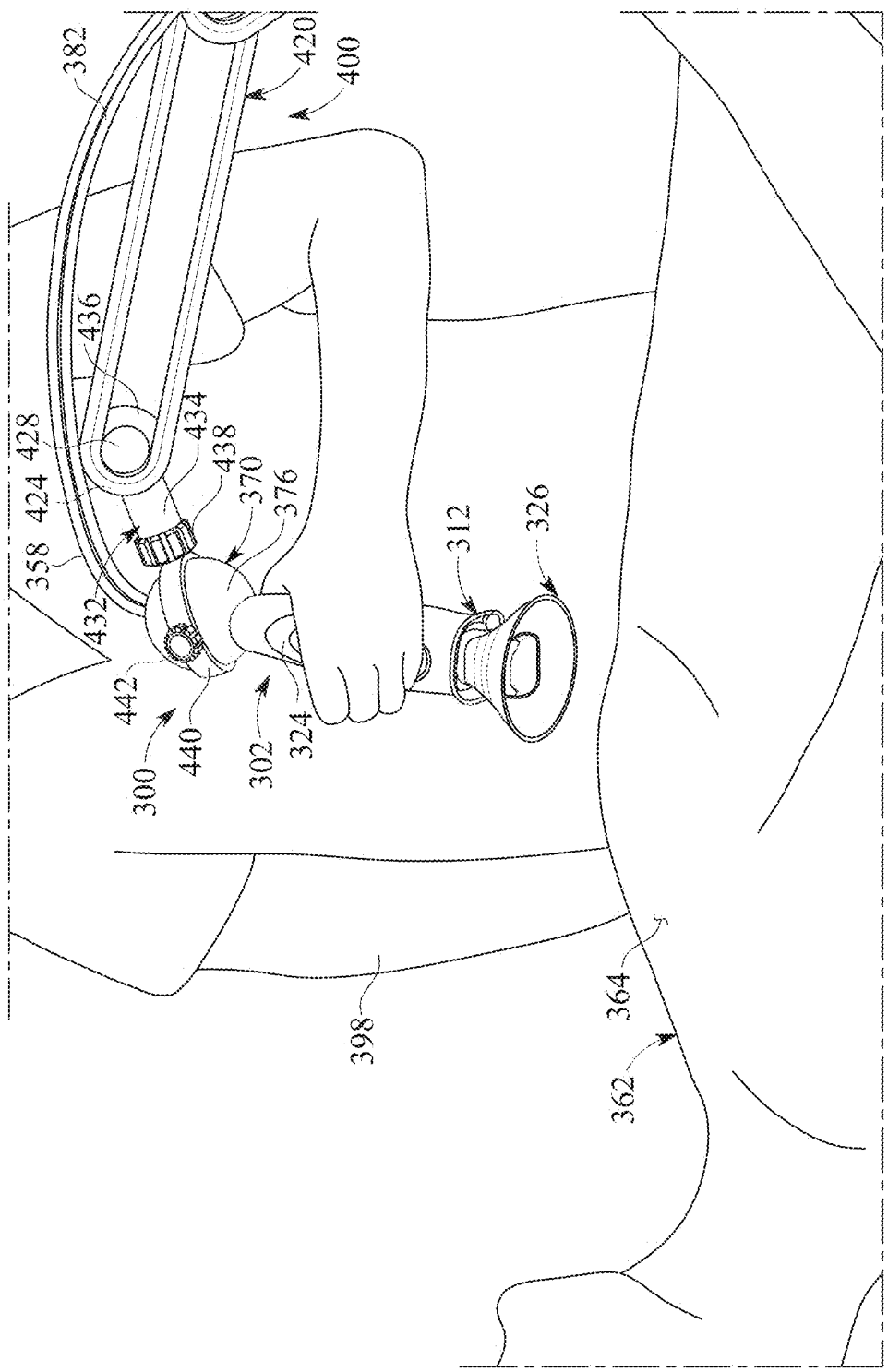
Figure 49:
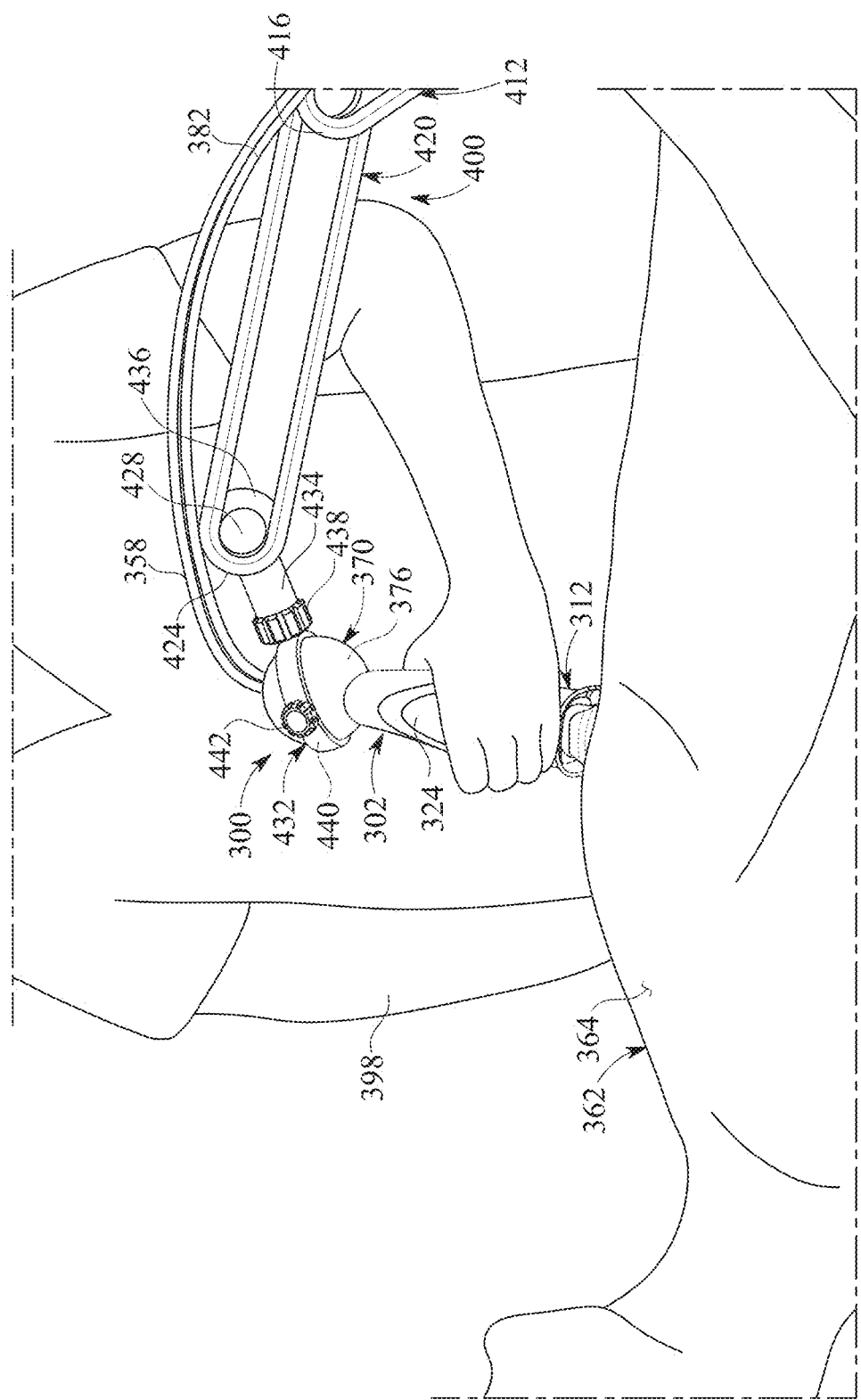
Figure 50:
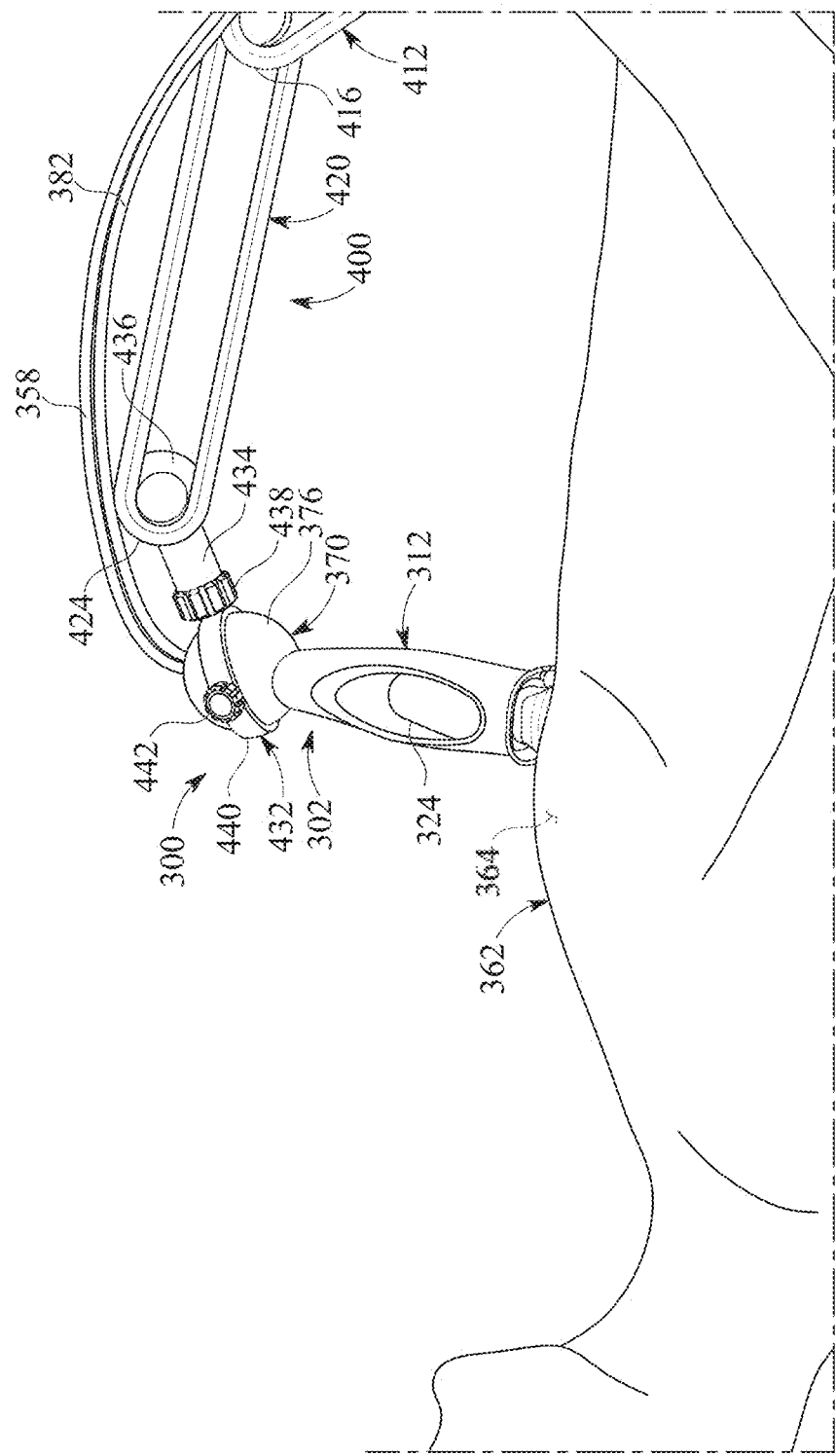

As illustrated in FIG. 48, the ultrasound technician 398 may grasp the probe holder 300 and position the skirt portion 326 against the skin 364 of the patient 362. The position of the probe holder 300 may be manipulated until the desired view on the patient 362 is found. The ultrasonic transducer probe 350 may then be activated by squeezing the grip pads 324 on the respective grip portion sections 312 of the grip portion 302, typically twice. This action may cause the vacuum system to apply vacuum pressure to the vacuum tube port 394 (FIG. 30) through the vacuum tube 380, thereby applying vacuum pressure to the annular vacuum distribution trough 388 in the skirt portion 326. Accordingly, uniform vacuum pressure in the skirt portion interior 342 of the skirt portion 326 may facilitate application of the skirt portion 326 to the skin 364 of the patient 362 along a uniform seal, gently holding the probe base 356 of the ultrasonic transducer probe 350 against the patient's skin 364, as illustrated in FIG. 49. The ultrasound technician 398 is thus free to view the ultrasound data which is outputted by the ultrasonic transducer probe 350 without having to sustain manual pressure of the ultrasonic transducer probe 350 against the patient's skin 364, as illustrated in FIG. 50.

Figure 51:
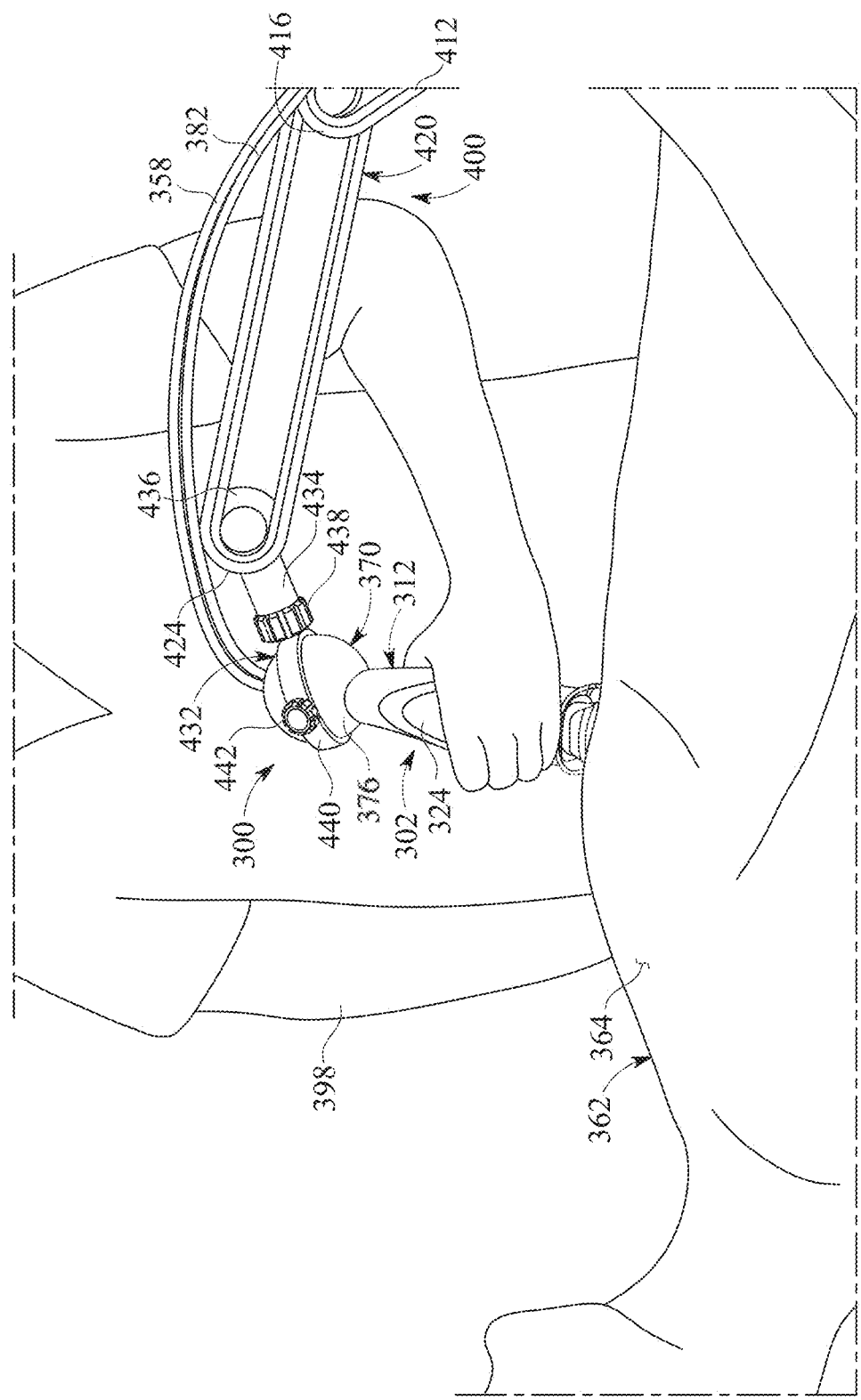
Figure 52:
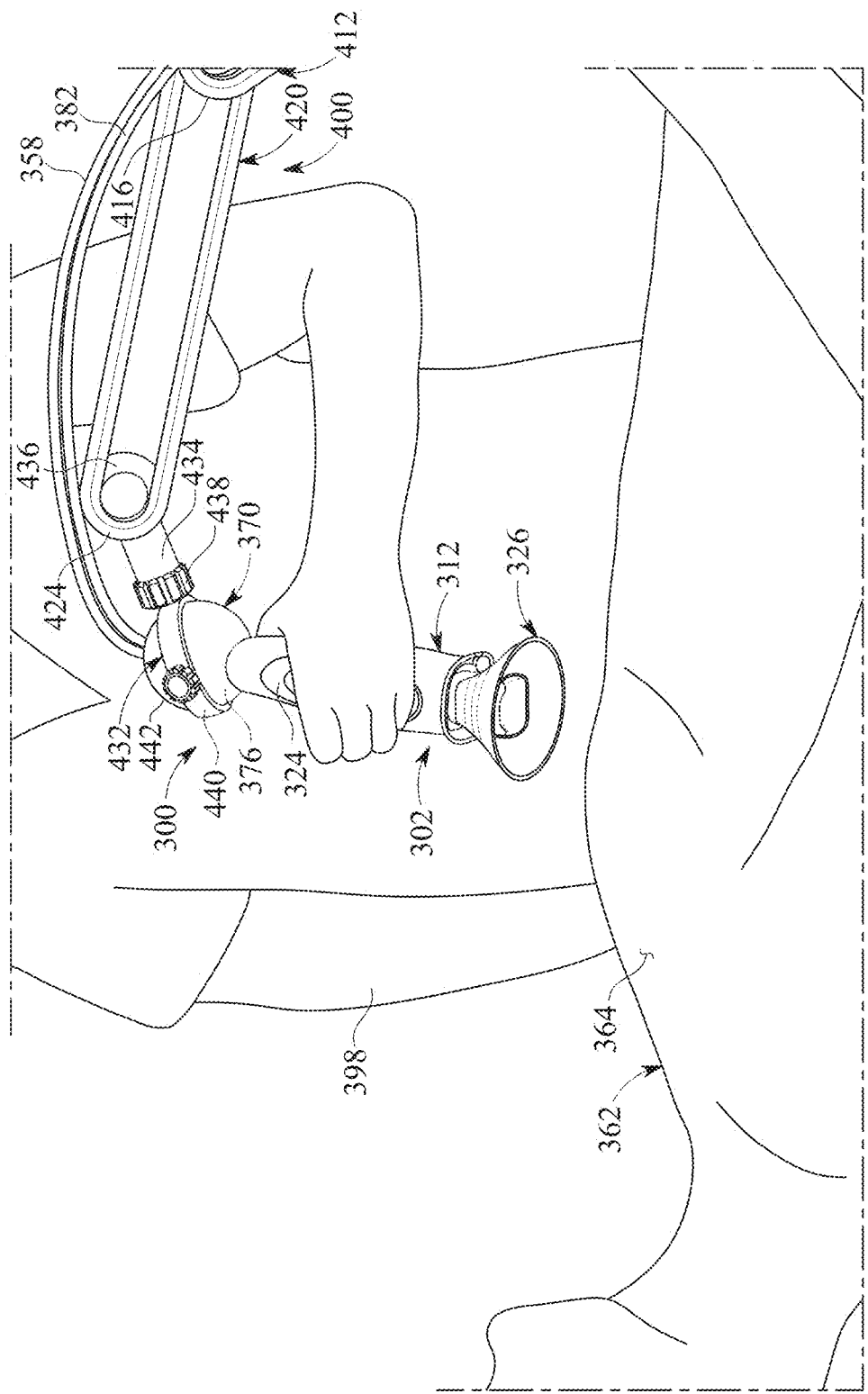

As illustrated in FIG. 51, after the ultrasonic viewing of the patient is completed, the ultrasound technician 398 may terminate further application of vacuum pressure to the vacuum tube port 394 typically by again squeezing the grip pads 324 on the grip portion 302. As illustrated in FIG. 52, the probe holder 300 with the ultrasonic transducer probe 350 therein may then be moved to a different location on the skin 364 of the patient 362 to obtain another image, typically in the manner which was heretofore described.

In some applications, the ultrasonic transducer probe 350 may be used to obtain a view known as a supra sternal notch view which is taken with the probe 350 applied just beneath the "Adams apple" of the patient 362. This view may require direct exposure of the probe base 356 of the probe 350. As set forth herein above, to achieve this purpose, the skirt portion 326 may be designed to retract or fold backwards with a simple swipe of the hand. The skirt portion 326 may subsequently be deployed back into position with a downward swipe of the hand.

It will be appreciated by those skilled in the art that the probe holders 100, 300 represent an immediate and universally applicable method to markedly lessen the musculoskeletal traumas associated with chronic sonography activities. Its simple design and ease of application is the first of its kind to reduce musculoskeletal traumas most directly and efficiently during the acquisition of images. It is a relatively low-cost method that allows the sonographer and institutions to use their current probes, protocol, and computer machinery as they are already accustomed. The lamprey acts like an invisible assistant sonographer that unburdens the actual sonographer from the daily brunt force work allowing them to maintain proper posture and markedly reduce the possibility of musculoskeletal trauma thereby avoiding career ending muscle and joint strain. Conventionally, sonographers identify a particular probe position which is maintained with one hand with application of pressure while the free hand does typing, measurements and manipulations with the computer keyboard. Another location is then identified, and new sets of pictures obtained. An average to complex study may have 60 to 120 images. Normally the dominant hand using the probe maintains pressure and positioning throughout the length of the study. Now with introduction of the new lamprey accessory the sonographer only has to locate the line of sight of their image and release the probe freeing the hand, wrist, arm and shoulder from any further use of pressure. Upon release the probe position in space is maintained and vacuum pressure is initiated producing a downward force of the probe into the chest wall as would normally be provided by the sonographer. The position is held as long as needed while the sonographer makes additional measurements and recordings before proceeding to the next imaging location. Upon touching and repositioning the probe the vacuum releases and upon securing the next position the vacuum engages when the hand is released from the probe. The probe maintains neutral buoyancy in space allowing for easy maneuverability. No forceful tugging of the probe is required further minimizing any muscle strain. The lamprey will allow future echocardiographic studies with negligible inherent muscular trauma and provide built-in muscle recovery time. The lamprey should significantly change the field of sonography allowing more senior sonographers to continue imaging later into their careers adding to the knowledge base and proficiency of echocardiography programs.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An ultrasonic transducer probe holder suitable for holding an ultrasonic transducer probe of a medical ultrasound system in place against the skin of a patient as an ultrasound technician manually releases the probe, the medical ultrasound system having a pump and supply mechanism configured for pumping conductive gel and a vacuum system configured for applying vacuum pressure to the ultrasonic transducer probe holder, the ultrasonic transducer probe holder comprising:
   a grip portion configured for deployment on the ultrasonic transducer probe, the grip portion comprising a flexible grip portion wall including:
      a grip portion base;
      a grip portion apex;
      a grip portion middle section between the grip portion base and the grip portion apex, the grip portion middle section of the grip portion wall expandable to a greater diameter or width than a diameter or width of the grip portion base and the grip portion apex of the grip portion wall; and
      the grip portion comprising a pair of detachable, mating grip portion sections;
   a skirt portion configured to form a vacuum seal against the skin of the patient responsive to operation of the vacuum system, the skirt portion further configured to support the grip portion and comprising:
      a flexible skirt portion wall having a skirt portion apex at the grip portion;
      a skirt portion base opposite the skirt portion apex;
      a skirt portion interior formed by the skirt portion wall; and
      a central transducer mount portion disposed in the skirt portion interior;
   a ball socket on the grip portion, the ball socket comprising:
      a fixed ball socket section extending from a first one of the mating grip portion sections of the grip portion; and
      a detachable ball socket section attachable to the fixed ball socket section and to a second one of the mating grip portion sections of the grip portion; and
   a stand assembly configured for mounting on a support, the stand assembly comprising:
      a stand base;
      at least one stand arm pivotally supported by the stand base; and
      a holder mount clevis pivotally supported by the at least one stand arm, the holder mount clevis comprising a ball socket ring, wherein the ball socket on the grip portion is insertable in the ball socket ring.

2. The ultrasonic transducer probe holder of claim 1 further comprising a vacuum tube port in the skirt portion interior of the skirt portion, and wherein the vacuum tube is configured for placement into fluid communication with the vacuum tube system.

3. The ultrasonic transducer probe holder of claim 1 further comprising a gel tube configured for placement into fluid communication with the skirt portion interior, the gel tube configured to distribute conductive gel to the skirt portion interior of the skirt portion.

4. The ultrasonic transducer probe holder of claim 1 wherein the at least one stand arm comprises a first stand arm pivotally supported by the stand base and a second stand arm pivotally supported by the first stand arm, and wherein the holder mount clevis is pivotally supported by the second stand arm.

5. The ultrasonic transducer probe holder of claim 1 further comprising a user interface on the stand base of the stand assembly, the user interface configured to facilitate operation of the pump and supply mechanism and the vacuum system of the medical ultrasound system.

6. The ultrasonic transducer probe holder of claim 5 wherein the user interface comprises a vacuum pressure control, and gel quantity control and a gel temperature control.

* * * * *